United States Patent
Wang et al.

(10) Patent No.: US 12,076,148 B2
(45) Date of Patent: Sep. 3, 2024

(54) SYSTEMS AND METHODS FOR AUTOMATED RECOGNITION OF BODILY EXPRESSION OF EMOTION

(71) Applicant: THE PENN STATE RESEARCH FOUNDATION, University Park, PA (US)

(72) Inventors: James Z. Wang, State College, PA (US); Yu Luo, State College, PA (US); Jianbo Ye, State College, PA (US); Reginald B. Adams, Pennsylvania Furnace, PA (US)

(73) Assignee: THE PENN STATE RESEARCH FOUNDATION, University Park (PA)

( * ) Notice: Subject to any disclaimer, the term of this patent is extended or adjusted under 35 U.S.C. 154(b) by 844 days.

(21) Appl. No.: 16/918,604

(22) Filed: Jul. 1, 2020

(65) Prior Publication Data

US 2021/0000404 A1    Jan. 7, 2021

Related U.S. Application Data

(60) Provisional application No. 62/870,901, filed on Jul. 5, 2019.

(51) Int. Cl.
*A61B 5/16* (2006.01)
*A61B 5/00* (2006.01)
*A61B 5/11* (2006.01)
*A61B 5/117* (2016.01)
(Continued)

(52) U.S. Cl.
CPC ............ *A61B 5/165* (2013.01); *A61B 5/1128* (2013.01); *A61B 5/117* (2013.01); *A61B 5/7264* (2013.01);
(Continued)

(58) Field of Classification Search
CPC ......... A61B 5/165; A61B 5/117; A61B 5/128; A61B 5/7275; G16H 20/70; G16H 10/60; G16H 50/50
See application file for complete search history.

(56) References Cited

U.S. PATENT DOCUMENTS 8,308,562 B2 * 11/2012 Patton ................... A63F 13/30
463/43
9,208,326 B1    12/2015 Gates et al.
(Continued)

FOREIGN PATENT DOCUMENTS

CN    108363978 A    8/2018

OTHER PUBLICATIONS

Gunes, Hatice et al. "Bodily Expression for Automatic Affect Recognition." Emotion Recognition: A Pattern Analysis Approach, First Edition. John Wiley & Sons, Inc., 2014. Accessed Feb. 20, 2019. https://pdfs.semanticscholar.org/6c48/4d2509e601c0982638df91a34cbd490fd0da.pdf.
(Continued)

*Primary Examiner* — Catherine M Voorhees
*Assistant Examiner* — Roland Dinga
(74) *Attorney, Agent, or Firm* — Dinsmore & Shohl LLP

(57) ABSTRACT

An emotion analysis and recognition system including an automated recognition of bodily expression of emotion (ARBEE) system is described. The system may include program instructions executable by a processor to: receive a plurality of body movement models, each body movement model generated based on a crowdsourced body language dataset, calculate at least one evaluation metric for each body movement model, select a highest ranked body movement model based on the at least one metric calculated for each body movement model, combine the highest ranked body movement model with at least one other body move-
(Continued)

ment model of the plurality of body movement models, calculate at least one evaluation metric for each combination of body movement models, and determine a highest ranked combination of body movement models to predict a bodily expression of emotion.

20 Claims, 55 Drawing Sheets

(51) Int. Cl.
  *G16H 10/60* (2018.01)
  *G16H 20/70* (2018.01)
  *G16H 50/50* (2018.01)
(52) U.S. Cl.
  CPC ........... *A61B 5/7275* (2013.01); *G16H 10/60* (2018.01); *G16H 20/70* (2018.01); *G16H 50/50* (2018.01)

(56) References Cited

U.S. PATENT DOCUMENTS

| | | | |
|---|---|---|---|
| 2006/0047515 A1* | 3/2006 | Connors | G10L 17/26 704/E17.002 |
| 2007/0286489 A1* | 12/2007 | Amini | G06V 20/10 382/103 |
| 2014/0280296 A1 | 9/2014 | Johnston et al. | |
| 2018/0039745 A1 | 2/2018 | Chevalier et al. | |

OTHER PUBLICATIONS

Kleinsmith, Andrea et al. "Form as a Cue in the Automatic Recognition of Non-acted Affective Body Expressions." Affective Computing and Intelligent Interaction: 4th International Conference, Proceedings, Part I, Oct. 2011. DOI: 10.1007/978-3-642-24600-5_19. https://www.researchgate.net/publication/225218269_Form_as_a_Cue_in_the_Automatic_Recognition_of_Non-acted_Affective_Body_Expressions.

Luo, Yu et al. "ARBEE: Towards Automated Recognition of Bodily Expression of Emotion In the Wild." International Journal of Computer Vision. Computer Vision and Pattern Recognition, Aug. 28, 2018. http://arxiv.org/abs/1808.09568.

Noroozi, Fatemeh et al. "Survey on Emotional Body Gesture Recognition." Journal of IEEE Transactions on Affective Computing, Jan. 23, 2018. https://arxiv.org/pdf/1801.07481.pdf.

* cited by examiner

Click Here for instructions
Click Here for tutorial with concrete examples
What emotion category do you think Person 1 in the video presents?
(Please scroll for entire list)

☐ Peace: well being and relaxed; no worry; having positive thoughts or sensations; satisfied ☐ Affection: fond feelings; love; tenderness ☐ Esteem: feelings of favorable opinion or judgement; respect; admiration; gratefulness ☐ Anticipation: state of looking forward; hoping on or getting prepared for possible future events ☐ Engagement: paying attention to something; absorbed or something; curious, interested ☐ Confidence: feeling of being certain; conviction that an outcome will be favorable; encouraged; proud ☐ Happiness: feeling delighted, feeling enjoyment or amusement ☐ Pleasure: feeling of delight in the senses ☐ Excitement: feeling enthusiasm; stimulated; energetic

[ PREVIOUS ]

Click Here for instructions
Click Here for tutorial with concrete examples
Q4. Which frames do you think best presents the person's emotion?
Tip: Use the playback speed dropdown to help find the right frames indicated by the red number at the top left in the bottom pane.

Start Frame   End Frame   Playback Rate
   0            121          1.00 x

PREVIOUS   SUBMIT

FIG. 5D

FIG. 8
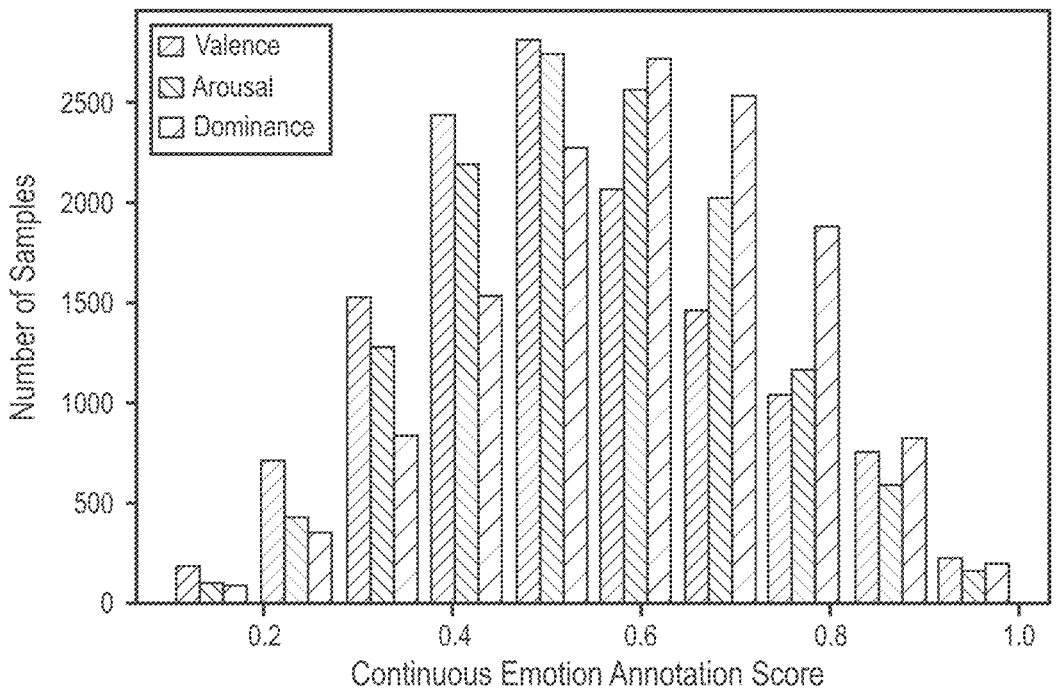
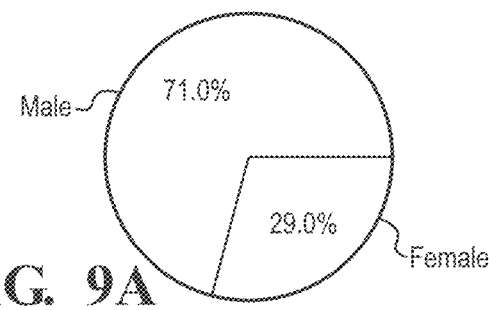
FIG. 9A
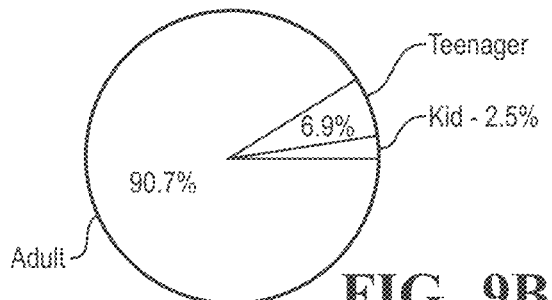
FIG. 9B
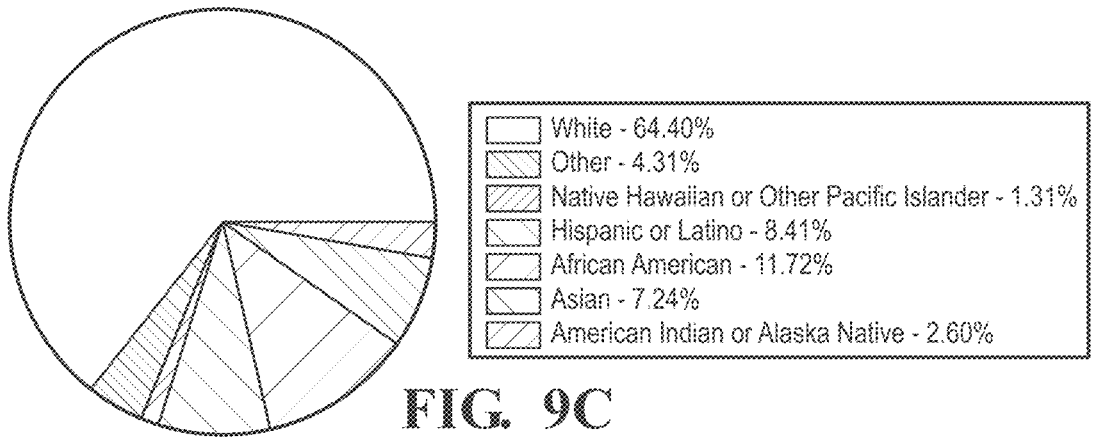
FIG. 9C

FIG. 12A
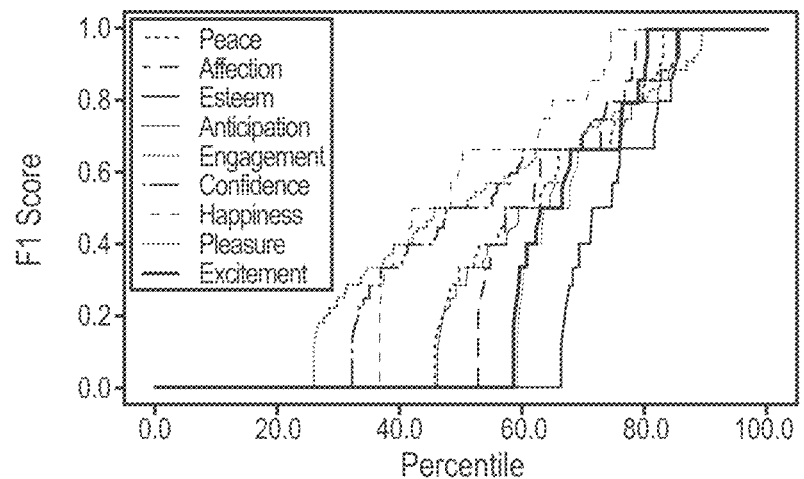
FIG. 12B
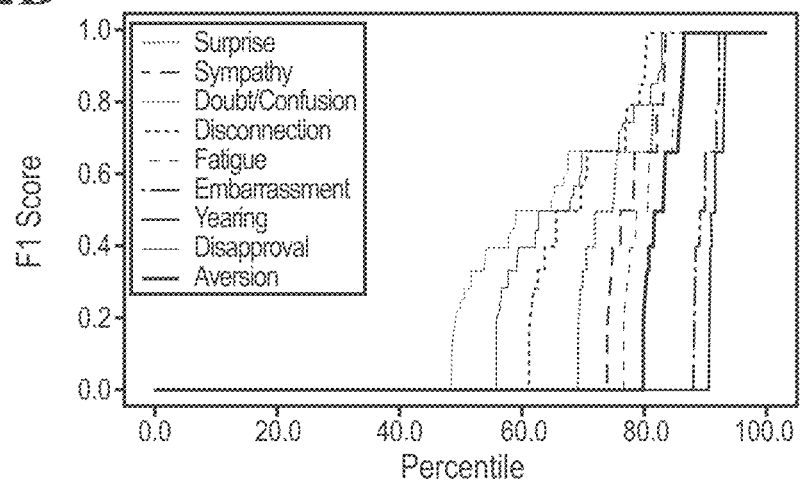
FIG. 12C ions executable by the processor to: receive a plurality of body movement models, each body movement model generated based on a crowdsourced body language dataset, calculate at least one evaluation metric for each body movement model, select a highest ranked body movement model based on the at least one metric calculated for each body movement model, combine the highest ranked body movement model with at least one other body movement model of the plurality of body movement models, calculate at least one evaluation metric for each combination of body movement models, and determine a highest ranked combination of body movement models to predict a bodily expression of emotion.

In another embodiment, an emotion analysis and recognition system includes an automated recognition of bodily expression of emotion (ARBEE) system having a processor and a memory storing program instructions, the program instructions executable by the processor to: receive a plurality of body movement models, each body movement model generated based on a body language dataset, calculate at least one evaluation metric for each body movement model, select a highest ranked body movement model based on the at least one metric calculated for each body movement model, initialize the highest ranked body movement model with one or more pre-trained model, calculate at least one evaluation metric for each initialized body movement model, combine the highest ranked initialized body movement model with at least one other body movement model of the plurality of body movement models, the at least one other body movement model including one or more other initialized body movement models, calculate at least one evaluation metric for each combination of body movement models, and determine a highest ranked combination of body movement models to predict a bodily expression of emotion.

In yet another embodiment, an emotion analysis and recognition method includes: receiving, by an automated recognition of bodily expression of emotion (ARBEE) system, a plurality of body movement models, each body movement model generated based on a crowdsourced body language dataset, calculating, by the ARBEE system, at least one evaluation metric for each body movement model, selecting, by the ARBEE system, a highest ranked body movement model based on the at least one metric calculated for each body movement model, combining, by the ARBEE system, the highest ranked body movement model with at least one other body movement model of the plurality of body movement models, calculating, by the ARBEE system, at least one evaluation metric for each combination of body movement models, and determining, by the ARBEE system, a highest ranked combination of body movement models to predict a bodily expression of emotion.

In a further embodiment, an emotion analysis and recognition method includes: receiving, by an automated recognition of bodily expression of emotion (ARBEE) system, a plurality of body movement models, each body movement model generated based on a body language dataset, calculating, by the ARBEE system, at least one evaluation metric for each body movement model, selecting, by the ARBEE system, a highest ranked body movement model based on the at least one metric calculated for each body movement model, initializing, by the ARBEE system, the highest ranked body movement model with one or more pre-trained model, calculating, by the ARBEE system, at least one evaluation metric for each initialized body movement model, combining, by the ARBEE system, the highest ranked initialized body movement model with at least one

SYSTEMS AND METHODS FOR AUTOMATED RECOGNITION OF BODILY EXPRESSION OF EMOTION

CROSS REFERENCE TO RELATED APPLICATION

The present disclosure claims the benefit of priority to U.S. Provisional Application No. 62/870,901, filed Jul. 5, 2019 and entitled "SYSTEMS AND METHODS FOR AUTOMATED RECOGNITION OF BODILY EXPRESSION OF EMOTION," the entire contents of which is incorporated herein in its entirety.

BACKGROUND

Field

The present disclosure generally relates to systems and/or methods for recognizing a subject's expression of emotion based on the subject's bodily expression, and more specifically, to systems and/or methods that generate a computer-based model to predict the subject's expression of emotion based on the subject's bodily movements and/or bodily posture.

Technical Background

Automatic bodily expression recognition has been challenging for machines, from a technical perspective, for numerous reasons. First, it has been difficult to collect a bodily expression dataset with high-quality, reliable annotations. No standard has been established for annotation labels (e.g., correspondence between body movements and bodily expression) and the interpretations or inferences of viewers may be subjective and/or influenced by context, ethnicity, culture, and/or the like. Second, bodily expression is subtle and composite. Body movements are complex. For example, body movements are not only communicative but also functional and/or artistic. Third, an articulated pose may have many degrees of freedom. No standard has been established to accommodate the relatively broader degrees of freedom associated with bodily movements. Furthermore, conventional attempts to detect emotion based on a subject's bodily expression have been unduly constrained (e.g., limited to lab-setting environments with specific backgrounds, a consistent scale, a fixed camera perspective to capture facial features and/or specific body landmarks, controlled poses, and/or the like) and/or rely on specific technologies for information (e.g., motion capture, 3D mapping, and/or the like). Such approaches are rendered impractical when working with real-world (e.g., in-the-wild) video which often include a cluttered background, substantial differences in scale and/or camera perspective, landmarks and/or facial features out of view, uncontrolled poses, or the like. Additionally, it may not be possible to apply further technologies to such real-world video to realize further information. Accordingly, unconstrained systems and/or methods applicable to real-world (e.g., in-the-wild) video are of interest in recognizing emotion based on bodily expression.

SUMMARY

In one embodiment, an emotion analysis and recognition system includes an automated recognition of bodily expression of emotion (ARBEE) system having a processor and a memory storing program instructions, the program instrucother body movement model of the plurality of body movement models, the at least one other body movement model including one or more other initialized body movement models, calculating, by the ARBEE system, at least one evaluation metric for each combination of body movement models, and determining, by the ARBEE system, a highest ranked combination of body movement models to predict a bodily expression of emotion.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, wherein like structure is indicated with like reference numerals and in which:

FIG. 5B depicts an illustrative screenshot of a categorical emotion labeling step of a web-based crowdsourcing data collection process, according to one or more embodiments of the present disclosure;

FIG. 5C depicts an illustrative screenshot of a dimensional emotion and demographic labeling step of a web-based crowdsourcing data collection process, according to one or more embodiments of the present disclosure;

FIG. 5D depicts an illustrative screenshot of a frame range identification step of a web-based crowdsourcing data collection process, according to one or more embodiments of the present disclosure;

FIG. 6O depicts and illustrative screenshot of a high-confidence instance for the categorical emotion of embarrassment, according to one or more embodiments of the present disclosure;

FIG. 6AA depicts and illustrative screenshot of a first quality control instance, according to one or more embodiments of the present disclosure;

FIG. 6BB depicts and illustrative screenshot of a second quality control instance, according to one or more embodiments of the present disclosure;

FIG. 8 depicts a bar chart illustrating distributions for each of the three (3) dimensional emotion ratings, according to one or more embodiments of the present disclosure;

FIG. 9A depicts a pie chart illustrating the distribution of the characters in the BoLD dataset based on gender, according to one or more embodiments of the present disclosure;

FIG. 9B depicts a pie chart illustrating the distribution of the characters in the BoLD dataset based on age, according to one or more embodiments of the present disclosure;

FIG. 9C depicts a pie chart illustrating the distribution of the characters in the BoLD dataset based on ethnicity, according to one or more embodiments of the present disclosure;

FIG. 12A depicts an illustrative F1 score versus participant population percentile plot for categorical emotions including peace, affection, esteem, anticipation, engagement, confidence, happiness, pleasure, and excitement, according to one or more embodiments of the present disclosure;

FIG. 12B depicts an illustrative F1 score versus participant population percentile plot for categorical emotions including surprise, sympathy, doubt/confusion, disconnection, fatigue, embarrassment, yearning, disapproval, and aversion, according to one or more embodiments of the present disclosure;

FIG. 12C depicts an illustrative F1 score versus participant population percentile plot for categorical emotions including annoyance, anger, sensitivity, sadness, disquietment, fear, pain and suffering, according to one or more embodiments of the present disclosure;

DETAILED DESCRIPTION

Figure 1:
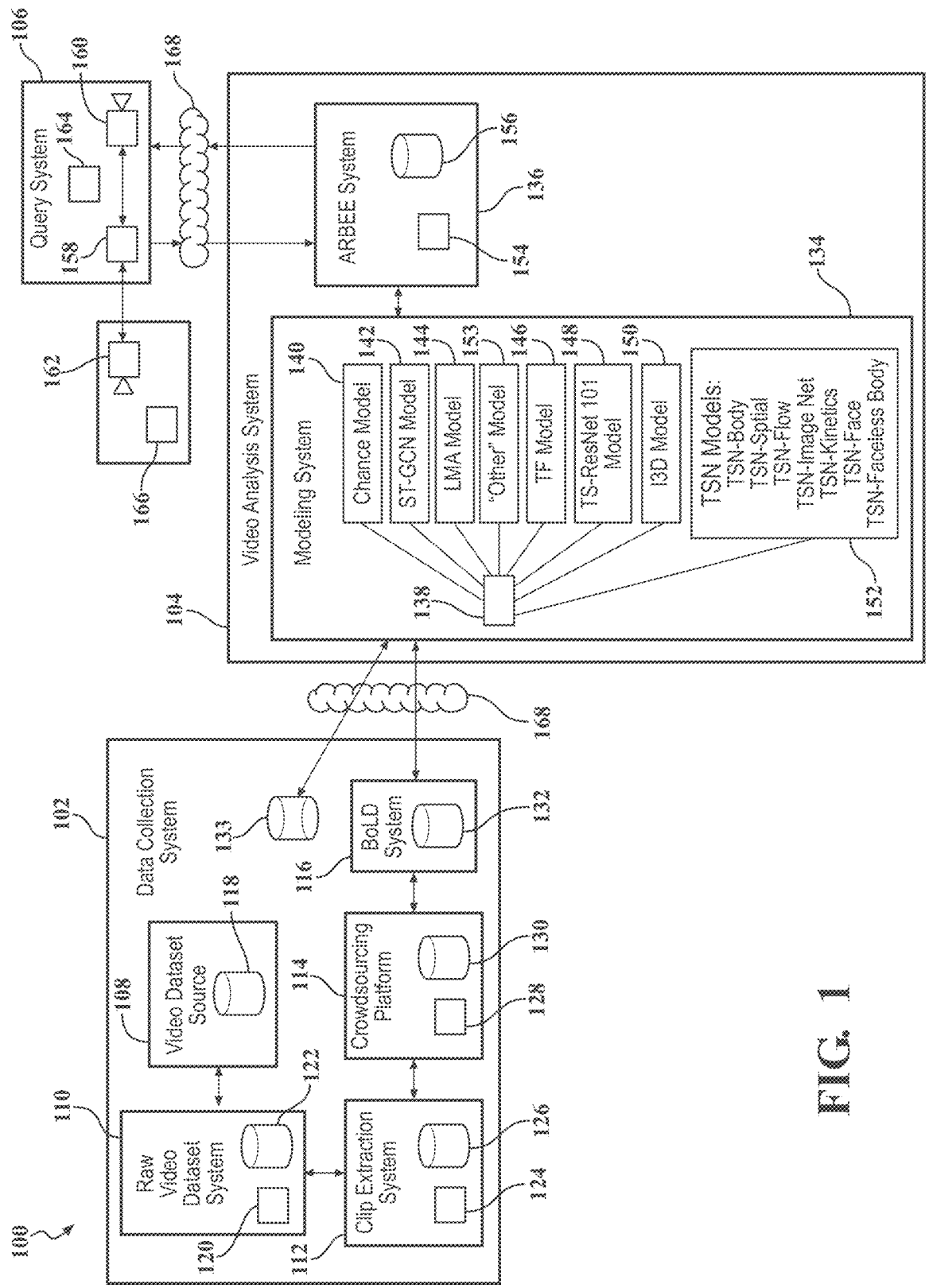
FIG. 1 depicts an illustrative emotion analysis and recognition system, according to one or more embodiments of the present disclosure.

Humans are arguably innately prepared to comprehend others' emotional expressions from subtle body movements. If robots, computers, or other machines can be empowered with this capability, a number of robotic applications become possible. Automatically recognizing human bodily expression in unconstrained situations, however, is daunting given the incomplete understanding of the relationship between emotional expressions and body movements. Various aspects described herein represent a multidisciplinary effort among computer and information sciences, psychology, and statistics, and propose a scalable and reliable crowdsourcing approach for collecting in-the-wild perceived emotion data for computers to learn to recognize body languages of humans. To accomplish this task, a large and growing annotated dataset with 9,876 video clips of body movements and 13,239 human characters, named the Body Language Dataset (hereinafter the "BOLD dataset"), has been created. Comprehensive statistical analysis of the dataset has revealed many interesting insights, as described herein. A system to model the emotional expressions based on bodily movements, named ARBEE (Automated Recognition of Bodily Expression of Emotion), has also been developed and evaluated as described herein. According to various aspects, Laban Movement Analysis (LMA) features are shown as effective in characterizing arousal and experiments using LMA features further demonstrate computability of bodily expression. The results of several other baseline methods, which were developed for action recognition (e.g., versus emotion recognition) based on two different modalities (e.g., body skeleton and raw image), are compared herein. Various aspects described herein advance the understanding of body language. Various aspects described herein may enable robots to interact and collaborate more effectively with humans.

Robotic applications (e.g., personal assistant robots, social robots, police robots, and/or the like) demand close collaboration with and comprehensive understanding of the humans around them. Current robotic technologies for understanding human behaviors beyond their basic activities, however, are limited. Body movements and postures encode rich information about a person's status, including their awareness, intention, and emotional state. Even at a young age, humans can "read" another's body language, decoding movements and facial expressions as emotional keys. Various embodiments of the present disclosure answer the following question: How can a computer program be trained to recognize human emotional expressions from body movements?

Computerized body movement analysis has largely focused on recognizing human activities (e.g., the person is running). Yet, a person's emotional state is another important characteristic that may be conveyed through body movements. Movement and postural behavior may be useful features for identifying human emotions. In one example, human participants could not correctly identify facial expressions associated with winning or losing a point in a professional tennis game when facial images were presented alone, whereas they were able to correctly identify this distinction with images of just the body or images that included both the body and the face. More interestingly, when the face part of an image was paired with the body and edited to an opposite situation face (e.g., winning face paired with losing body), people still used the body to identify the outcome. Accordingly, the human body may be more diagnostic than the face in terms of emotion recognition. According to aspects of the present disclosure, bodily expression may be defined as human affect expressed by body movements and/or postures.

Evoked emotions may be computed from visual stimuli using computer vision and machine learning. Aspects of the present disclosure investigate whether bodily expressions are computable. In particular, according to various embodiments, modern computer vision techniques may match the cognitive ability of typical humans in recognizing bodily expressions in-the-wild (e.g., from real-world, unconstrained situations).

Figure 2A:
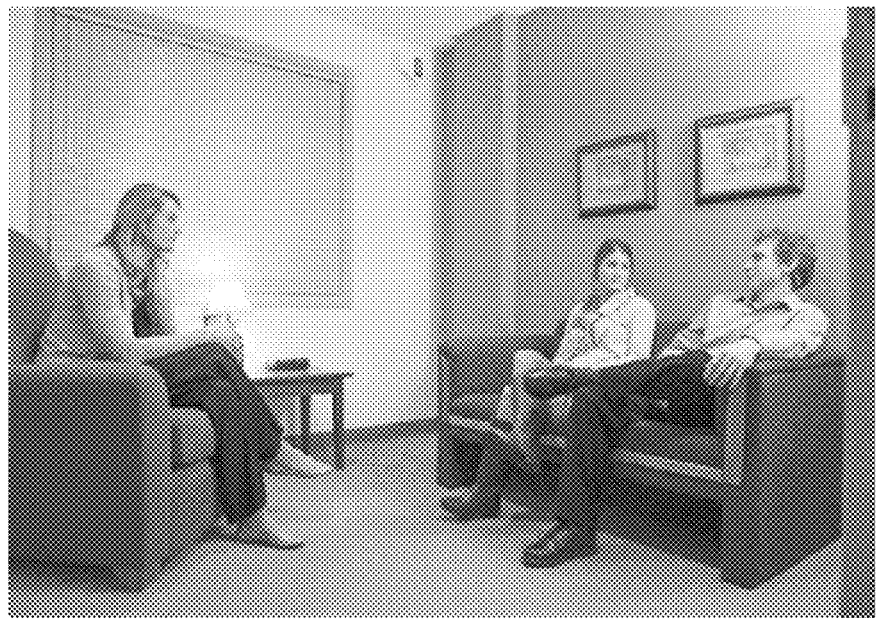
FIG. 2A depicts an illustrative scenario where computerized bodily expression recognition may be applied to assist a psychological clinic, according to one or more embodiments of the present disclosure.
Figure 2B:
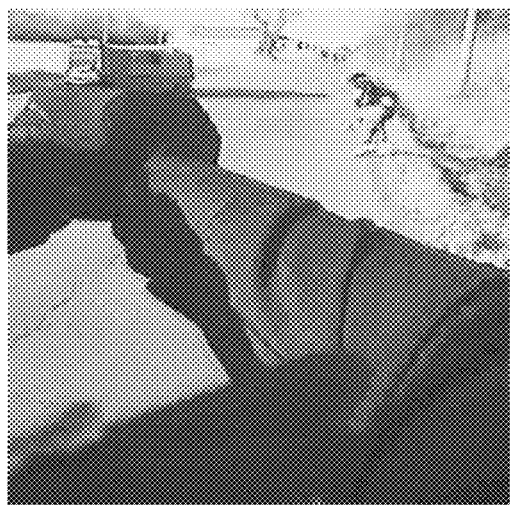
FIG. 2B depicts an illustrative scenario where computerized bodily expression recognition may be applied to assist public safety and law enforcement, according to one or more embodiments of the present disclosure.
Figure 2C:
FIG. 2C depicts an illustrative scenario where computerized bodily expression recognition may be utilized to assist a social robot or social media, according to one or more embodiments of the present disclosure.

Computerized bodily expression recognition capabilities have the potential to support a large number of innovative applications (e.g., information management and retrieval, public safety, patient care, social media, and/or the like). FIGS. 2A-2C depict illustrative scenarios to which computerized bodily expression recognition may be applied. In particular, FIG. 2A depicts an illustrative scenario where computerized bodily expression recognition may be applied to assist a psychological clinic. FIG. 2B depicts an illustrative scenario where computerized bodily expression recognition may be applied to assist public safety and law enforcement. FIG. 2C depicts an illustrative scenario where computerized bodily expression recognition may be utilized to assist a social robot or social media. For instance, systems can be deployed in public areas (e.g., airports, metro or bus stations, stadiums, and/or the like) to help police identify potential threats. Better results might be obtained in a population with a high rate of emotional instability. For example, a psychology clinic may install such systems to help assess and evaluate disorders (e.g., anxiety, depression, and/or the like) either to predict danger to self and/or others from patients, or to track the progress of patients over time. In another example, police may use such technology to help assess the identity of suspected criminals in naturalistic settings and/or their emotions and deceptive motives during an interrogation. An effective assistive technology based on emotional understanding, according to aspects described herein, could substantially reduce the stress of police officers as they carry out their work. Improving the bodily expression recognition of assistive robots may enrich human-computer interactions. Assistive robots may better assist those who may suffer emotional stress or mental illness, e.g., assistive robots may detect early warning signals of manic episodes. In social media, social applications such as Snapchat® and Instagram® allow users to upload short clips of self-recorded and edited videos. A crucial analysis from an advertising perspective is to better identify the intention of a specific uploading act by understanding the emotional status of a person in the video. For example, a user who wants to share the memory of traveling with his family would more likely upload a video capturing the best interaction moment filled with joy and happiness. Such an analysis may help companies to better personalize the services or to provide advertisements more effectively for their users (e.g., through showing travel-related products or services as opposed to business-related ones).

Automatic bodily expression recognition, as described herein, is highly challenging for three primary reasons. First, it is difficult to collect a bodily expression dataset with high-quality annotations. The understanding and perception of emotions from concrete observations is often subject to context, interpretation, ethnicity and culture. There is often no gold standard label for emotions, especially for bodily expressions. In facial analysis, the expression could be encoded with movements of individual muscles, a.k.a., Action Units (AU) in a facial action coding system (FACS). No analogous notation system, that directly encodes a correspondence between bodily expression and body movements, has been developed. This lack of empirical guidance leaves professionals without complete agreement about annotating bodily expressions. Accordingly, research on bodily expression has been limited to acted and constrained lab-setting video data, which are usually of small size (e.g., due to lengthy human subject study regulations). Second, bodily expression is subtle and composite. Body movements may have three categories: functional movements (e.g., walking), artistic movements (e.g., dancing), and communicative movements (e.g., gesturing while talking). According to aspects described herein, in a real-world setting (e.g., in-the-wild), bodily expression can be strongly coupled with functional movements. For example, people may represent different emotional states in the same functional movement (e.g., walking). Third, an articulated pose may have many degrees of freedom. Furthermore, working with real-world video data poses additional technical challenges such as the high level of heterogeneity in peoples' behaviors, the highly cluttered background, and the often substantial differences in scale, camera perspective, and pose of the person in the frame.

According to aspects of the present disclosure, the feasibility of crowdsourcing bodily expression data collection is investigated and the computability of bodily expression using the collected data is studied.

Various aspects described herein include a scalable and reliable crowdsourcing pipeline for collecting in-the-wild perceived emotion data. In one example, the crowdsourcing pipeline has been utilized to collect a large dataset (e.g., BoLD dataset) including 9,876 video clips with body movements and over 13,239 human characters. In such an aspect, each video clip in the BoLD dataset has been annotated for emotional expressions as perceived (e.g., interpreted, inferred, and/or the like) by crowdsourced participants. The BoLD dataset is the first large-scale video dataset for bodily emotion in-the-wild.

Further aspects described herein include a comprehensive agreement analysis on the crowdsourced annotations. In such an aspect, results demonstrate the validity of the crowdsourcing data collection pipeline. Human performance on emotion recognition on a large and highly diverse population is also evaluated. Insights found in these analyses are described herein.

Yet further aspects described herein include an investigation of Laban Movement Analysis (LMA) features and action recognition-based methods using the BoLD dataset. According to some aspects, hand acceleration may show a strong correlation with one particular dimension of emotion (e.g., arousal). This result is intuitive. According to other aspects, action recognition-based models may yield promising results. For example, according to various aspects, deep models may achieve remarkable performance on emotion recognition tasks.

According to various aspects described herein, the bodily expression recognition problem is approached with the focus of addressing the first challenge mentioned earlier. Using the proposed data collection pipeline, high quality affect annotation is collected. Computer vision techniques may be able to address the third challenge to a certain extent. To properly address the second challenge, regarding the subtle and composite nature of bodily expression, breakthroughs in computational psychology may be involved. Below, some of the remaining technical difficulties on the bodily expression recognition problem are detailed.

2D/3D pose estimation techniques are limited compared with Motion Capture (MoCap) systems, which rely on placing active or passive optical markers on the subject's body to detect motion, because of two issues.

First, vision-based estimation methods are noisy in terms of the jitter errors. Despite purported high accuracy with respect to pose estimation benchmarks, the criteria used in the pose estimation benchmarks are not designed for aspects of the present disclosure, which demand substantially higher precision of landmark locations. According to aspects of the present disclosure, pose estimation is a first-step in analyzing the relationship between motion and emotion. As such, imprecise 2D/3D pose estimation techniques may result in errors that would only propagate in the crowdsourcing data collection pipeline.

Second, vision-based methods usually address whole-body poses, which have no missing landmarks, and only produce relative coordinates of the landmarks from the pose (e.g., with respect to the barycenter of the human skeleton) instead of the actual coordinates in the physical environment. In-the-wild videos, however, often contain upper-body or partially-occluded poses. Further, the interaction between a human and the environment, such as a lift of the person's barycenter or when the person is pacing between two positions, is often critical for bodily expression recognition. Additional modeling on the environment together with that for the human would be useful in understanding body movement.

In addition to these difficulties faced by the computer vision community broadly, break-throughs in the computation psychology community may also be involved. For instance, conventional end-to-end action recognition methods developed in the computer vision community offer insufficient interpretability of bodily expression. While LMA features, as developed in the present disclosure, have better interpretability than action recognition-based methods, various aspects of the present disclosure include defining or learning comprehensive motion protocols, as a counterpart of FACS for bodily expression, to improve body language interpretation.

Prior to getting into the details of the present disclosure, basic concepts on bodily expression and related datasets as well as related work on crowdsourcing subjective affect annotation and automatic bodily expression modeling are discussed.

1.0 RELATED WORK

1.1 Bodily Expression Recognition

Conventional automated bodily expression recognition techniques build on two theoretical models for representing affective states (e.g., the categorical model and the dimensional model). The categorical model represents affective states into several emotion categories (e.g., six basic emotions: anger, happiness, sadness, surprise, disgust, and fear). However, bodily expression may not be limited to basic emotions. For example, in a data collection pilot study, when participant interpretations were restricted to only basic emotions, the participants provided feedback that they often found none of the basic emotions as suitable for the given video sample. The dimensional model of affective states is the PAD model, which describes an emotion in three dimensions (e.g., pleasure (valence), arousal, and dominance). In the PAD model, valence characterizes the positivity versus negativity of an emotion, while arousal characterizes the level of activation and energy of an emotion, and dominance characterizes the extent of controlling others or surroundings. Most conventional bodily expression-related techniques focus on either a small set of categorical emotions or the two dimensions of valence and arousal of the PAD model. Embodiments of the present disclosure adopt both measurements (e.g., categorical model and dimensional model) in order to acquire complementary emotion annotations.

Based on how emotion is generated, emotions can be categorized into acted or elicited emotions, and spontaneous emotions. Acted emotion refers to actors' performing a certain emotion under given contexts or scenarios. Various conventional methods focused on acted emotions. One example analyzed videos recorded on recruited actors and established bodily emotions as an important modality of emotion recognition. In another example, a human subject's emotion is elicited via interaction with a computer avatar of its operator. In yet another example image stimuli crowdsourced emotion responses. In a further example, natural or authentic emotions have been generated (e.g., body movements are recorded while human subjects play body movement-based video games).

Related work can be categorized based on raw data types (e.g., MoCap data or image/video data). For lab-setting studies, collecting motion capture data is usually feasible. In one example, a dataset with upper body movement video may be recorded in a studio. In another example, image/video data capturing a frontal view of various poses may be used.

In aspects of the present disclosure, humans may perceive and understand emotions from multiple modalities (e.g., face, body language, touch, eye contact, vocal cues, and/or the like). For example, facial expression may be an important modality in emotion recognition. According to various aspects, automated facial expression recognition may be more successful compared with other modalities. First, the discovery of FACS renders facial expression recognition less subjective. Facial expression recognition focuses on Action Unit detection. Second, the face has fewer degrees of freedom compared with the whole body. To address the comparatively broader freedom of bodily movement, a movement notation system may be used to help identify bodily expression. Microexpressions may also be used to identify additional nuances in facial expressions. No vision-based study or dataset, on a complete measurement of natural bodily emotions, exists.

1.2 Crowdsourced Affect Annotation

Crowdsourcing from the Internet as a data collection process has been proposed to collect objective, non-affective data and has been used in the machine-learning community to acquire large-scale ground truth datasets. A school of data quality control methods has been proposed for crowdsourcing. Nevertheless, crowdsourcing affect annotations is highly challenging due to the intertwined subjectivity of affect and uninformative participants. Very few studies acknowledge the limitations and complexity of crowdsourcing affect annotations. Inconsistencies of crowdsourced affective data exists due to at least two factors. The first factor is the possible untrustworthiness of recruited participants due to the discrepancy between the purpose of study (e.g., collecting high quality data) and the incentive for participants (e.g., earning cash rewards). The second factor is the natural variability of humans perceiving others' affective expressions. In one example, personality attributes were crowdsourced. In such an example, although agreements among different participants were analyzed, no quality control was conducted, catering to the two stated factors in the crowdsourcing. In another example, an ad hoc gold standard was used to control annotation quality and each sample in the training set was only annotated once. In yet another example, evoked emotions of stimuli images were crowdsourced. Yet further, a probabilistic model, Gated Latent Beta Allocation (GLBA) has been used to jointly model each worker's reliability and regularity—the two factors contributing to the inconsistent annotations—in order to improve the quality of affective data collected. Various embodiments of the present disclosure, as described herein, utilize the GLBA methodology for its data quality control pipeline since it is applicable for virtually any crowdsourced affective data. One example of GLBA is disclosed in "Probabilistic multigraph modeling for improving the quality of crowdsourced affective data" by Yee et al., of IEEE Transactions on Affective Computing, the entire contents of which is hereby incorporated by reference herein.

1.3 Automatic Modeling of Bodily Expression

Automatic modeling of bodily expression (AMBE) typically includes three steps: human detection, pose estimation and tracking, and representation learning. In such a pipeline, human(s) are detected frame-by-frame in a video and their body landmarks are extracted by a pose estimator. Subsequently, if multiple people appear in the scene, the poses of the same person are associated along all frames. With each person's pose identified and associated across frames, an appropriate feature representation of each person is extracted.

Based on the way data is collected, AMBE methods are divided into video-based and non-video-based. For video-based methods, data are collected from a camera, in the form of color videos. In one example, videos may be collected in a lab setting with a pure-colored background and a fixed-perspective camera. In some aspects, hands and other landmarks may be detected and tracked with simple thresholding and grouping of pixels. Continuing the example, motion protocols, such as whether the hand is facing up, may be defined and combined with landmark displacement as features. In another example, the positions of shoulders in the image frame, facial expression, and audio features may be used as the input of a neural network. However, according to aspects of the present disclosure, data is not collected under such controlled settings. Accordingly, data collected according to aspects of the present disclosure, as described herein, has variations in viewpoint, lighting condition, scale, and/or the like.

For non-video-based methods, locations of body markers may be inferred by a MoCap system. The first two steps (e.g., human detection, and pose estimation and tracking) are solved directly by the MoCap system. In some aspects, geometric features, such as velocity, acceleration, and orientation of body landmarks, as well as motion protocols may be developed and used to build predictive models.

Human behavior understanding (a.k.a. action recognition), is related to AMBE. In one example, large-scale annotated video datasets and deep learning may be used for action recognition. In another example, two-stream ConvNets-based models may be used. In such an example, two networks with an image input stream and an optical flow input stream characterize appearance and motion, respectively and each stream of ConvNet learns human-action-related features in an end-to-end fashion. In some aspects, human pose information may be used. For example, human skeleton sequences may be modeled using a spatiotemporal graph convolutional network (STG-CN). In another example, pose information may be leveraged using a multitask-learning approach. According to aspects of the present disclosure, as described herein, LMA features are extracted based on skeletons and are used to build predictive models.

Prior to getting into functional details of the present disclosure, an illustrative system architecture that enables the features and functionalities described herein is provided. FIG. 1 depicts an illustrative emotion analysis and recognition system 100, according to one or more embodiments of the present disclosure. Referring to FIG. 1, the emotion analysis and recognition system 100 may include a data collection system 102, a video analysis system 104, and a query system 106. Each system may include one or more component including a non-transitory computer-readable medium for completing the various features and/or functionalities described herein, embodied as hardware, software, and/or firmware, according to aspects shown and described herein. According to some aspects, each component may be configured as a general purpose computer with the requisite hardware, software and/or firmware. According to other aspects, each component may be configured as a special purpose computer (e.g., a particular machine) designed specifically to perform the features and/or functionalities as described herein. Here, it should be generally understood that each component may be one computing device or system or a plurality of computing devices or systems. Each system may include a processor, input/output hardware, network interface hardware, a data storage component (e.g., see FIG. 1) and a memory component configured as volatile or non-volatile memory including RAM (e.g., SRAM, DRAM, and/or other types of random access memory), flash memory, registers, compact discs (CDs), digital versatile discs (DVD), and/or other types of storage components. The memory component may include operating logic or program instructions that, when executed, perform the features and/or functionalities described herein. The processor may include any processing component configured to receive and execute instructions (e.g., operating logic or program instructions from the data storage component and/or memory component) to perform the features and/or functionalities described herein. Network interface hardware may include any wired/wireless hardware generally known to those of skill in the art for communicating with other networks and/or devices.

Turning to FIG. 1, the data collection system 102 of the emotion analysis and recognition system 100 may include a video dataset source 108, a raw video dataset system 110, a clip extraction system 112, a crowdsourcing platform 114, and/or a Body Language Dataset (BoLD) System 116.

The video dataset source 108 may be any video source (e.g., a private video source, a public video source, such as the Atomic Visual Actions (AVA) dataset, a video source internal or external to the data collection system 102, and/or the like) and may include a raw video database 118 that stores its video files (e.g., in-the-wild videos) with respective unique video identifiers.

The raw video dataset system 110, communicatively coupled to the video dataset source 108, may include a raw video application 120 programmed to select a plurality of videos of the video dataset source 108 for analysis. According to various aspects, the raw video application 120 may institute a set of predetermined selection criteria (e.g., threshold video quality, duration, filter for in-the-wild videos, clear perspective, and/or the like). Raw videos selected by the raw video dataset system 110 may be stored in one or more list in the raw video system database 122.

The clip extraction system 112, communicatively coupled to the raw video dataset system 110, may include a clip extraction application 124 programmed to retrieve selected videos, to partition each selected video into scenes, to estimate poses, to identify actors within each scene and/or between scenes, and/or the like. With respect to retrieving selected videos, the clip extraction application 124 may be programmed to access a list of selected videos stored in the raw video system database 122 and to crawl a source (e.g., video dataset source 108, the Internet, YouTube®, and/or the like) for each listed video (e.g. by an associated unique video identifier). With respect to partitioning each selected video into scenes, estimating poses, and/or identifying actors within a scene or scenes, the clip extraction algorithm 124 may be programmed to perform such functionalities and other functionalities as described more fully herein (e.g., partition algorithm, pose estimation algorithm, ID algorithm, and/or the like). Extracted video clips (e.g., as processed by the clip extraction system) may be stored in a clip extraction database 126.

The crowdsourcing platform 114, communicatively coupled to the clip extraction system 112, may include a crowdsourcing application 128 programmed to provide, support and/or generate a crowdsourcing website, to present video clips, to receive annotations (e.g., perceived categorical emotions and perceived dimensional emotions), and to perform quality control tasks. The crowdsourcing application 128 may be programmed to access the extracted video clips stored in the clip extraction database 126 for presentation to crowdsource participants. With respect to providing the crowdsourcing website, presenting the video clips, receiving the annotations, and/or performing the quality control tasks, the crowdsourcing application 128 may be programmed to perform such functionalities and other functionalities as described more fully herein. Data (e.g., raw, calculated metrics, and/or the like) associated with such functionalities may be stored in a crowdsourcing platform database 130.

The BoLD system 116, communicatively coupled to the crowdsourcing platform 114, may store all data collection system 102 results. According to various aspects, a BoLD system database 132 may store each video clip in association with its determined annotation(s) (e.g., the BoLD dataset) as described more fully herein.

Referring still to FIG. 1, the video analysis system 104 of the emotion analysis and recognition system 100 may include a modeling system 134 and an Automated Recognition of Bodily Expression of Emotion (ARBEE) system 136.

The modeling system 134 may include a modeling application 138 programmed to derive a plurality of models based on results stored in the BoLD system database 132. The modeling application 138 may be programmed to retrieve the results stored in the BoLD system database 132. According to some aspects, communications between the BoLD system database 132 of the data collection system 102 and the modeling system 134 of the video analysis system 104 may occur over a network infrastructure 168 (e.g., the Internet, Ethernet, WAN, WPAN, and/or the like). According to various aspects, the modeling application 138 may include a plurality of modeling applications or modules (e.g., one for each illustrated model). In view of FIG. 1, the plurality of models may include a Chance Model 140, a Spatial Temporal Graph Convolutional Network (ST-GCN) Model 142, a Laban Movement Analysis (LMA) Model 144, a Trajectory-Based Activity Features (TF) Model 146, a Two-Stream Network-Based Deep-Learning Method with 101-layer Residual Network (TS-ResNet 101) Model 148, a Two-Stream Inflated 3D Convolution Network (I3D) Model 150, a Two-Stream Temporal Segment Network (TSN) Model 152, an "Other" Model 153, and/or the like. In such aspects, the modeling application 138 (e.g., or the plurality of modeling applications or modules) may be programmed to derive such respective models based on results retrieved from the BoLD system database 132 and other functionalities as described more fully herein. For example, with respect to the LMA model 144, the modeling application 138 may be further programmed to estimate a 2D pose, to determine a normalized pose, to determine a distance between specified joints, to compute velocity, acceleration and jerk of specified joints, to compute angles angular velocity, and angular acceleration between pairs of limbs, to apply a random forest model, and/or other functionalities as described more fully herein. With respect to the TSN Model 152, the modeling application 138 may be further programmed to derive the TSN Model using different pre-trained models (e.g., TSN-Body, TSN-Spatial, TSN-Flow, TSN-Image Net, TSN-Kinetics, TSN-Face, TSN-Faceless Body, and/or the like) as described more fully herein.

The "Other" Model 153, according to various aspects described herein, may include not only a further model based on and/or derived from bodily movement but also a model based on and/or derived from one or more than one modality other than bodily movement (e.g., other cues for interpreting or understanding emotion). For example, in a real-world application, emotion may be perceived and/or understood from one or more than one other modality (e.g., face, touch, eye contact, a vocal cue, and/or the like). Accordingly, in various aspects, the 'Other" Model 153 may include a model based on and/or derived from a modality including one or more than one of face (e.g., facial expression), touch, eye contact, a vocal cue, and/or the like. In such aspects, the modeling application 138 of the modeling system 134 may be further programmed to derive the "Other" Model 153 based on results stored in the BoLD system database 132, data received (e.g., via network infrastructure 168) from another data source 133 (e.g., FACS, and/or the like). According to various aspects, the data source 133 may be part of or separate from (e.g., external to) the data collection system 102.

The ARBEE system 136 may include an ensemble application 154 programmed to select and combine two or more of the plurality of models derived by the modeling system 134 to establish and improve the predictive ability and/or performance of the ARBEE system 136 (e.g., in determining an emotion and/or performing an emotion state analysis). The ensemble application 154 may be programmed to evaluate the predictive ability and/or performance of each model and/or combination of models. In particular, the ensemble application 154 may be programmed to compute various evaluation metrics. Evaluation metrics may include average precision (AP, e.g., area under a precision recall curve) and/or receiver operating characteristic (ROC AUC, e.g., area under a receiver operating characteristic curve) to evaluate the classification performance for each categorical emotion, $R^2$ (e.g., coefficient of determination) to evaluate regression performance for each dimensional emotion, as well as, mean average precision (mAP) and mean ROC AUC (mRA) over the categorical emotions and mean $R^2$ ($mR^2$) over the dimensional emotions to compare the performance of the different models, as well as, an emotion recognition score (ERS) to compare the performance of the different methods, as well as other metrics, as described more fully herein. Data (e.g., evaluation and/or performance metrics, and/or the like) associated with such combined models may be stored in an ARBEE database 156. Yet further, the ensemble application 154 may be programmed to, based on the evaluation metrics, select and combine high predictive and/or high performing models (e.g., highest ranked based on calculated evaluation metrics). Still further, the ensemble application 154 may be programmed to, in response to receipt of a video (e.g., static video clip, live feed, and/or the like), apply the video as input to its best performing model (e.g., single model or combined model) and to transmit (e.g., to a querying system) an emotion result (e.g., predicted emotion and/or emotion state analysis). The ensemble application 154 may be further programmed to perform other functionalities as described more fully herein.

Still referring to FIG. 1, the query system 106 of the emotion analysis and recognition system 100 may include a query application 158 programmed to receive a video (e.g., a static video clip, a live feed, and/or the like) from an internal source 160 and/or an external source 162 (e.g., a video camera, database and/or the like) of the query system 106. The query application 158 may be further programmed to transmit a received video to the ARBEE system 136 and to receive a response from the ARBEE system 136. According to various aspects, the response from the ARBEE system 136 may include a predicted emotion and/or emotion state analysis corresponding to each video received from the query system 106. The query application 158 may be yet further programmed to present the response to a user via an internal output device 164 or an external output device 166 (e.g., a display screen, a GUI, and/or the like) of the query system 106. The query application 158 may be still further programmed to perform other functionalities as described more fully herein. According to some aspects, communications between the query system 106 and the ARBEE system 136 of the video analysis system 105 may occur over a network infrastructure 168 (e.g., the Internet, Ethernet, WAN, WPAN, and/or the like). According to various aspects, the query system 106 may include a robot (e.g., assistant robot, social robot, police robot, and/or the like), a computer, or the like.

According to various aspects of the present disclosure, the data collection system 102 and/or components thereof, the video analysis system 104 and/or components thereof, and/or the query system 106 and/or components thereof may be combined into one system without departing from the spirit and scope of the present disclosure. Furthermore, it should be appreciated that the emotion analysis and recognition system 100 may include more systems than those described herein or fewer systems than those described herein. Furthermore, the features and functionalities described herein may be alternatively distributed amongst such systems.

Benefits described herein include a system flexibly applicable to any real-world situation (e.g., system models based on crowdsourced-derived underlying in-the-wild data, useful for day-to-day scenarios), usable indoors and/or outdoors (e.g., system based on body movements, joints, connectivity of joints and/or the like and not constrained with respect to background or environment), with or without a full body view (e.g., system is based on what is seen, not what is not seen), regardless of whether a subject's face is visible (e.g., not dependent on FACS), and without a need for depth (e.g., uses 2D versus 3D) and/or motion capture systems (e.g., Kinect, MoCap, and/or the like)

2.0 THE BODY LANGUAGE DATASET (BOLD)

2.1 Dataset Construction

Figure 3:
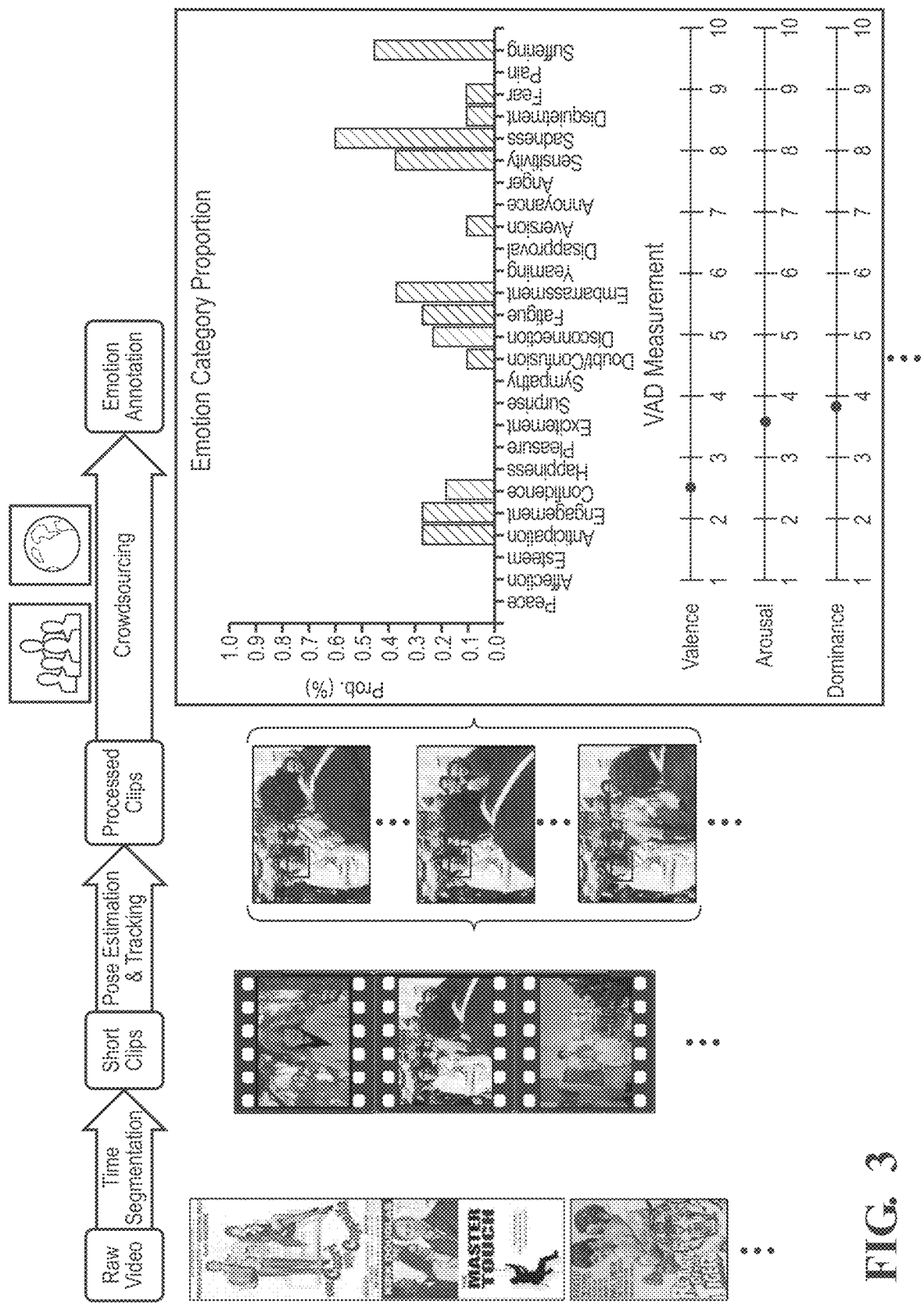
FIG. 3 depicts a flow diagram of an illustrative data collection pipeline, according to one or more embodiments of the present disclosure.

The dataset construction process, detailed below, consists of three stages: movie selection and time segmentation, pose estimation and tracking, and emotion annotation. FIG. 3 depicts a flow diagram of an illustrative data construction pipeline, according to one or more embodiments of the present disclosure. According to aspects of the present disclosure, movies were chosen from those included in a public dataset (e.g., the AVA dataset, which contains a list of YouTube® movie IDs). To respect the copyright of the movies, each movie ID is provided in the same way as in the AVA dataset. According to aspects of the present disclosure, each raw movie crawled from YouTube®, was first partitioned into several short scenes (e.g., clips) before using other vision-based methods to locate and track each person across different frames in the scene. To facilitate tracking, the same person in each clip was marked with a unique ID number. Finally, according to aspects of the present disclosure, emotion annotations of each person in these ID-marked clips were obtained by employing independent contractors (to be called participants hereafter) from an online crowdsourcing platform (e.g., the Amazon Mechanical Turk (AMT)).

2.1.1 Movie Selection and Time Segmentation

The Internet has vast natural human-to-human interaction videos, which serves as a rich source for the data. A large collection of video clips from daily lives is an ideal dataset for developing affective recognition capabilities because they match closely with common real-world situations. However, a majority of such user-uploaded, in-the-wild videos suffer from poor camera perspectives and may not cover a variety of emotions. According to aspects of the present disclosure, it is beneficial to use movies and TV shows (e.g., reality shows, uploaded videos in social media, and/or the like) that are unconstrained but offer highly interactive and emotional content. Such movies and TV shows are typically of high quality in terms of filming techniques and the richness of plots. Such shows are thus more representative in reflecting characters' emotional states than some other categories of videos (e.g., DIY instructional videos, news event videos, and or the like).

According to an embodiment of the present disclosure, 150 movies (220 hours in total) were crawled from YouTube® by the video IDs curated in the AVA dataset.

Movies are typically filmed so that shots in one scene demonstrate characters' specific activities, verbal communication, and/or emotions. According to aspects of the present disclosure, to make these videos manageable for further human annotation, each video is partitioned into short video clips using the kernel temporal segmentation (KTS) method. For example, the KTS method is disclosed in "Category-Specific Video Summarization" by Potapov et al., of European Conference on Computer Vision, the entire contents of which is hereby incorporated by reference herein. In such aspects, KTS detects shot boundary by keeping variance of visual descriptors within a temporal segment small. A shot boundary can be either a change of scene or a change of camera perspective within the same scene (both cases referenced as "scene" hereinafter).

2.1.2 Pose Estimation and Tracking

Figure 4:
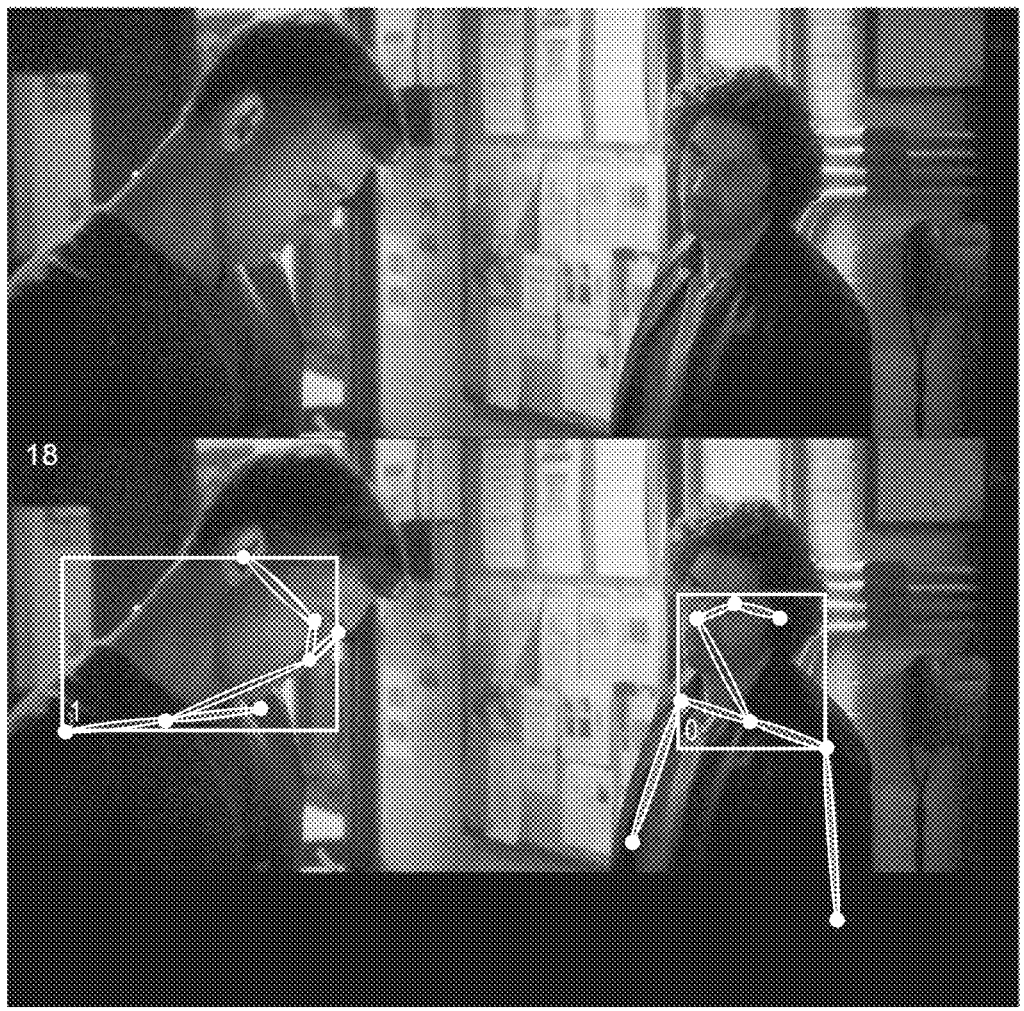
FIG. 4 depicts an illustrative frame in a video clip, where different characters are numbered with an ID and body and/or facial landmarks are detected, according to one or more embodiments of the present disclosure.

An approach to detect human body landmarks and track each character at the same time was adopted. FIG. 4 depicts an illustrative frame in a video clip, where different characters are numbered with an ID (e.g., 0 and 1 at the bottom left corner of red bounding boxes) and body and/or facial landmarks are detected (indicated with stick figures), according to one or more embodiments of the present disclosure. Because not all short clips contain human characters, such clips without humans were removed via pose estimation. According to various aspects, each clip may be processed by a pose estimator (e.g., "caffe_rtpose" by CMU-Perceptual_Computing Lab, See "Realtime Multi-Person 2D Pose Estimation using Part Affinity Fields" by Zhe Cao, Tomaas Simon, Shih-En Wei, and Yaser Sheikh, the entire contents of which is hereby incorporated by reference herein) frame-by-frame to acquire human body landmarks. Different characters in one clip correspond to different samples. Each character in the clip is marked as a different sample. To make the correspondence clear, each character is tracked and designated with a unique ID number. Specifically, tracking was conducted on the upper-body bounding box with a Kalman Filter and Hungarian algorithm as the key component (e.g., "sort" by abewley, See "Simply Online and Realtime Tracking" by Alex Bewley, Zongyuan Ge, Lionel Ott, Fabio Ramos, and Ben Uperoft, the entire contents of which is hereby incorporated by reference herein). In the implementation, the upper-body bounding box was acquired with the landmarks on face and shoulders. Empirically, to ensure reliable tracking results when presenting to the annotators, short trajectories that had less than 80% of the total frames were removed.

2.1.3 Emotion Annotation

Following the above steps, 122,129 short clips were generated from the movies. Facial close-up clips were removed using results from pose estimation. Concretely, a clip was included in the annotation list if the character in it has at least three visible landmarks out of the six upper-body landmarks (e.g., left wrist, right wrist, left elbow, right elbow, left shoulder, right shoulder). Those clips with between 100 and 300 frames were selected for manual annotation by the participants. An identified character with landmark tracking in a single clip is called an instance. A total of 48,037 instances were curated for annotation from a total of 26,164 video clips.

The AMT was used for crowdsourcing emotion annotations of the 48,037 instances. For each Human Intelligence Task (HIT), a human participant completes emotion annotation assignments for 20 different instances. Each of which was drawn randomly from the instance pool. Each instance is expected to be annotated by five different participants.

Figure 5A:
FIG. 5A depicts an illustrative screenshot of a video data quality check step of a web-based crowdsourcing data collection process, according to one or more embodiments of the present disclosure.
Figure 5C:
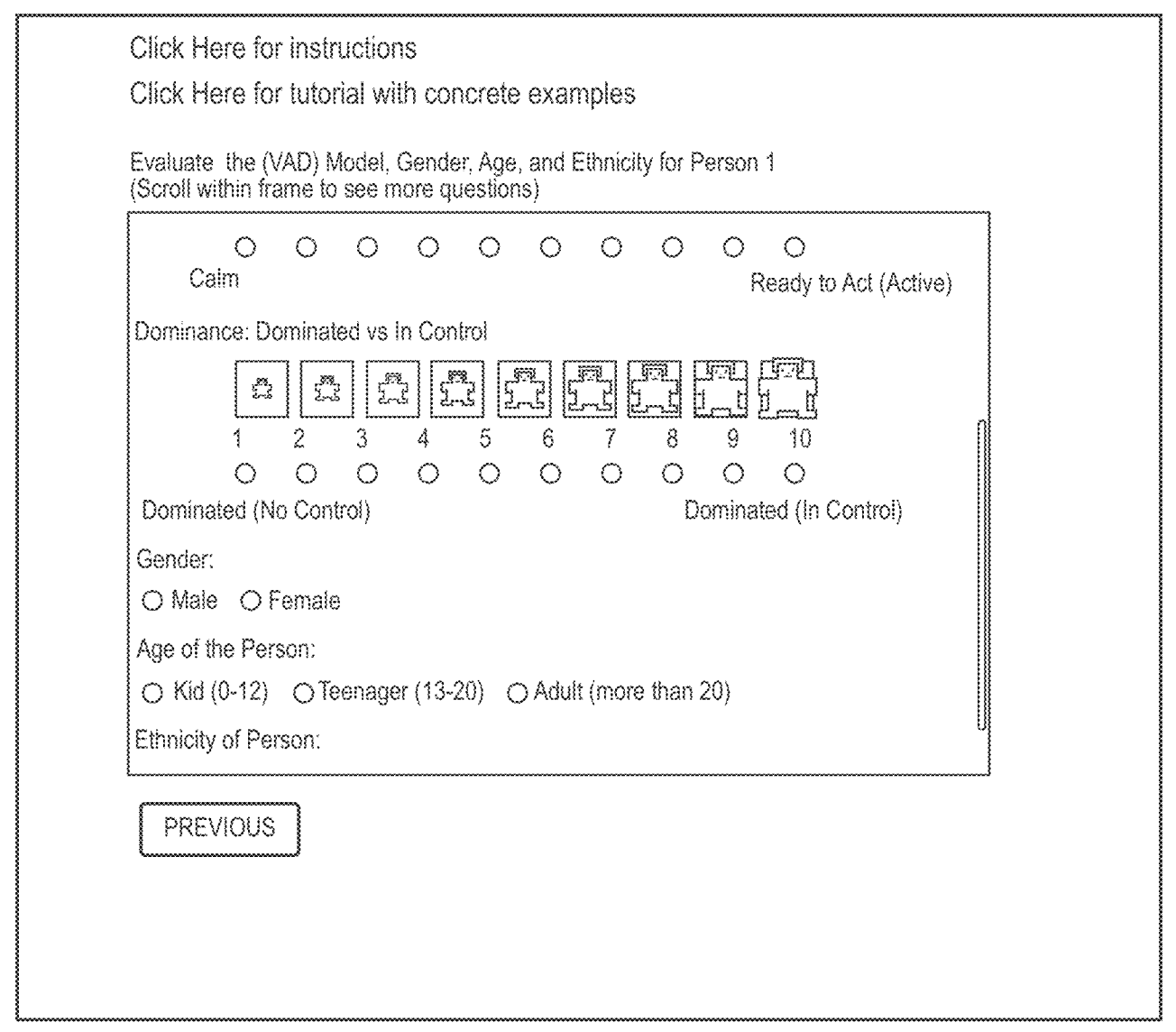

Human annotators were asked to finish the annotation tasks per instance. FIGS. 5A-5D show screenshots of the crowdsourcing website design. For each video clip, participants are directed to go through a sequence of screens with questions step-by-step. FIG. 5A depicts an illustrative screenshot of a video data quality check step of a web-based crowdsourcing data collection process, according to one or more embodiments of the present disclosure. As a first step, participants must check if the instance is corrupted. An instance is considered corrupted if landmark tracking of the character is not consistent or the scene is not realistic in daily life (e.g., such as science fiction scenes). If an instance is not corrupted, participants are asked to annotate the character's emotional expressions according to both categorical emotions and dimensional emotions (valence, arousal, dominance (VAD) in the dimensional emotion state model). FIG. 5B depicts an illustrative screenshot of a categorical emotion labeling step of a web-based crowdsourcing data collection process, according to one or more embodiments of the present disclosure. For categorical emotions, a list including 26 categories (e.g., peace, affection, esteem, anticipation, engagement, confidence, happiness, pleasure, excitement, surprise, sympathy, doubt/confusion, disconnection, fatigue, embarrassment, yearning, disapproval, aversion, annoyance, anger, sensitivity, sadness, disquietment, fear, pain, suffering) was used as a superset of the six basic emotions (e.g., anger, happiness, sadness, surprise, disgust, and fear). Participants are asked to annotate these categories in the way of multi-label binary classifications. FIG. 5C depicts an illustrative screenshot of a dimensional emotion and demographic labeling step of a web-based crowdsourcing data collection process, according to one or more embodiments of the present disclosure. For each dimensional emotion, integers that scale from 1 to 10 were used. These annotation tasks are meant to reflect the truth revealed in the visual and audio data—movie characters' emotional expressions—and do not involve the participants emotional feelings. Characters' and participants' demo-graphic information (gender, age, and ethnicity) is also annotated/collected for complementary analysis. Gender categories are male and female. Age categories are defined as kid (aged up to 12 years), teenager (aged 13-20), and adult (aged over 20). Ethnicity categories are American Indian or Alaska Native, Asian, African American, Hispanic or Latino, Native Hawaiian or Other Pacific Islander, White, and Other. In addition to these tasks, participants are asked to specify a time interval (e.g., the start and end frames) over the clip that best represents the selected emotion(s) or has led to their annotation. FIG. 5D depicts an illustrative screenshot of a frame range identification step of a web-based crowdsourcing data collection process, according to one or more embodiments of the present disclosure.

The participants are permitted to hear the audio of the clip, which can include a conversation in English or some other language. While the goal of this research is to study the computability of body language, the participants were allowed to use all sources of information (facial expression, body movements, sound, and limited context) in their annotation in order to obtain as high accuracy as possible in the data collected. Additionally, the participants can play the clip back-and-forth during the entire annotation process for that clip.

To sum up, the annotation of categorical and dimensional emotions, time interval of interest, and character demographic information was crowdsourced.

2.1.4 Annotation Quality Control

Quality control has always been a necessary component for crowdsourcing to identify dishonest participants, but it is much more difficult for affect data. Different people may not perceive affect in the same way, and their understanding may be influenced by their cultural background, current mood, gender, and personal experiences. An honest participant could also be uninformative in affect annotation, and consequently, their annotations can be poor in quality. In the study, the variance in acquiring affects usually comes from two kinds of participants, (e.g., dishonest ones-who give useless annotations for economic motivation, and exotic ones-who give inconsistent annotations compared with others). Note that exotic participants come with the nature of emotion, and annotations from exotic participants could still be useful when aggregating final ground truth or investigating cultural or gender effects of affect. In the crowdsourcing task, it may be desired to reduce the variance caused by dishonest participants.

Gold standard examples may be used in crowdsourcing to identify uninformative participants. This approach involves curating a set of instances with known ground truth and removing those participants who answer incorrectly. For the task, however, this approach is not as feasible as in conventional crowdsourcing tasks such as image object classification. To accommodate subjectivity of affect, gold standard has to be relaxed to a large extent. Consequently, the recall of dishonest participants is lower.

To alleviate the aforementioned dilemma, the complementary mechanisms for quality control were used, including three online approaches (e.g., analyzing while collecting the data) and an offline approach (e.g., post-collection analysis). According to aspects described herein, the online approaches are participant screening, annotation sanity check, and a relaxed gold standard test, respectively, while the offline one is reliability analysis.

With respect to the participant screening approach, first-time participants in the HIT must take a short empathy quotient (EQ) test. One example EQ test is disclosed in "Development of Short Forms of the Empathy Quotient (eq-short) and the Systemizing Quotient (sq-short)" by Wakabayashi et al., of Personality an Individual Differences, the entire contents of which is hereby incorporated by reference herein. Only those who have above-average EQ are qualified. This approach aims to reduce the number of exotic participants from the beginning.

With respect to the annotation sanity check approach, during the annotation process, the system checks consistency between categorical emotion and dimensional emotion annotations as they are entered. For example, an "affection", "esteem", "happiness", or "pleasure" instance may be expected to have an above-midpoint valence score; a "disapproval", "aversion", "annoyance", "anger", "sensitivity", "sadness", "disquietment", "fear", "pain", or "suffering" instance to have a below-midpoint valence score; a "peace" instance to have a below-midpoint arousal score; and an "excitement" instance to have an above-midpoint arousal score. As an example, if a participant chooses "happiness" and a valence rating between 1 and 5 (out of 10) for an instance, the annotation was treated as inconsistent. In each HIT, a participant fails this annotation sanity check if there are two inconsistencies among twenty instances.

With respect to the relaxed gold standard test approach, one control instance (relaxed gold standard) is randomly inserted in each HIT (e.g., substituted for one of the 20 instances randomly assigned for annotation) to monitor the participant's performance. Control instances are collected in the trial run within a small trusted group and choose instances with very high consensus. The acceptable range of each control instance is manually relaxed to avoid false alarm. For example, for an indisputable sad emotion instance, an annotation is accepted if valence is not higher than 6. An annotation that goes beyond the acceptable range is treated as failing the relaxed gold standard test. Nine control clips and their relaxed annotations were selected as the relaxed gold standard. Additional control clips were not used because the average number of completed HITs per participant is much less than nine and the gold standard is rather relaxed and inefficient in terms of recall.

With respect to the reliability analysis, to further reduce the noise introduced by dishonest participants, reliability analysis is conducted over all participants. One example reliability analysis is disclosed in "Probabilistic Multigraph Modeling for Improving the Quality of Crowdsourced Affective Data" by Yee et al., the entire contents of which is incorporated by reference herein. Such an approach may properly handle the intrinsic subjectivity in affective data. Reliability and regularity of participants are jointly modeled. Low-reliability-score participant corresponds to dishonest participant, and low-regularity participant corresponds to exotic participant. This method was originally developed for improving the quality of dimensional annotations based on modeling the agreement multi-graph built from all participants and their annotated instances. For each dimension of VAD, this method estimates participant i's reliability score (e.g., $r_i^v$, $r_i^a$, $r_i^d$). In such an aspect, the valence and arousal dimensions may be empirically meaningful for ranking participants' reliability scores. Therefore, according to aspects of the present disclosure, the reliability score as $r_i=(2r_i^v+r_i^a)/3$ is assembled. Participant i is marked as failing in reliability analysis if $r_i$ is less than ⅓ with enough effective sample size.

Based on these mechanisms, those participants deemed 'dishonest' are restrained. According to various embodiments, after each HIT, participants with low performance are blocked for one hour. According to various aspects of the present disclosure a low-performance participant may include a participant either failing the annotation sanity check or the relaxed gold standard test. According to various aspects, the work is rejected if it shows low performance and fails in the reliability analysis. In addition to such constraints, according to various aspects, participants with a low reliability score may also be permanently excluded from participating in the HITs again.

2.1.5 Annotation Aggregation

Whenever a single set of annotations is needed for a clip, proper aggregation is necessary to obtain a consensus annotation from multiple participants. The Dawid-Skene method, which has been used to combine noisy categorical observations, computes an estimated score (e.g., scaled between 0 and 1) for each instance. The Dawid-Skene method is described in "Maximum Likelihood Estimation of Observer Error-Rates Using the EM Algorithm" by Dawid et al., of Applied Statistics, the entire contents of which is hereby incorporated by reference herein. According to aspects of the present disclosure, the Dawid-Skene method was used to aggregate annotations on each categorical emotion annotation and categorical demographic annotation. Particularly, the notation $s_i^c$ was used to represent the estimated score of the binary categorical variable c for the instance i. A threshold of 0.5 was set for these scores when binary categorical annotation is needed. For dimensional emotion, the set of annotations for a clip was averaged with their annotators' reliability score (e.g., $r_i$). Considering a particular instance, suppose it has received n annotations. The score $s_i^d$ is annotated by participant i with reliability score $r_i$ for dimensional emotion d, where $i \in \{1, 2, \ldots, n\}$ and $d \in \{V, A, D\}$ in the VAD model. The final annotation is then aggregated as:

$$s^d = \frac{\sum_{i=1}^{n} r_i s_i^d}{10 \sum_{i=1}^{n} r_i}. \tag{1}$$

According to various aspects, instance confidence may be defined as $$c = 1 - \prod_{i=1}^{n} (1 - r_i). \tag{2}$$

Note that the final VAD score is divited by 10 so that the data ranges between 0 and 1. The final dataset to be used for further analysis retained only those instances with confidence higher than 0.95.

According to embodiments of the present disclosure, the website sets a default value for the start frame (0) and the end frame (total frame number of the clip) for each instance. Among the data collected, there were about a half annotations that have non-default values, which means a portion of the annotators either considered the whole clip as the basis for their annotations or did not finish the task. For each clip, the time-interval entered by the participant with the highest reliability score is selected as the final annotation for the clip.

2.2 Dataset Statistics

Various statistical techniques were used to validate the quality control mechanisms and thoroughly understand the consensus level of the verified data labels. Because human perceptions of a character's emotions naturally varies across participants, absolute consensus for collected labels may not be expected. In fact, it is nontrivial to quantitatively understand and measure the quality of such affective data.

2.2.1 Annotation Distribution and Observations

Figure 6A:
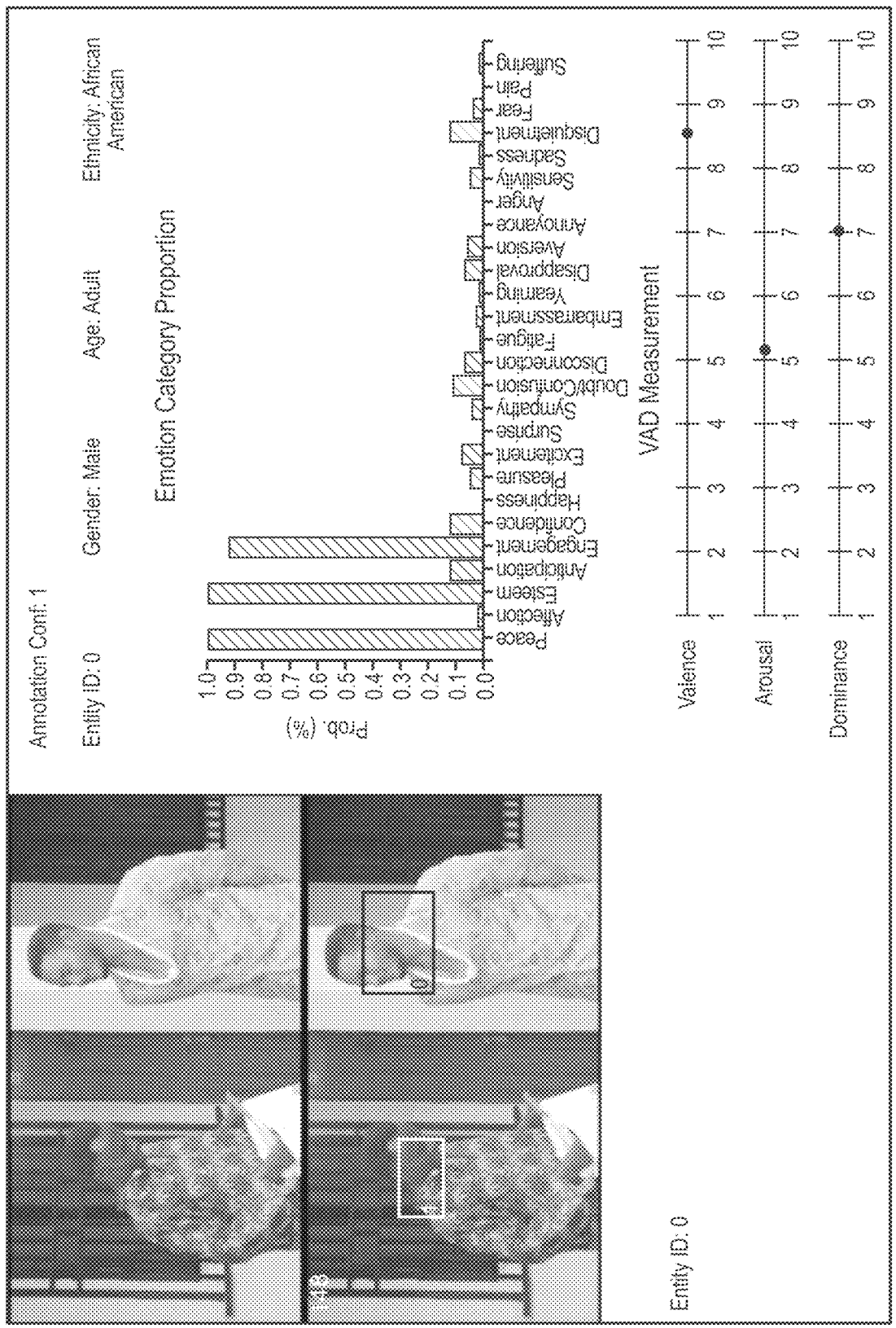
FIG. 6A depicts and illustrative screenshot of a high-confidence instance for the categorical emotion of peace, according to one or more embodiments of the present disclosure.
Figure 6B:
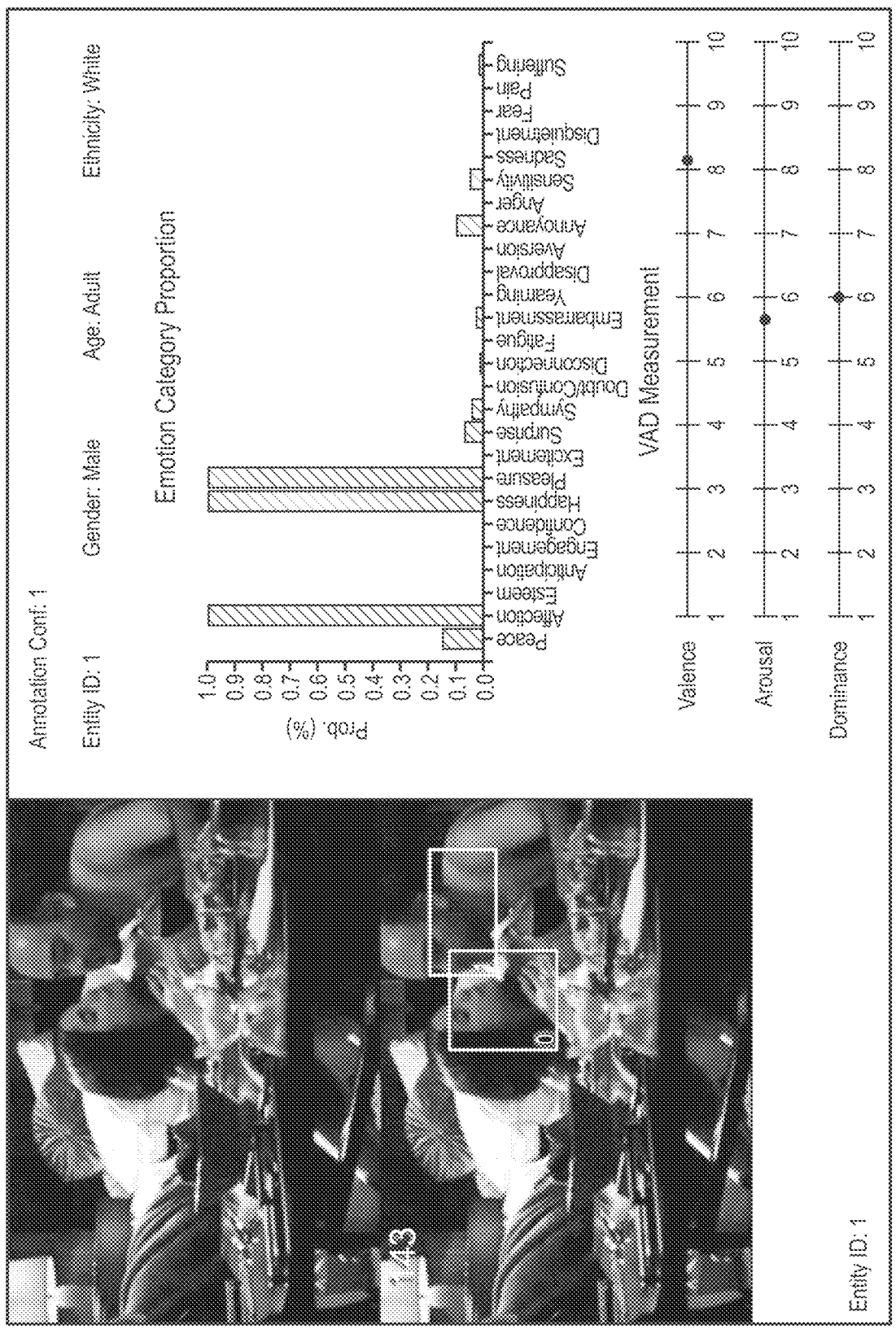
FIG. 6B depicts and illustrative screenshot of a high-confidence instance for the categorical emotion of affection, according to one or more embodiments of the present disclosure.
Figure 6C:
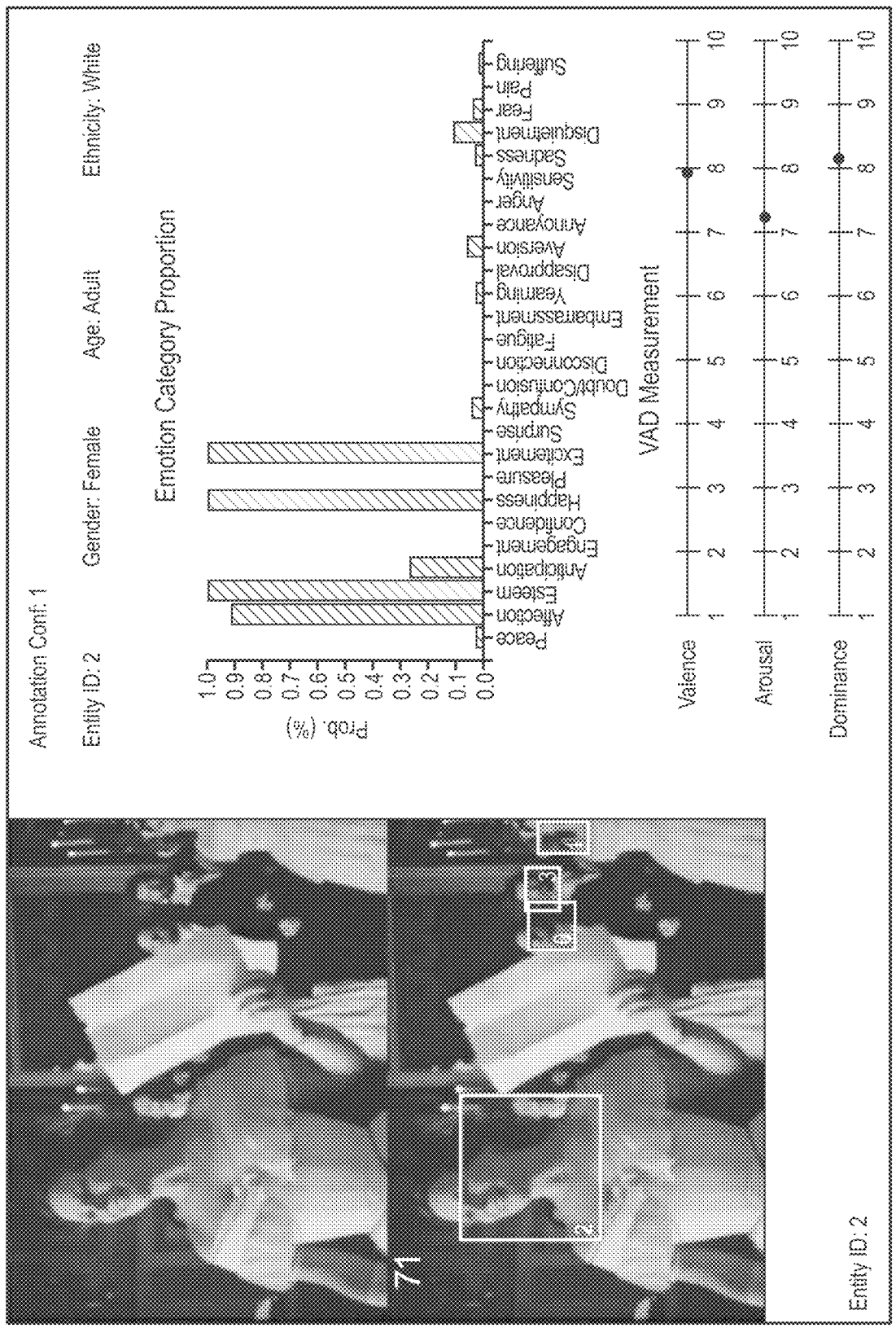
FIG. 6C depicts and illustrative screenshot of a high-confidence instance for the categorical emotion of esteem, according to one or more embodiments of the present disclosure.
Figure 6D:
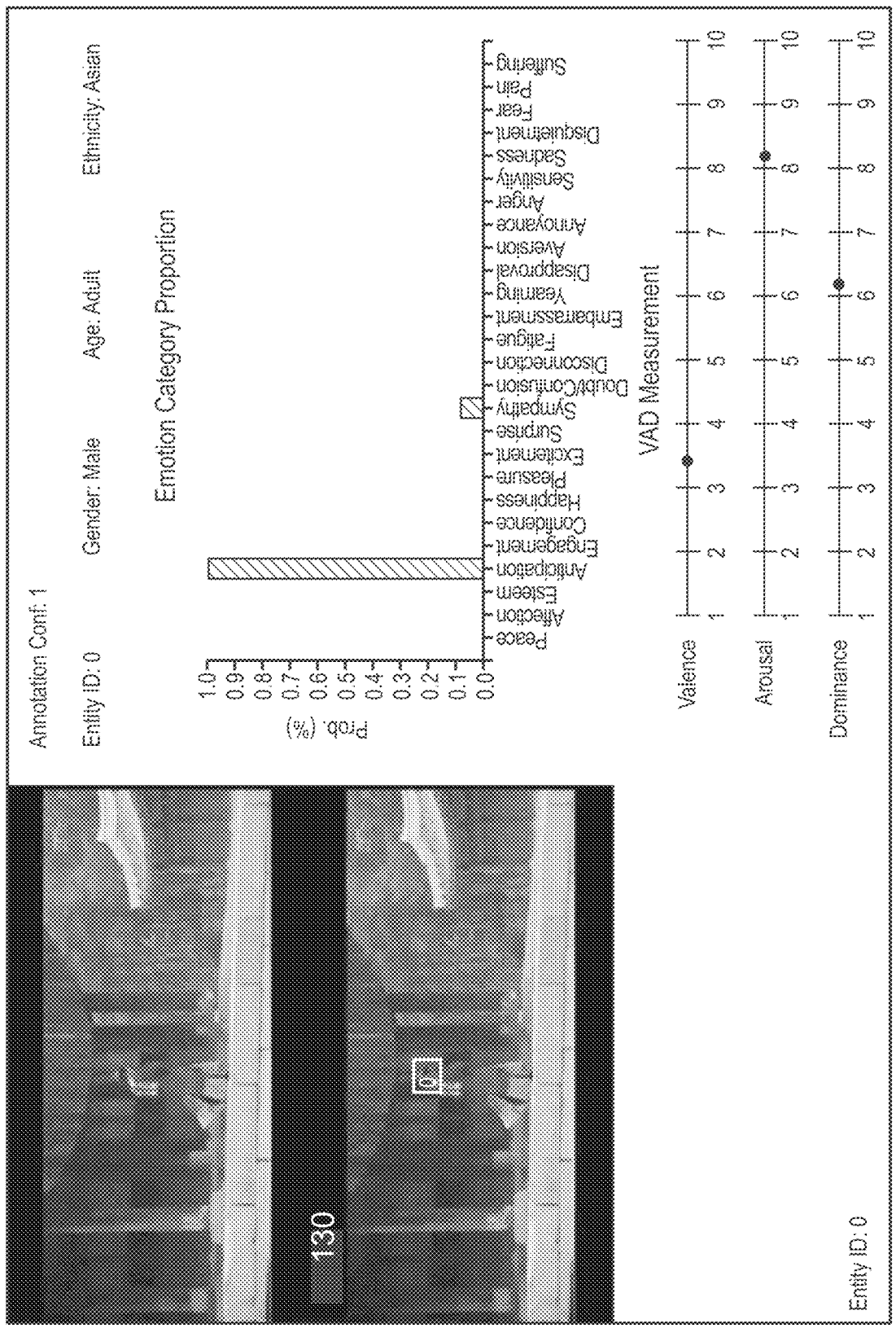
FIG. 6D depicts and illustrative screenshot of a high-confidence instance for the categorical emotion of anticipation, according to one or more embodiments of the present disclosure.
Figure 6E:
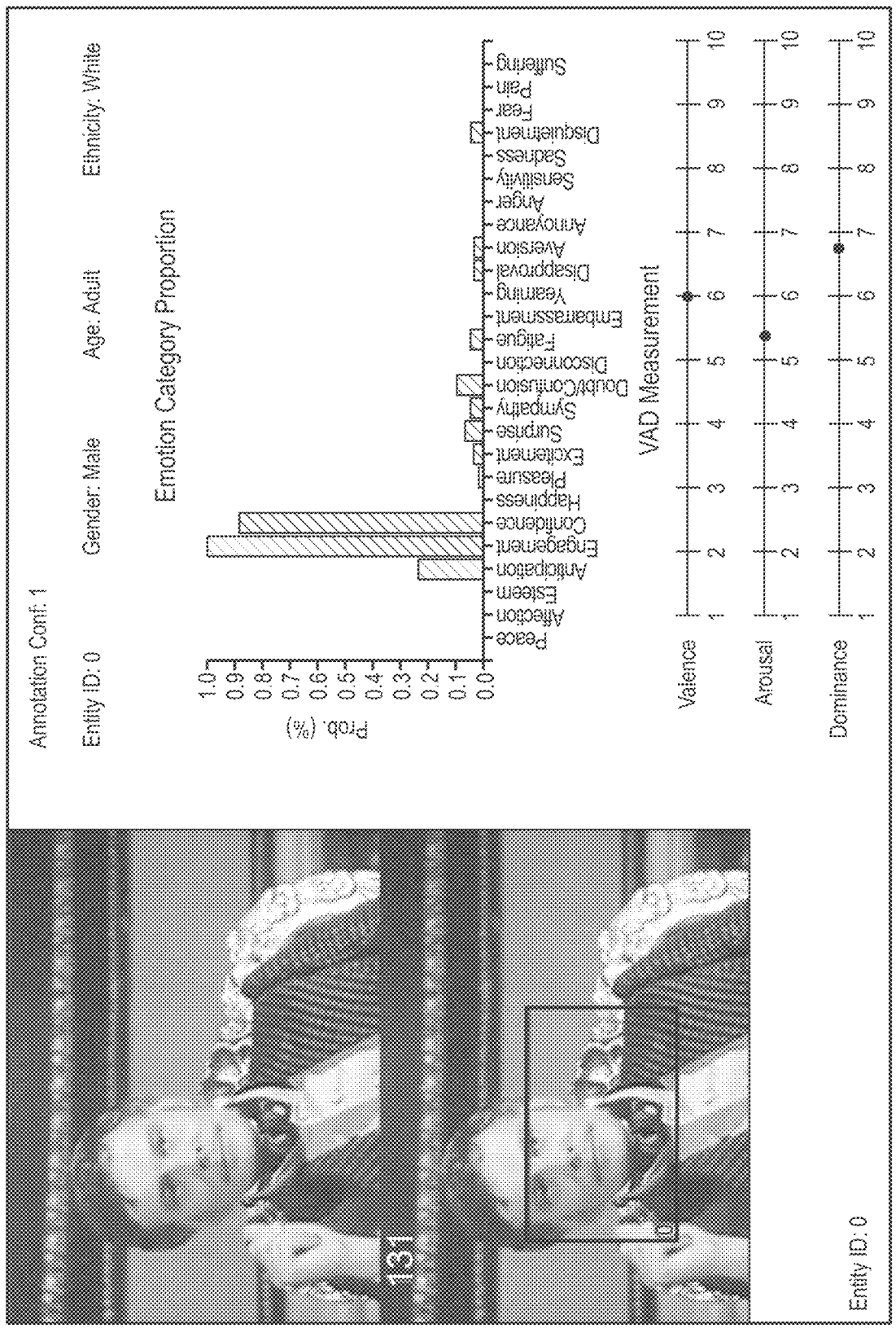
FIG. 6E depicts and illustrative screenshot of a high-confidence instance for the categorical emotion of engagement, according to one or more embodiments of the present disclosure.
Figure 6F:
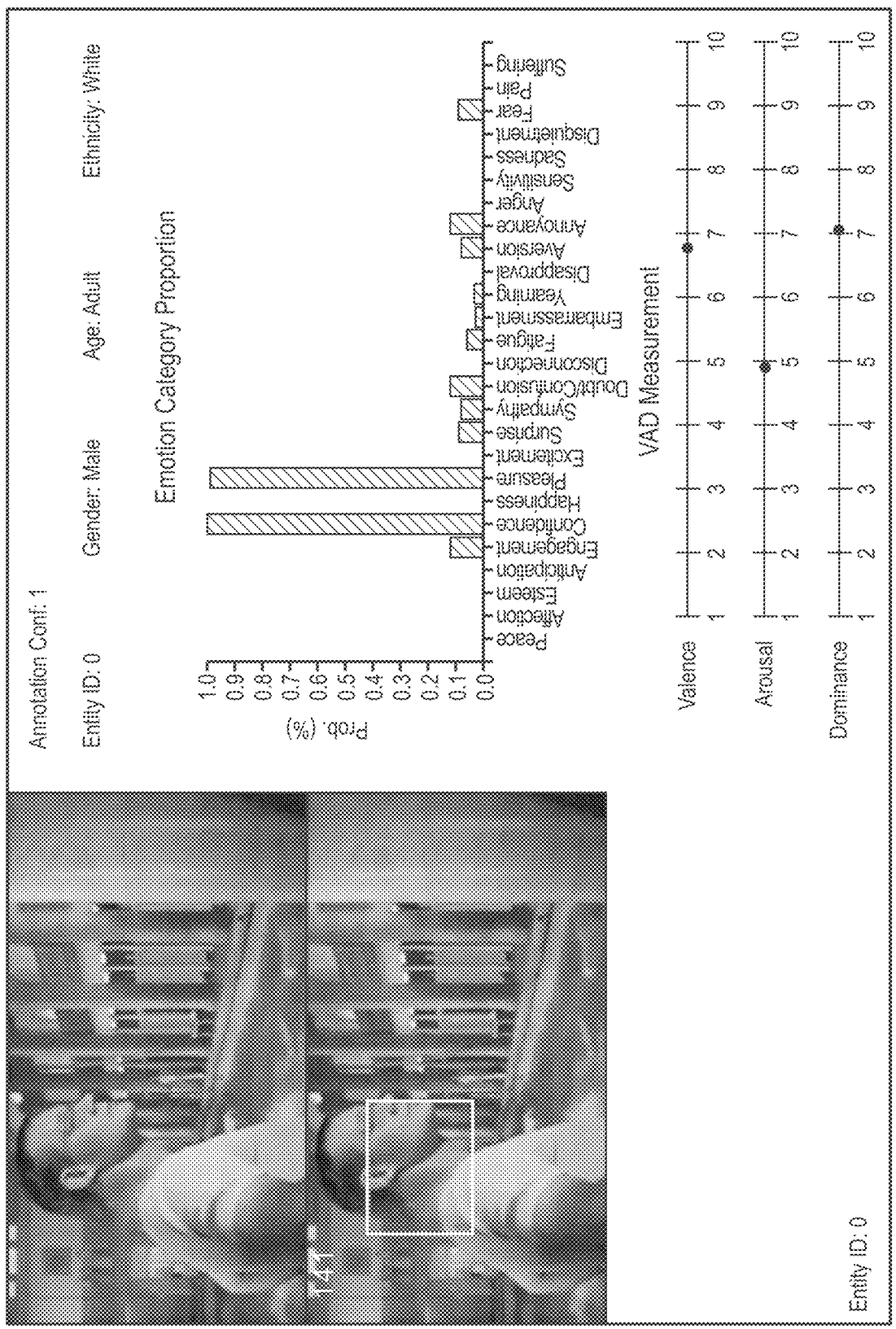
FIG. 6F depicts and illustrative screenshot of a high-confidence instance for the categorical emotion of confidence, according to one or more embodiments of the present disclosure.
Figure 6G:
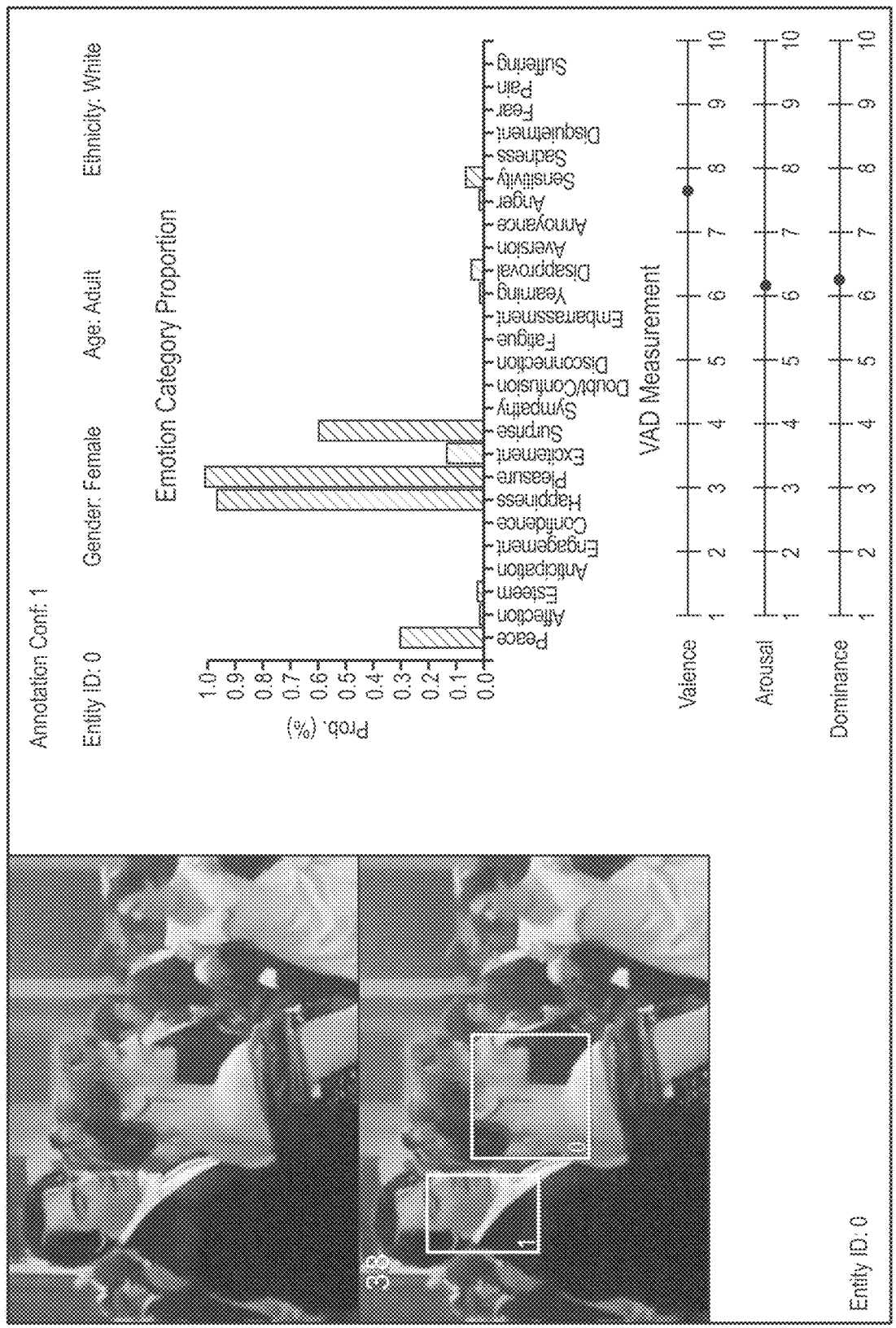
FIG. 6G depicts and illustrative screenshot of a high-confidence instance for the categorical emotion of happiness, according to one or more embodiments of the present disclosure.
Figure 6H:
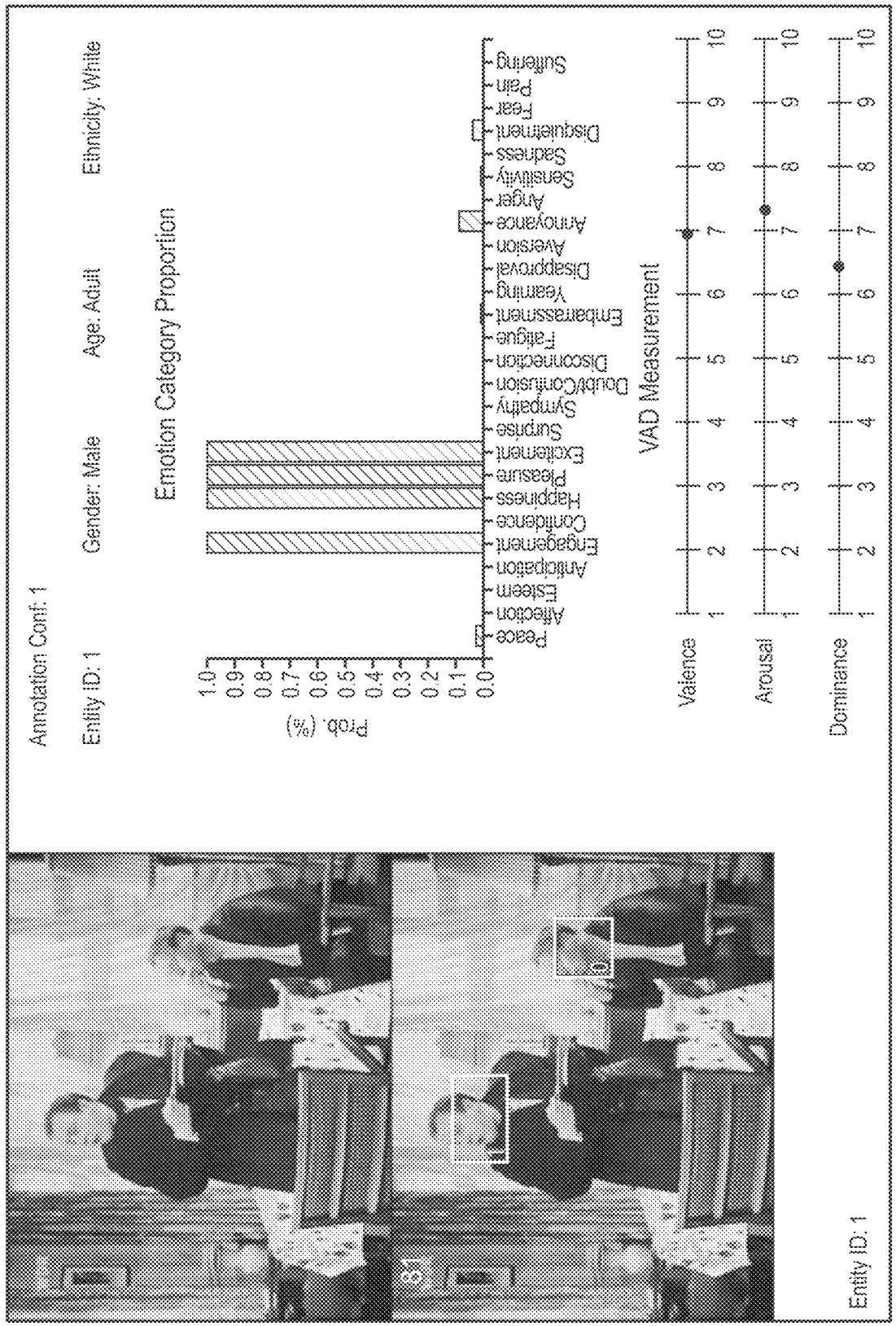
FIG. 6H depicts and illustrative screenshot of a high-confidence instance for the categorical emotion of pleasure, according to one or more embodiments of the present disclosure.
Figure 6I:
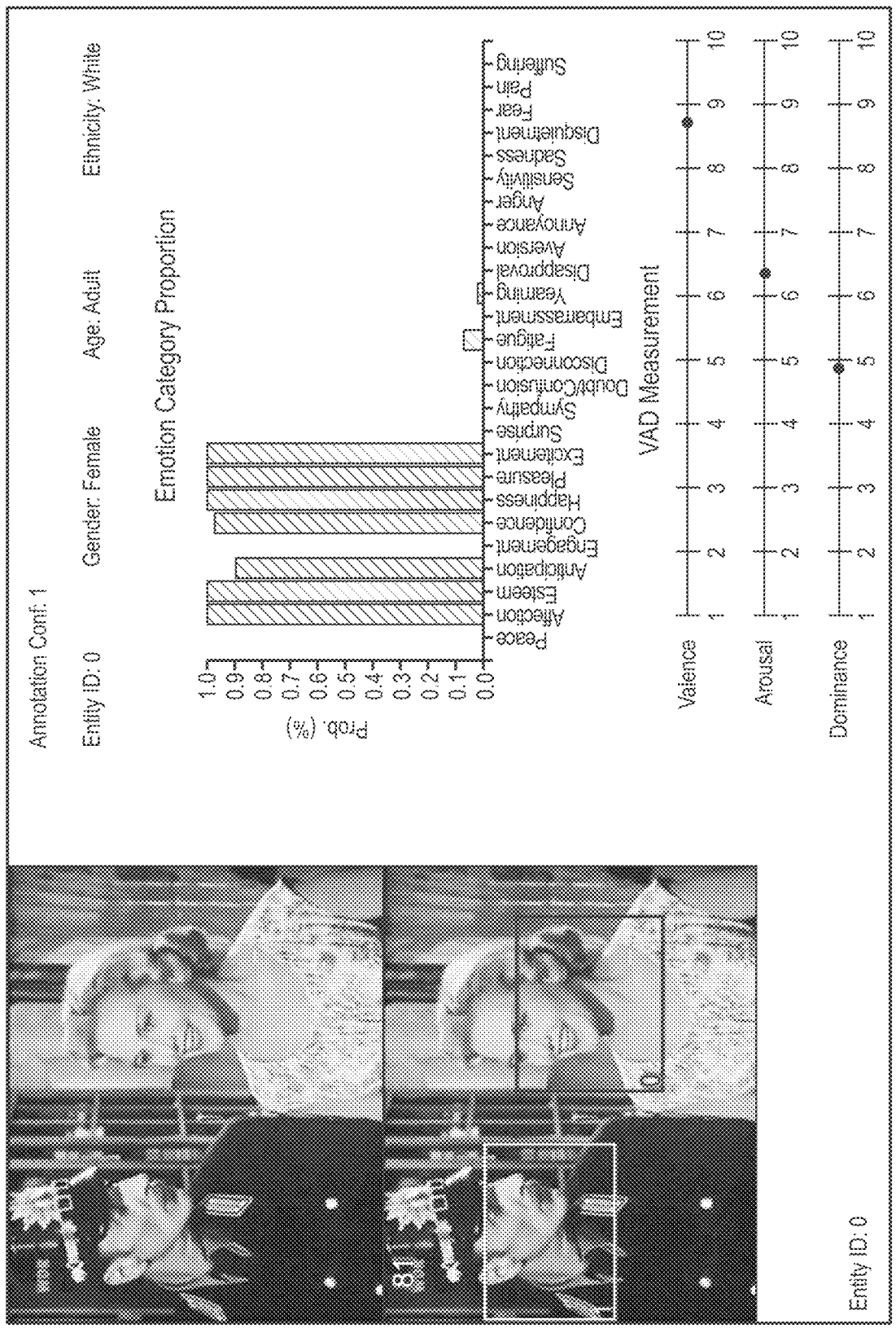
FIG. 6I depicts and illustrative screenshot of a high-confidence instance for the categorical emotion of excitement, according to one or more embodiments of the present disclosure.
Figure 6J:
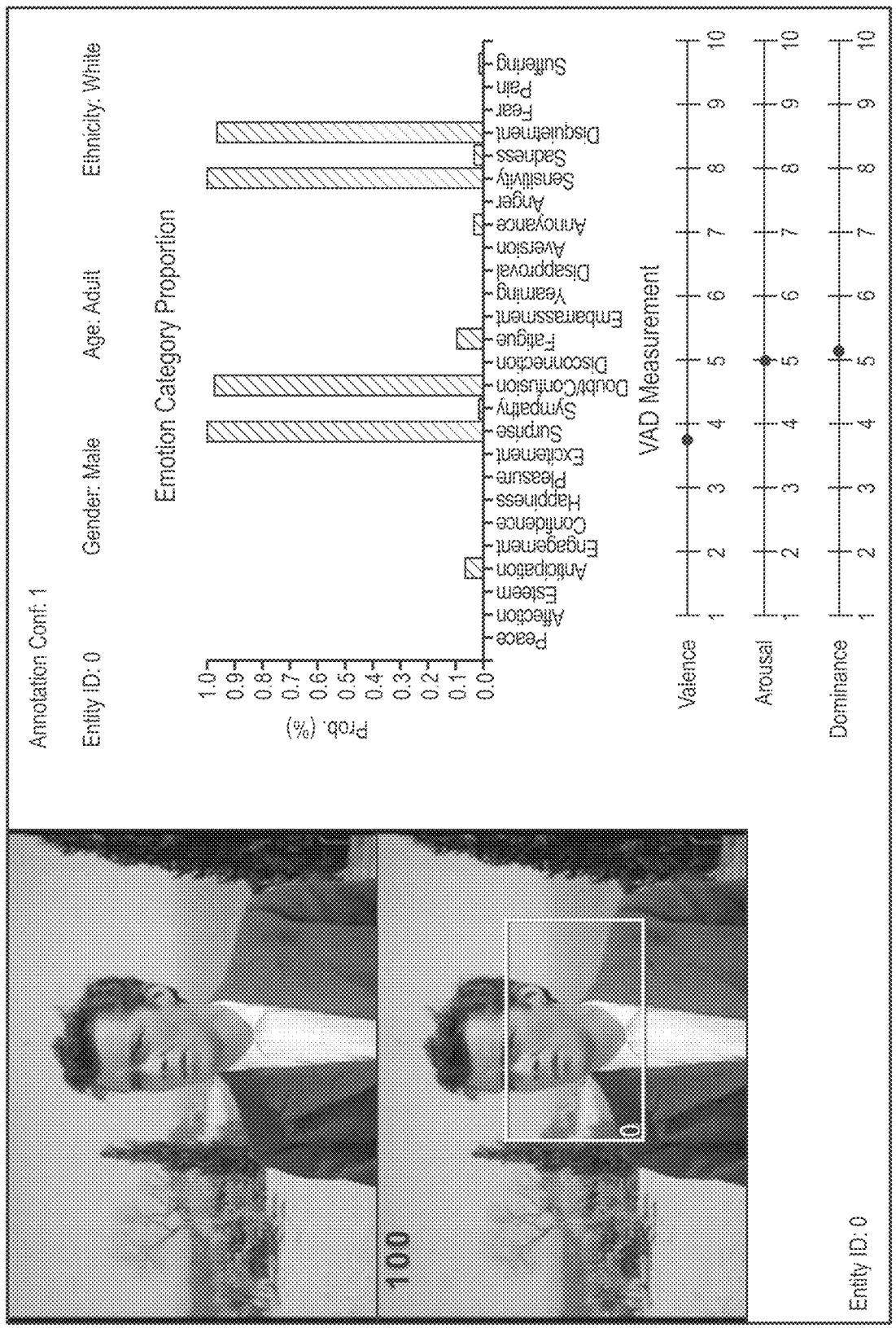
FIG. 6J depicts and illustrative screenshot of a high-confidence instance for the categorical emotion of surprise, according to one or more embodiments of the present disclosure.
Figure 6K:
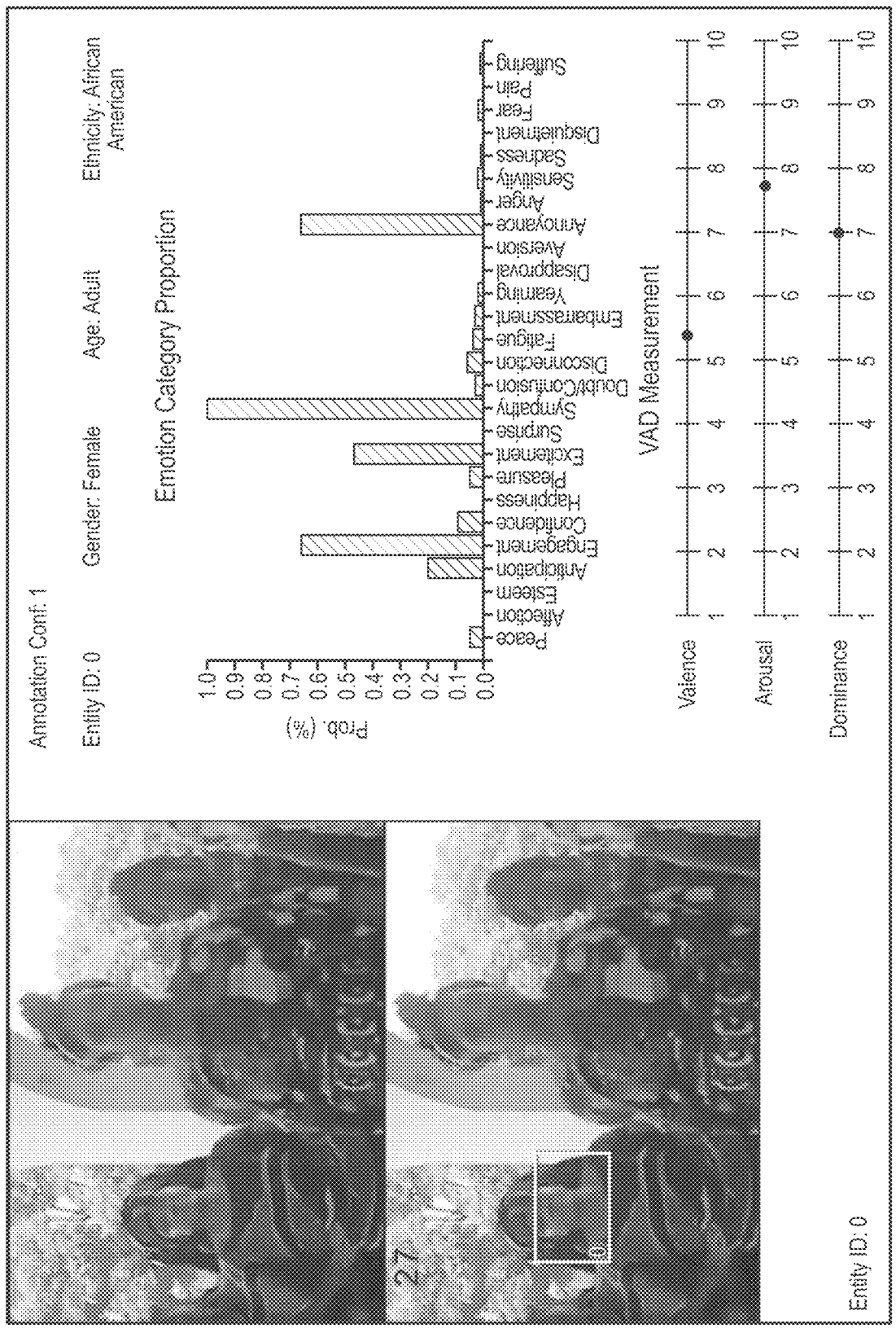
FIG. 6K depicts and illustrative screenshot of a high-confidence instance for the categorical emotion of sympathy, according to one or more embodiments of the present disclosure.
Figure 6L:
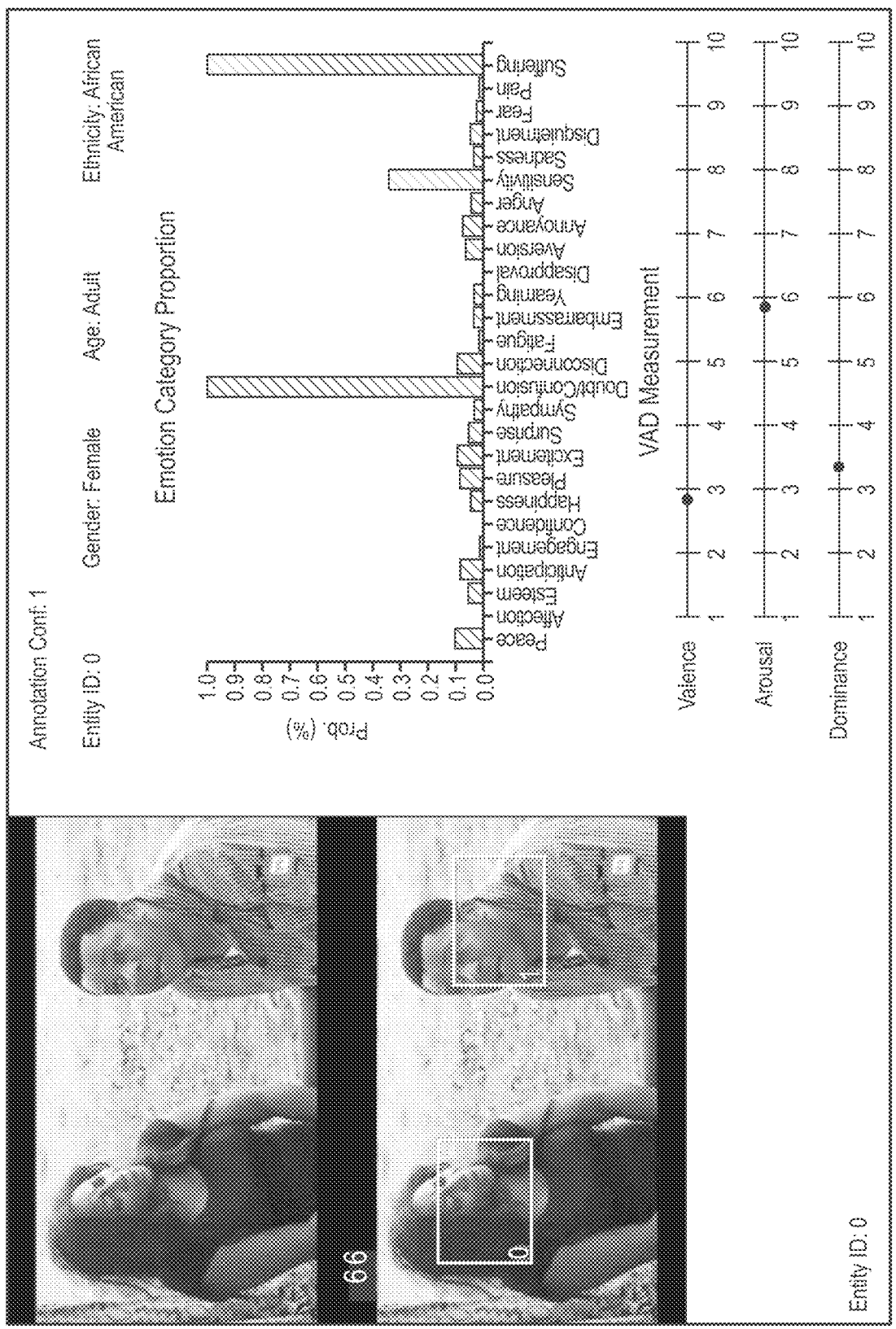
FIG. 6L depicts and illustrative screenshot of a high-confidence instance for the categorical emotion of doubt/confusion, according to one or more embodiments of the present disclosure.
Figure 6M:
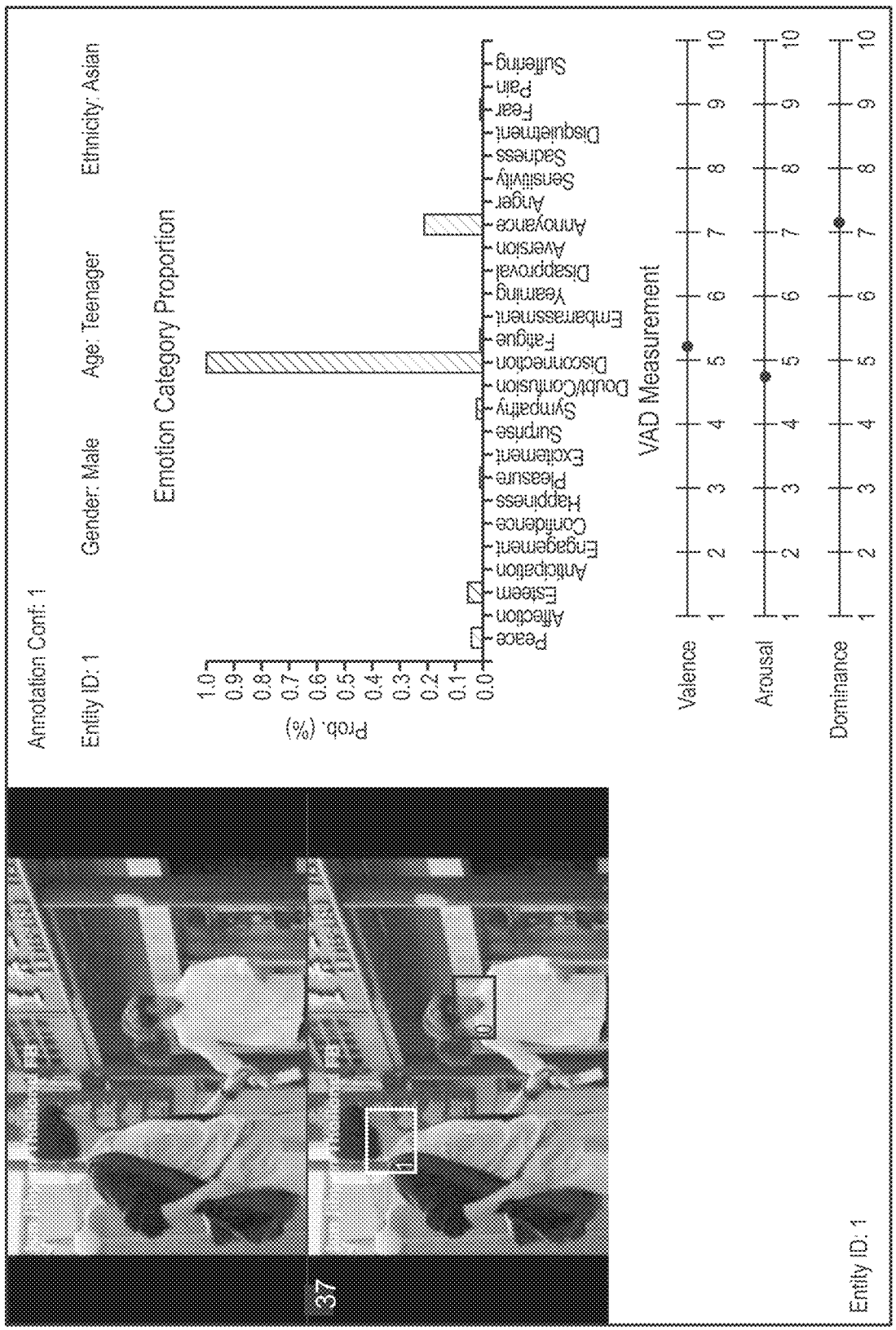
FIG. 6M depicts and illustrative screenshot of a high-confidence instance for the categorical emotion of disconnection, according to one or more embodiments of the present disclosure.
Figure 6N:
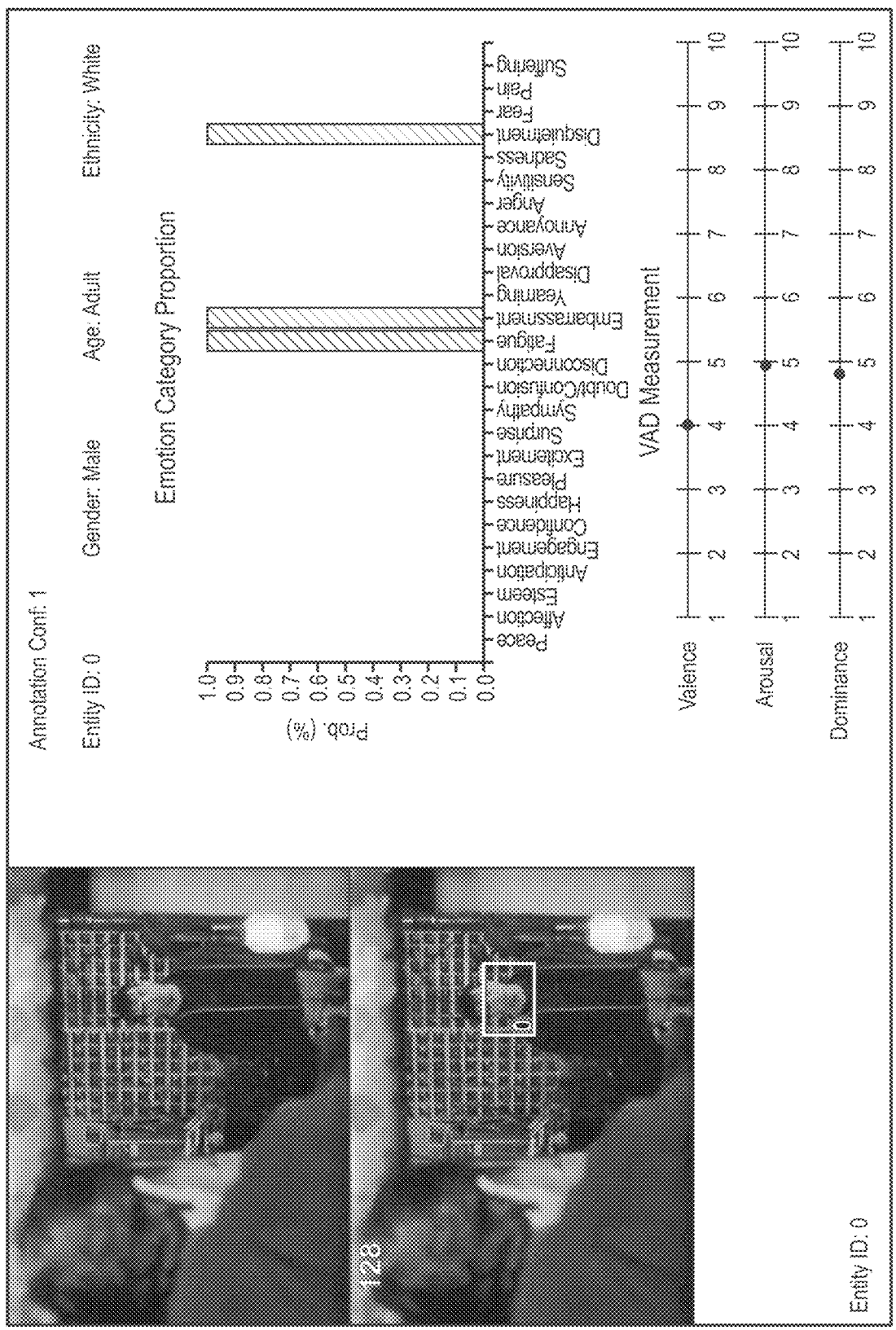
FIG. 6N depicts and illustrative screenshot of a high-confidence instance for the categorical emotion of fatigue, according to one or more embodiments of the present disclosure.
Figure 60:
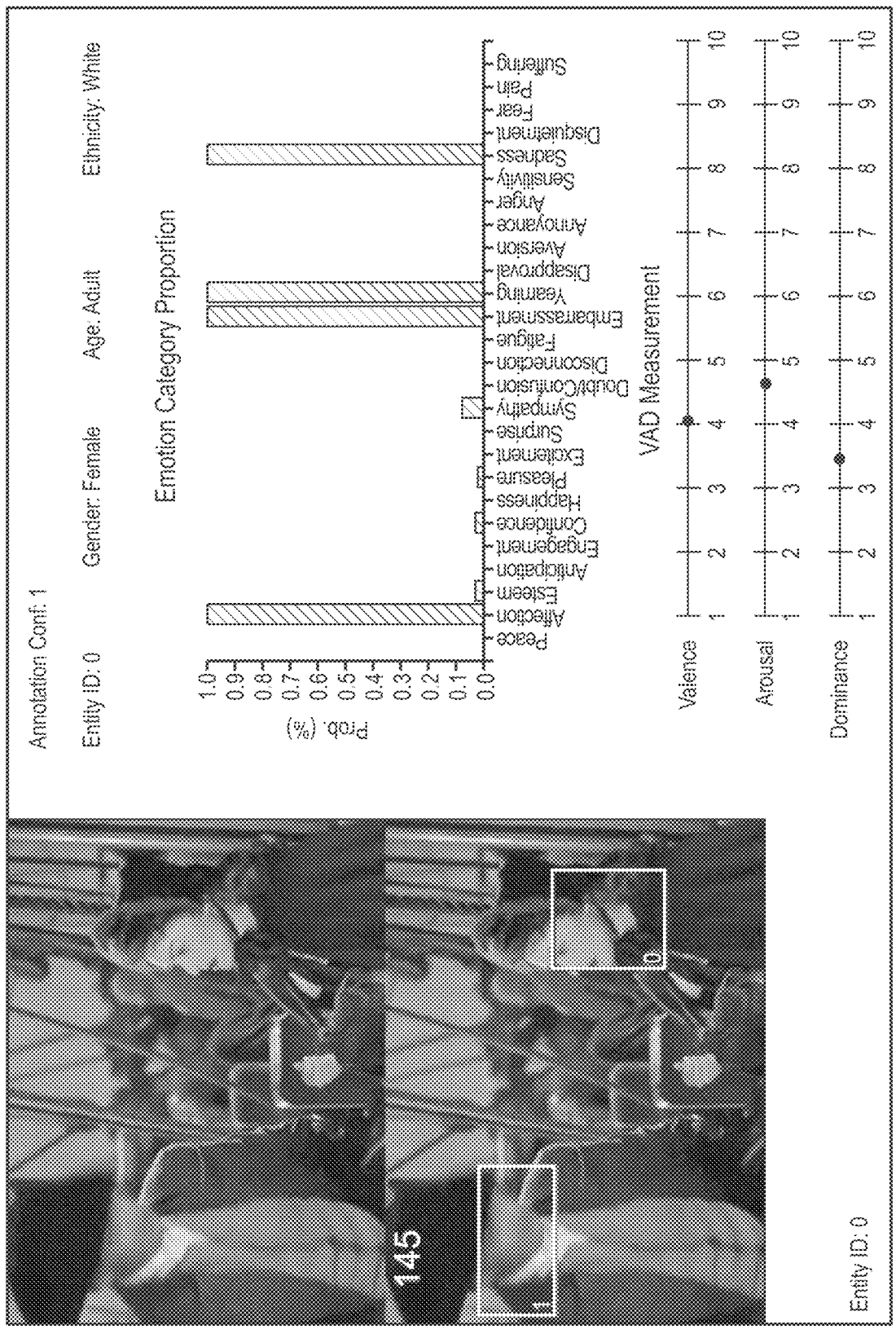
Figure 6P:
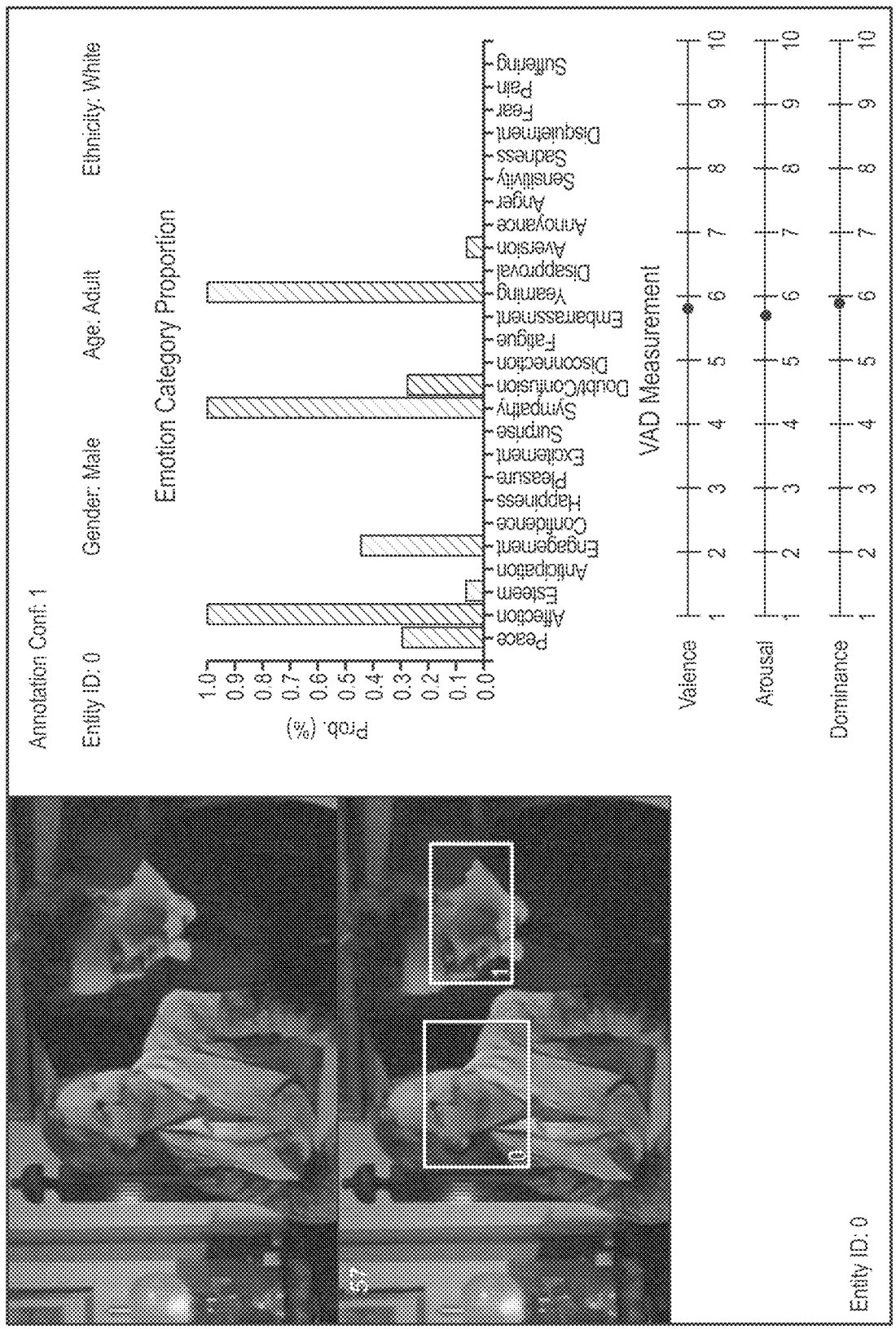
FIG. 6P depicts and illustrative screenshot of a high-confidence instance for the categorical emotion of yearning, according to one or more embodiments of the present disclosure.
Figure 6Q:
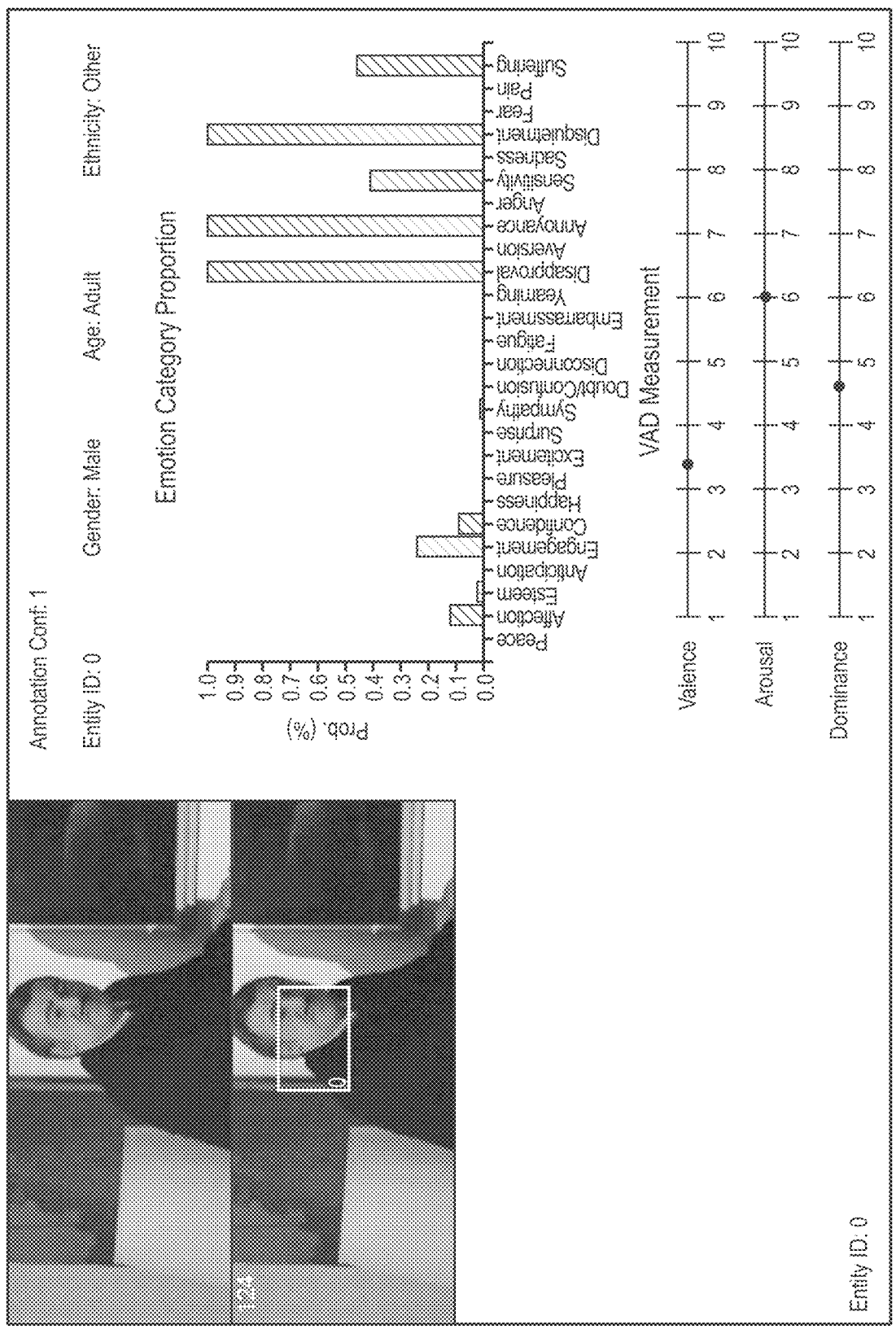
FIG. 6Q depicts and illustrative screenshot of a high-confidence instance for the categorical emotion of disapproval, according to one or more embodiments of the present disclosure.
Figure 6R:
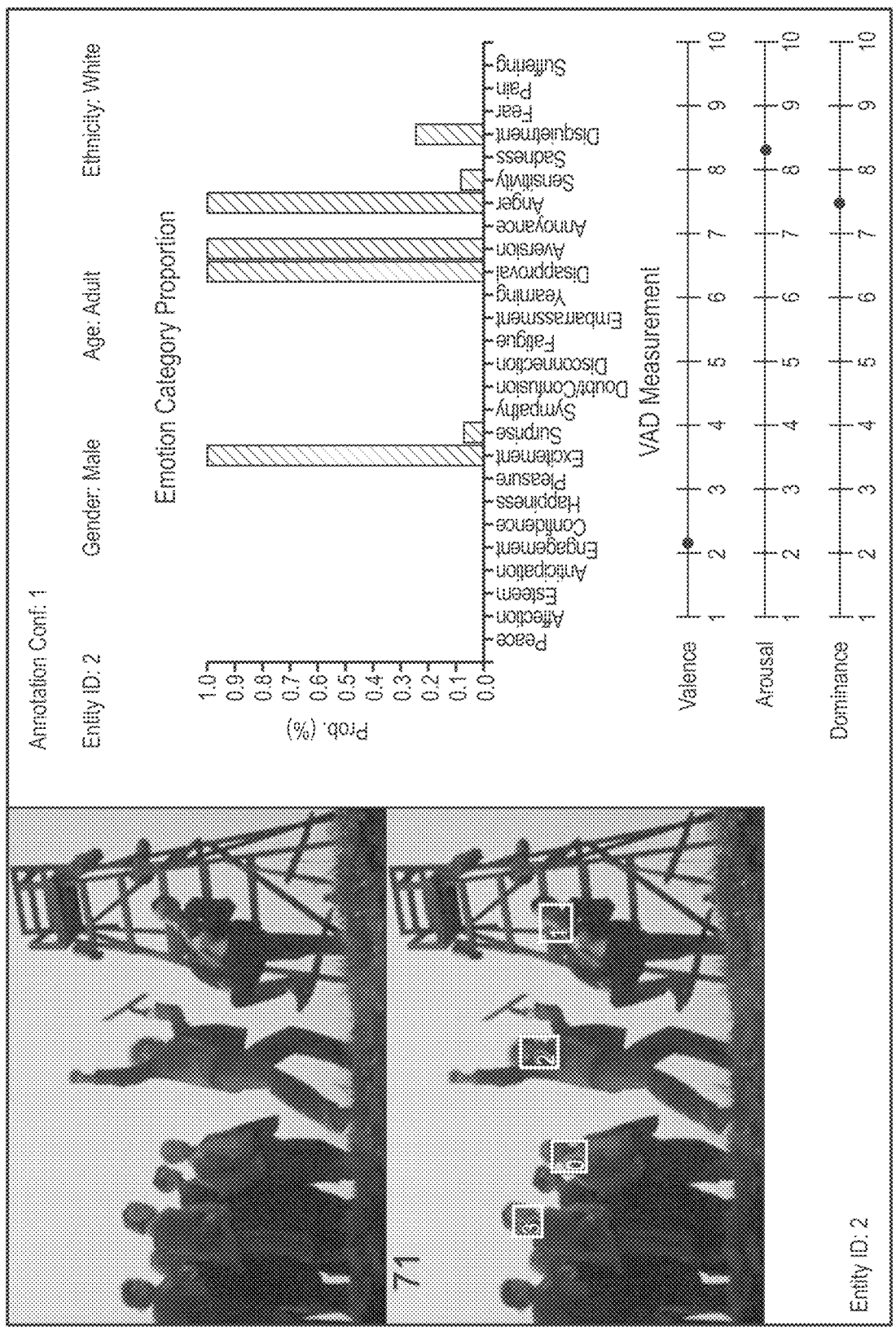
FIG. 6R depicts and illustrative screenshot of a high-confidence instance for the categorical emotion of aversion, according to one or more embodiments of the present disclosure.
Figure 6S:
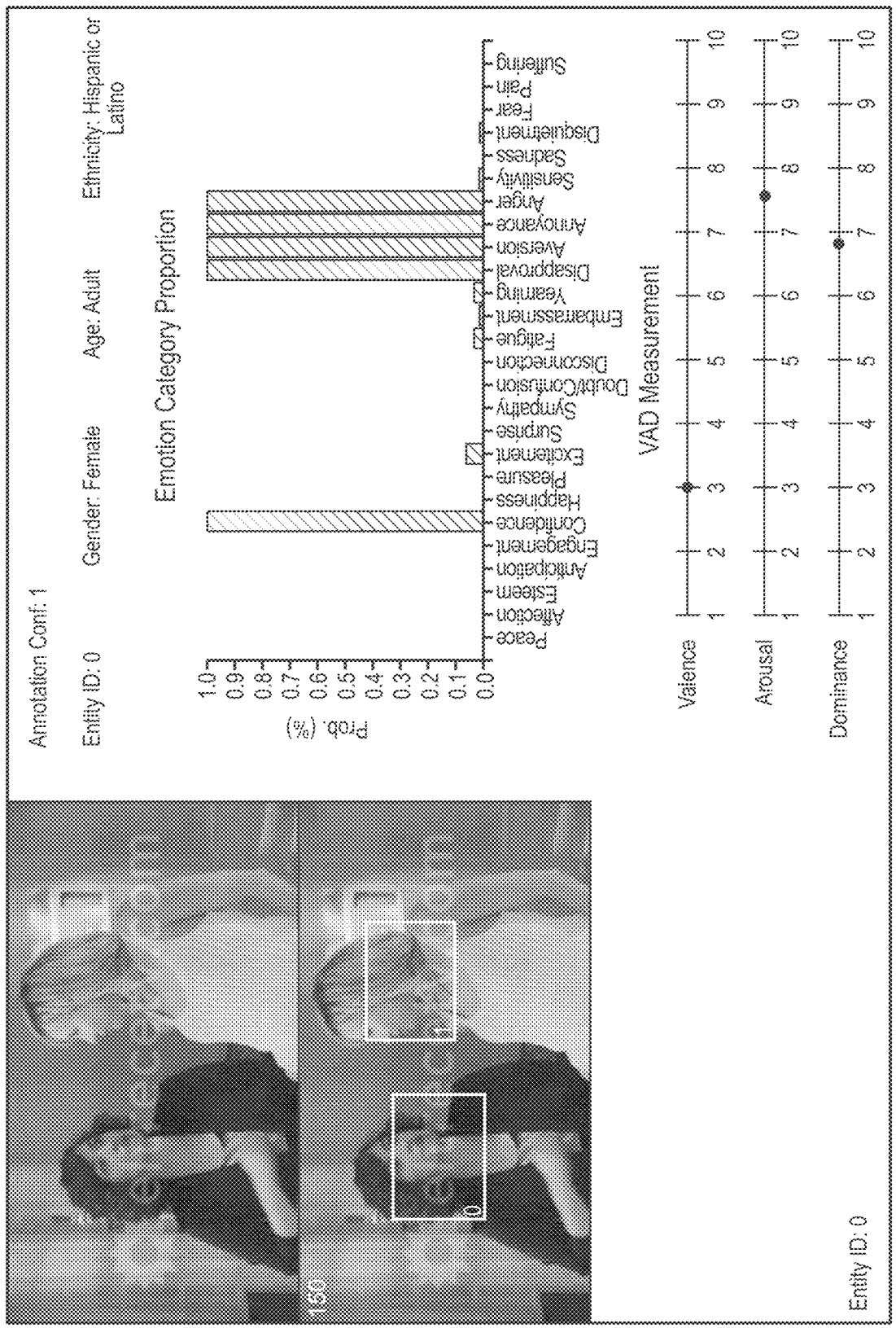
FIG. 6S depicts and illustrative screenshot of a high-confidence instance for the categorical emotion of annoyance, according to one or more embodiments of the present disclosure.
Figure 6T:
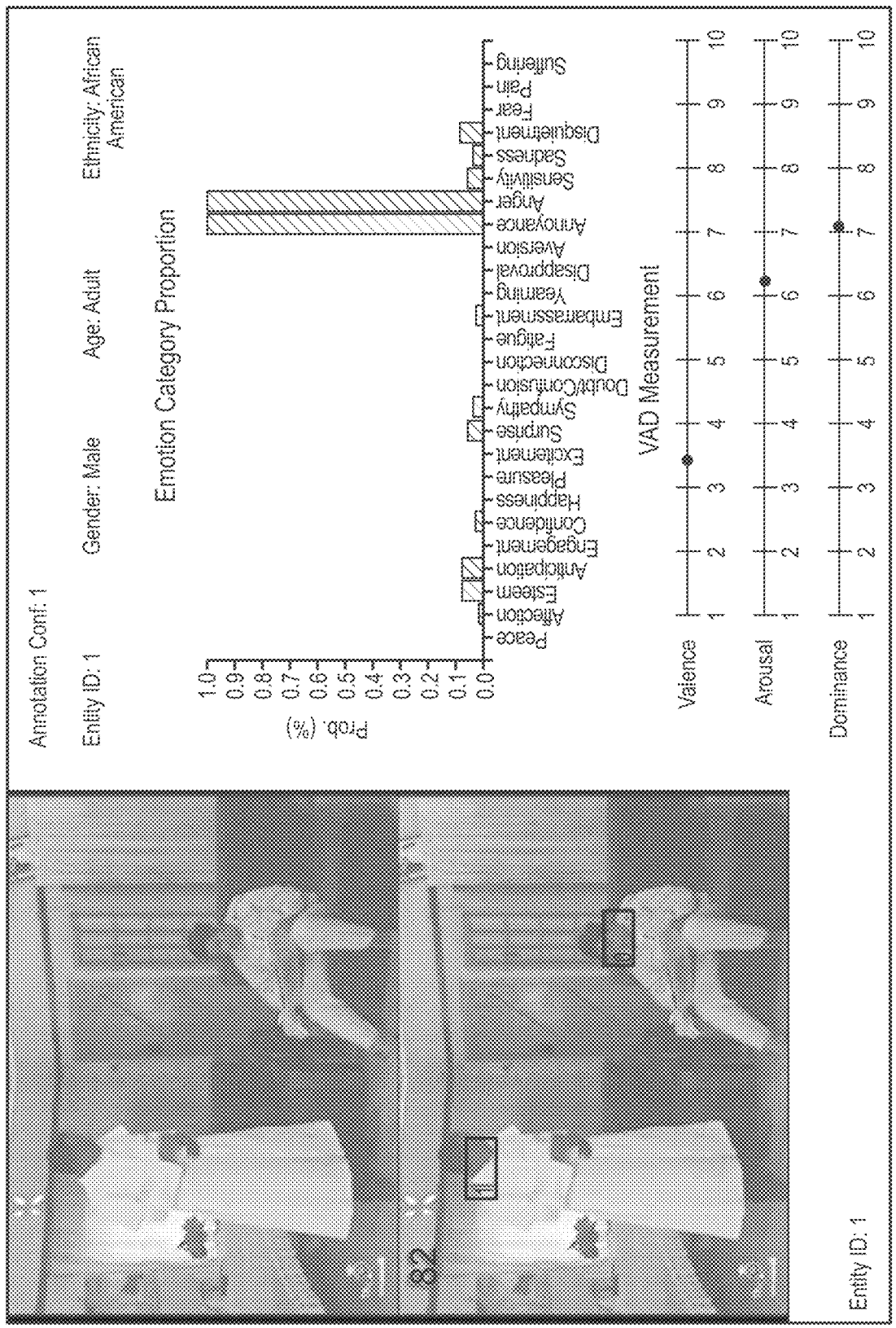
FIG. 6T depicts and illustrative screenshot of a high-confidence instance for the categorical emotion of anger, according to one or more embodiments of the present disclosure.
Figure 6U:
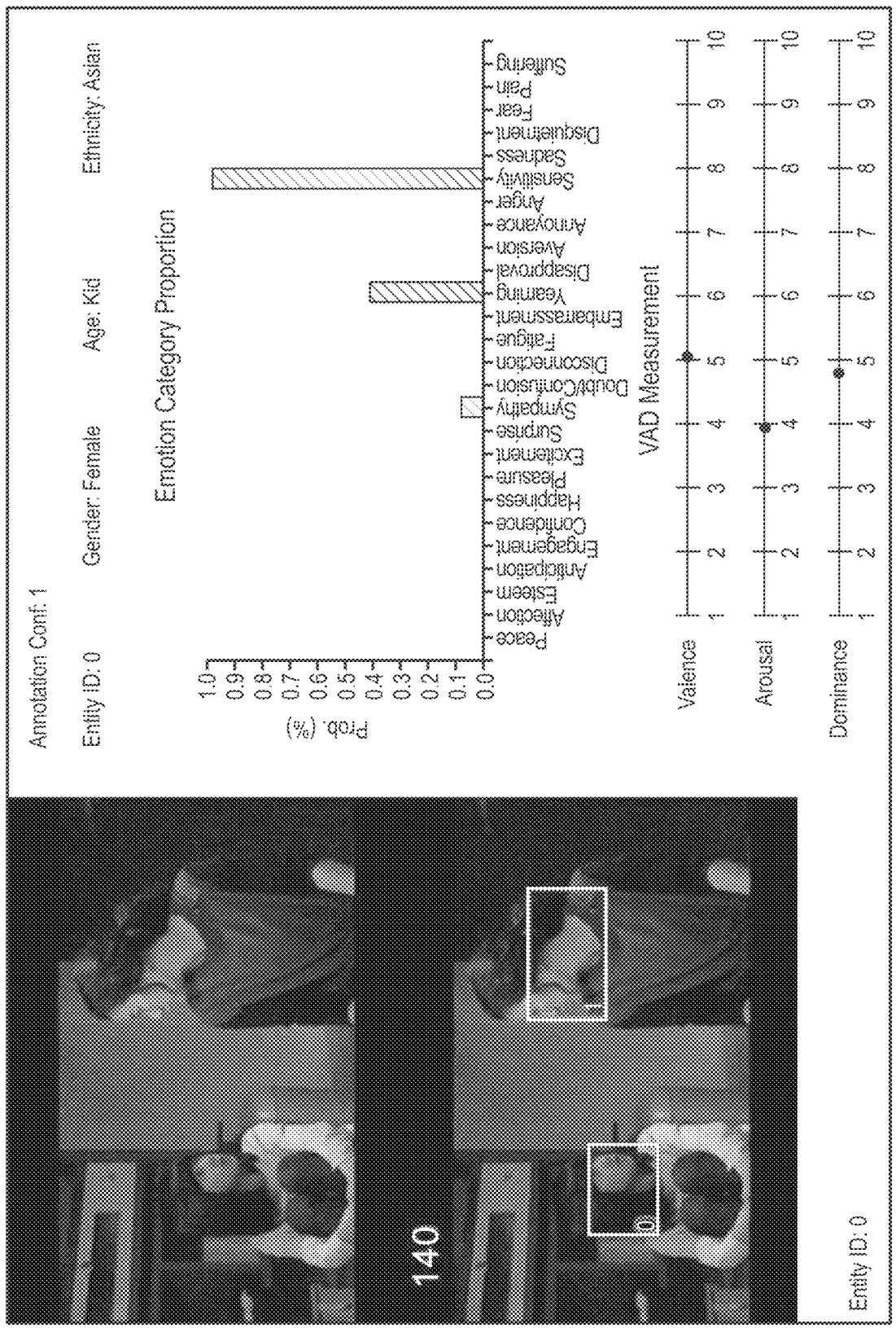
FIG. 6U depicts and illustrative screenshot of a high-confidence instance for the categorical emotion of sensitivity, according to one or more embodiments of the present disclosure.
Figure 6V:
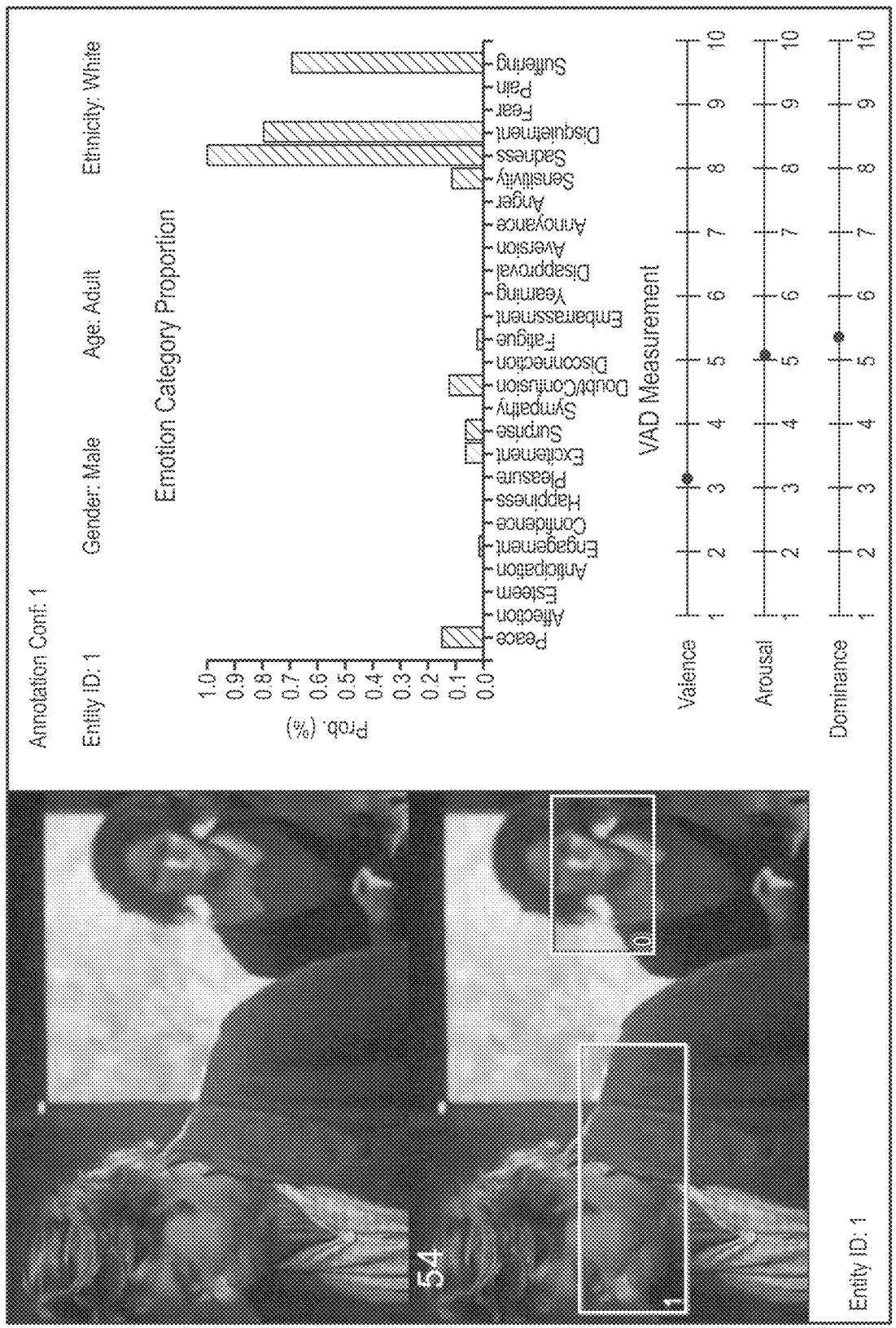
FIG. 6V depicts and illustrative screenshot of a high-confidence instance for the categorical emotion of sadness, according to one or more embodiments of the present disclosure.
Figure 6W:
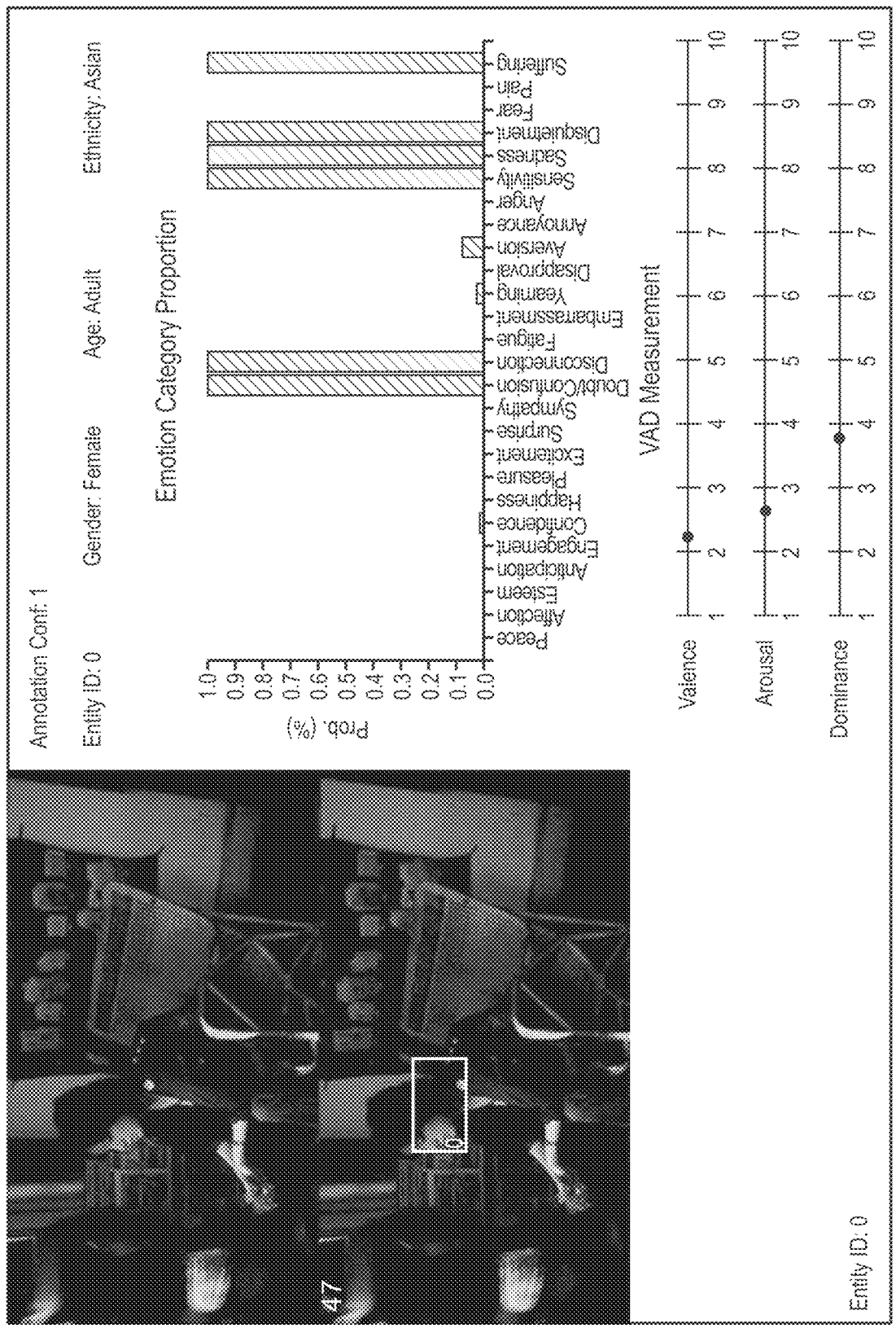
FIG. 6W depicts and illustrative screenshot of a high-confidence instance for the categorical emotion of disquietment, according to one or more embodiments of the present disclosure.
Figure 6X:
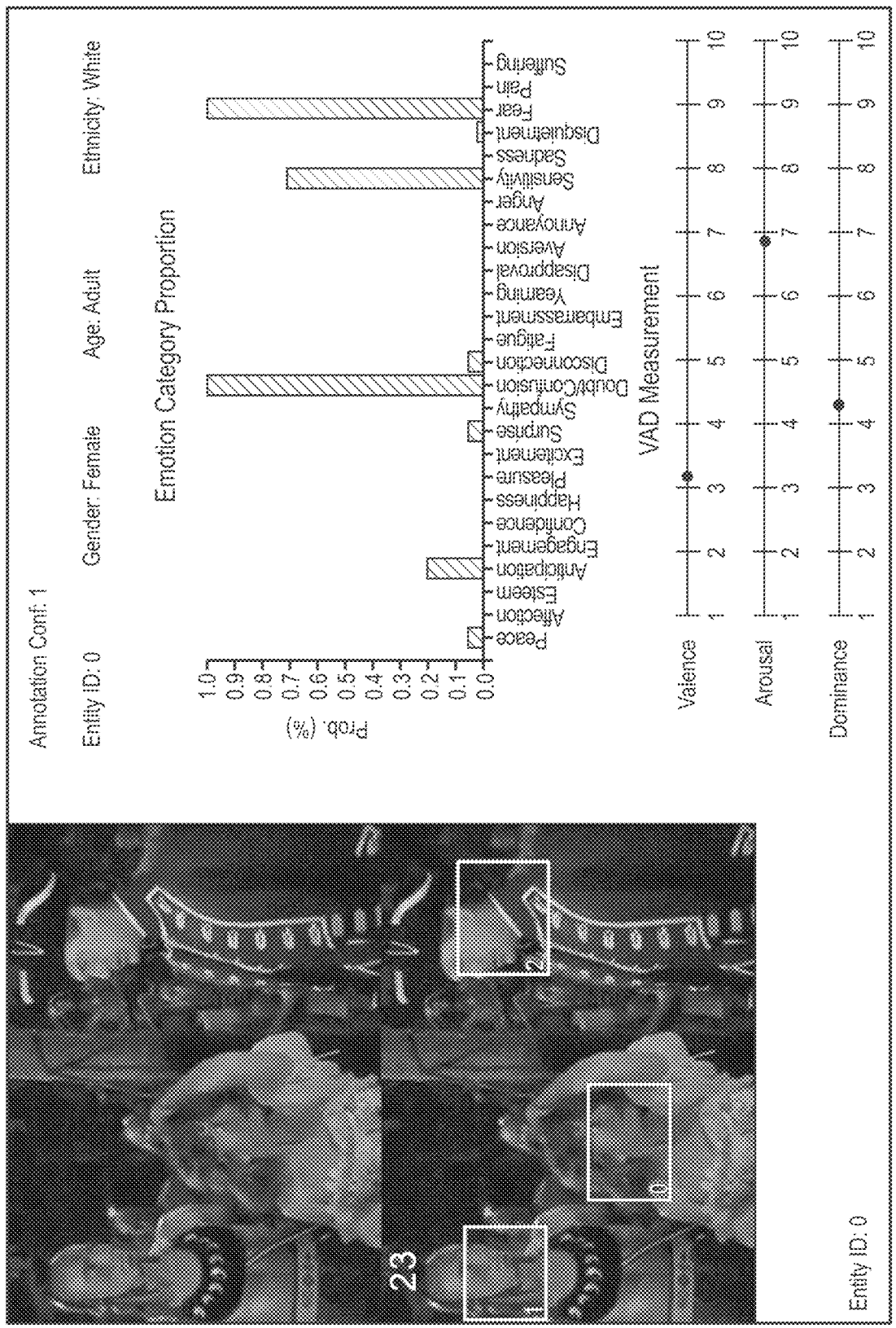
FIG. 6X depicts and illustrative screenshot of a high-confidence instance for the categorical emotion of fear, according to one or more embodiments of the present disclosure.
Figure 6Y:
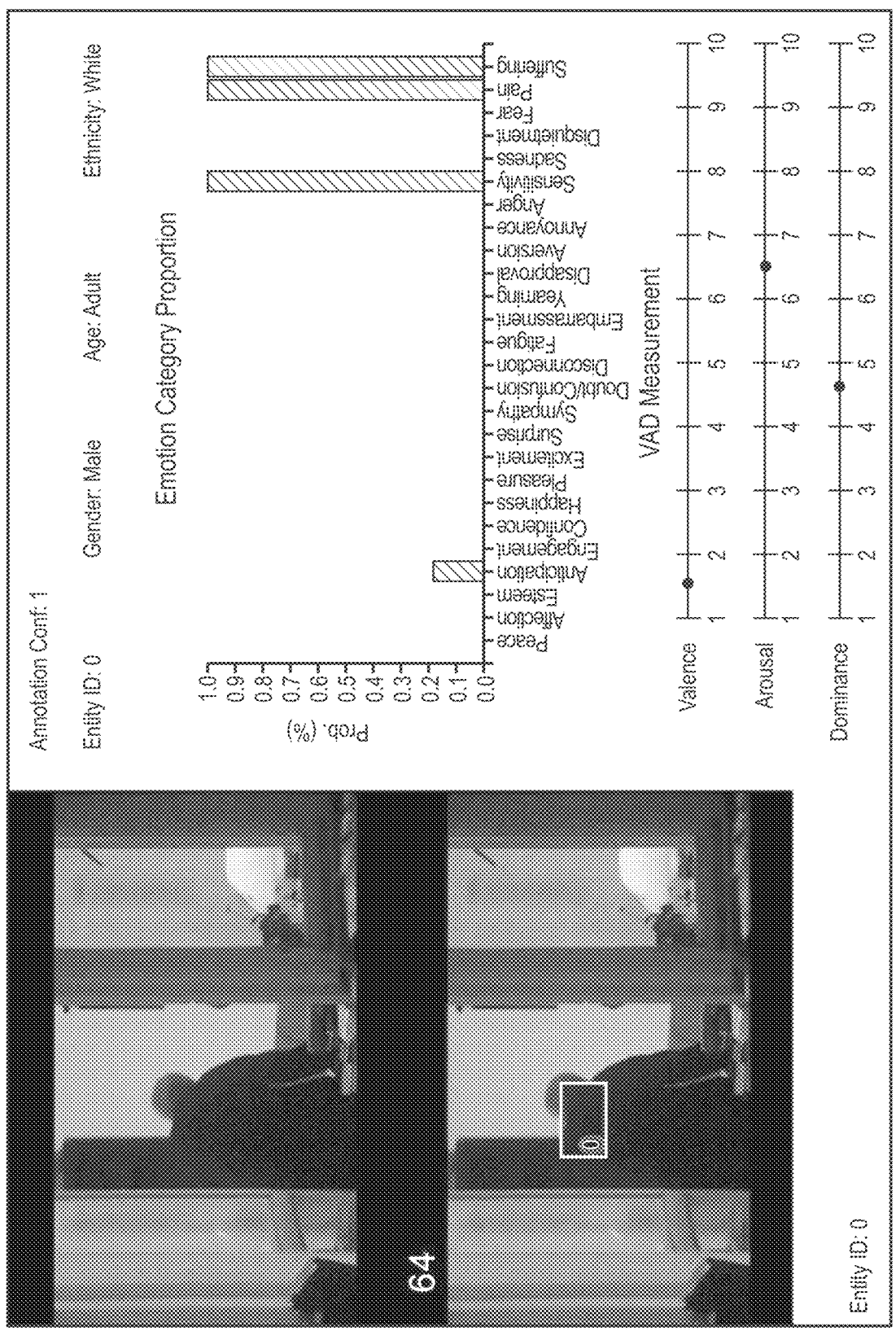
FIG. 6Y depicts and illustrative screenshot of a high-confidence instance for the categorical emotion of pain, according to one or more embodiments of the present disclosure.
Figure 6Z:
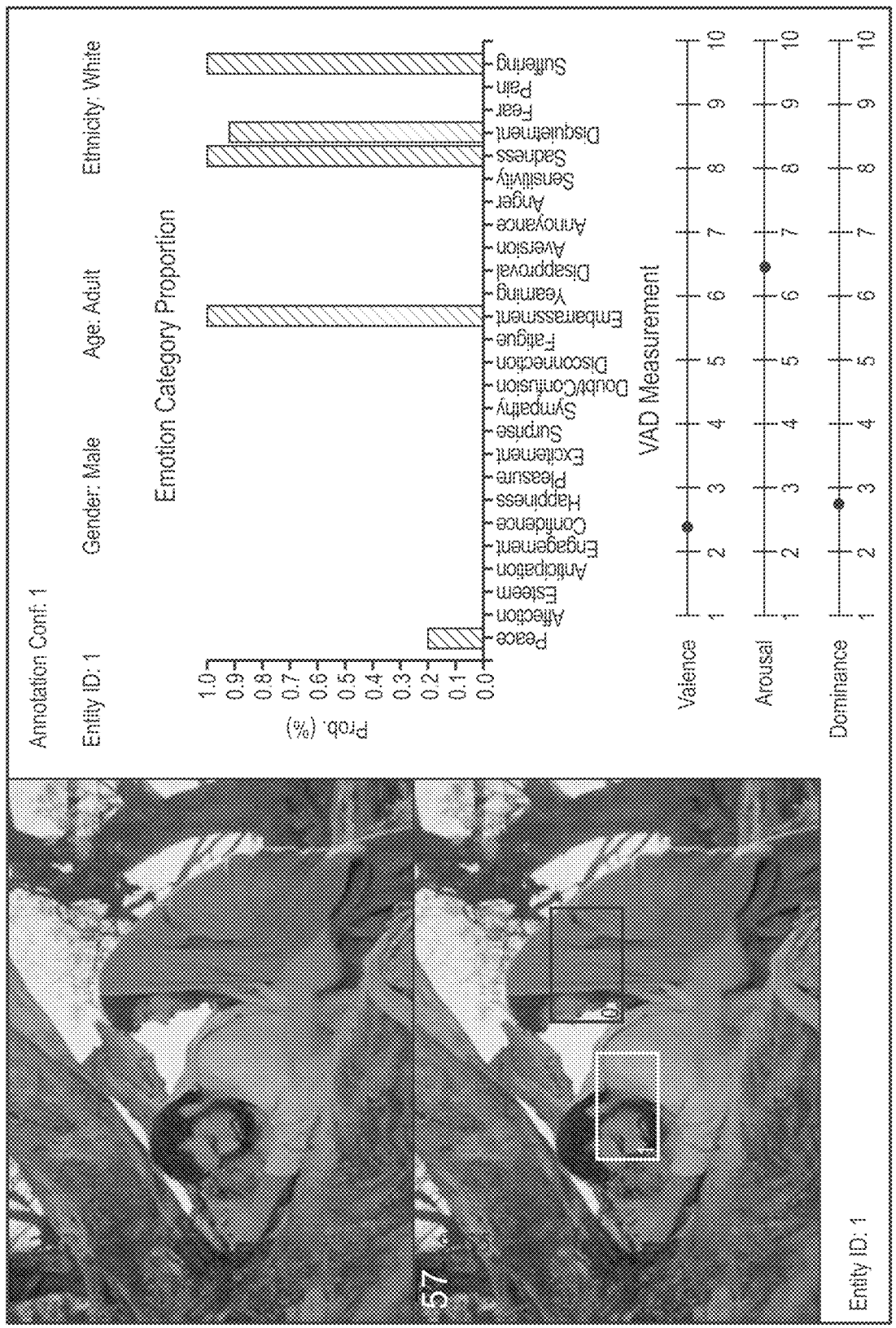
FIG. 6Z depicts and illustrative screenshot of a high-confidence instance for the categorical emotion of suffering, according to one or more embodiments of the present disclosure.
Figure 6A:
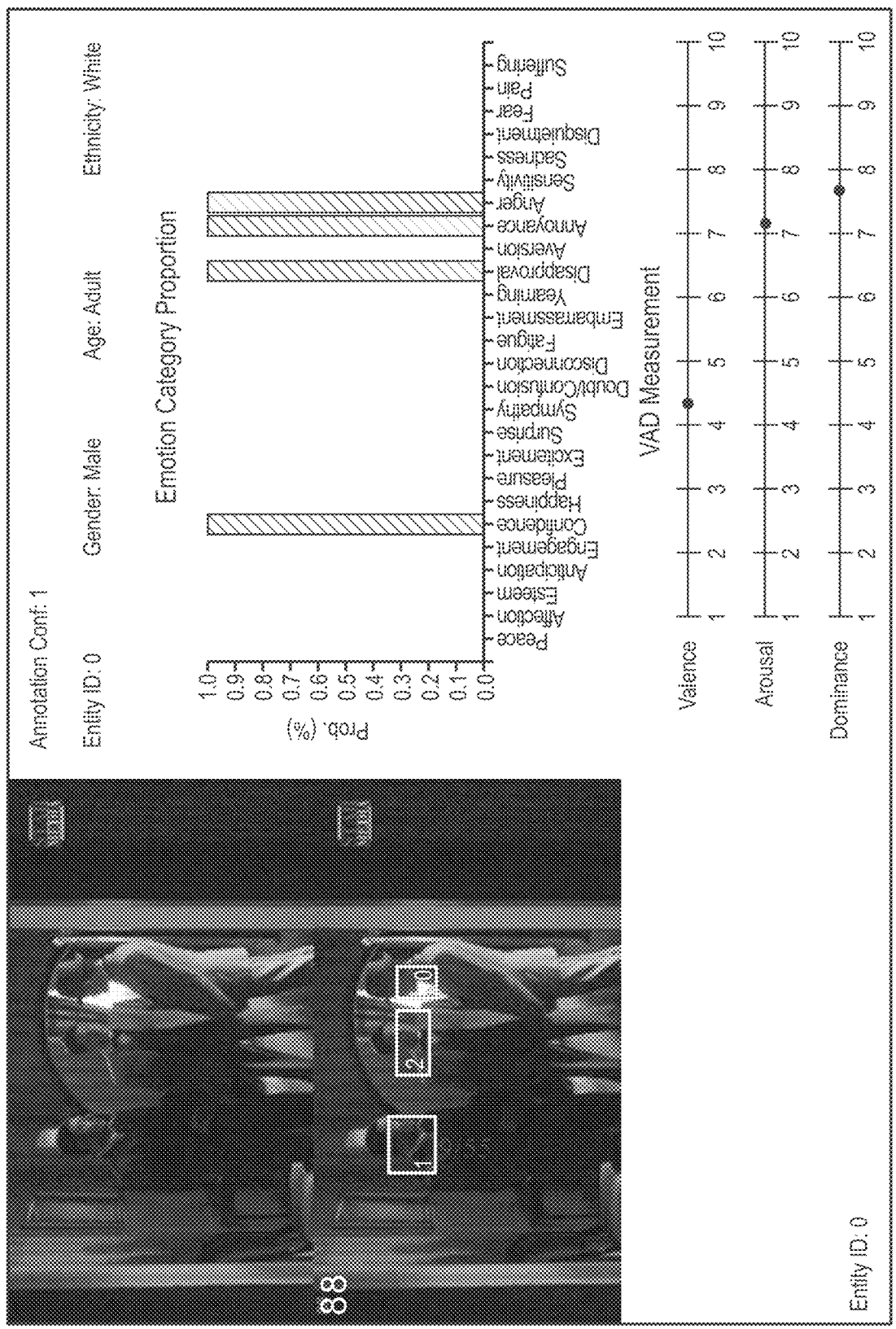
Figure 6B:
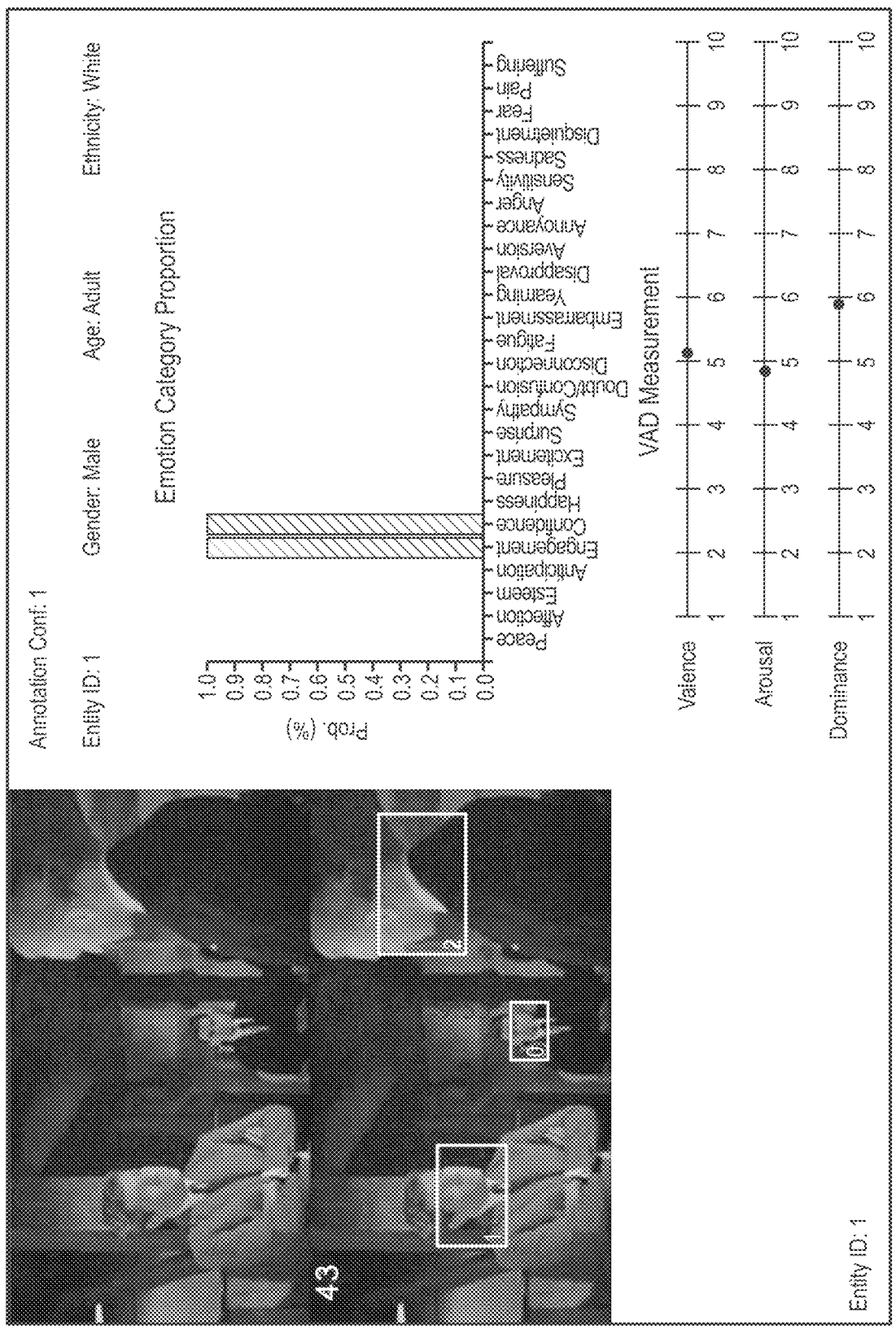
Figure 7A:
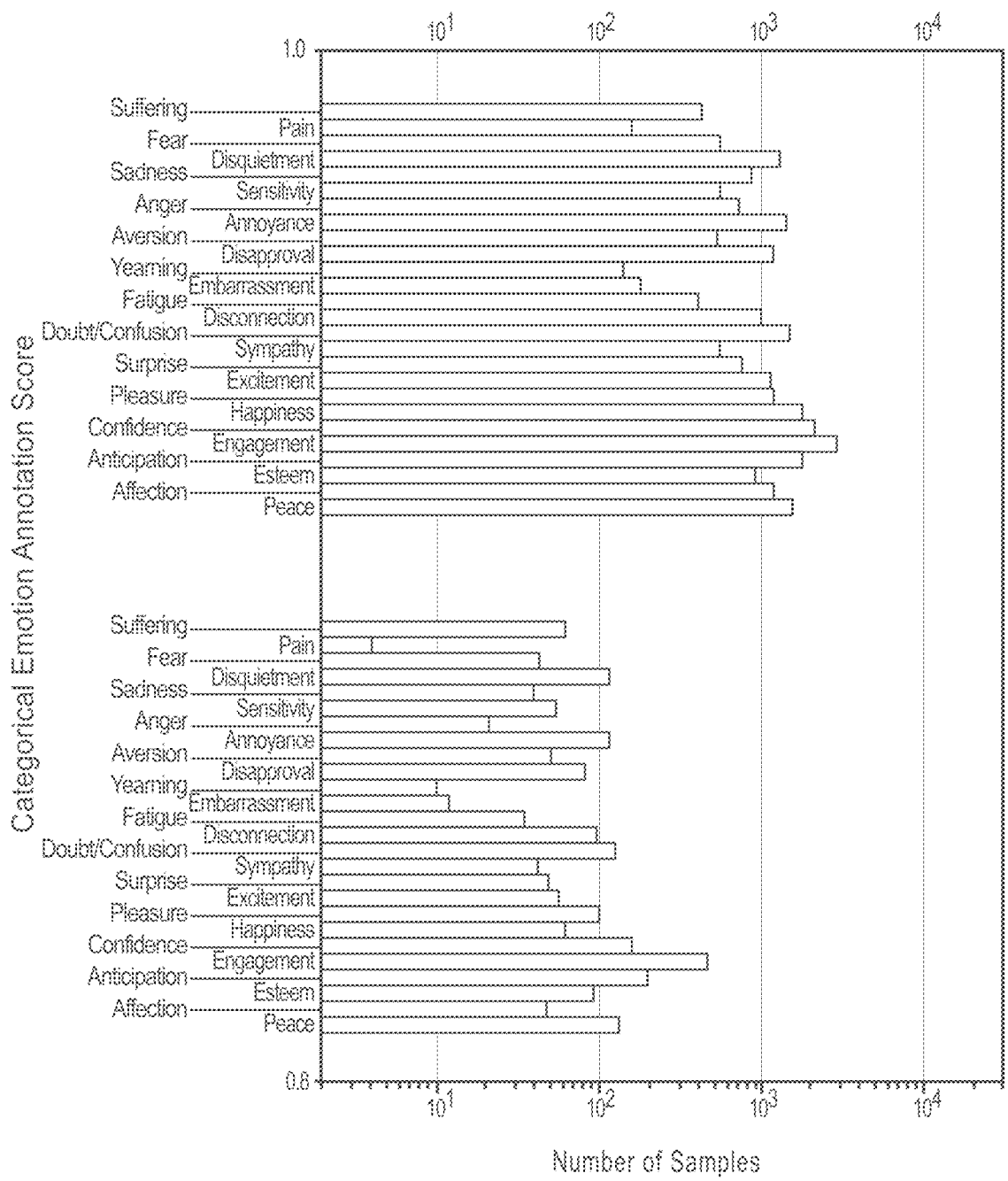
FIG. 7A depicts a bar chart illustrating distributions for each of the twenty-six (26) categorical emotions, according to one or more embodiments of the present disclosure.
Figure 7B:
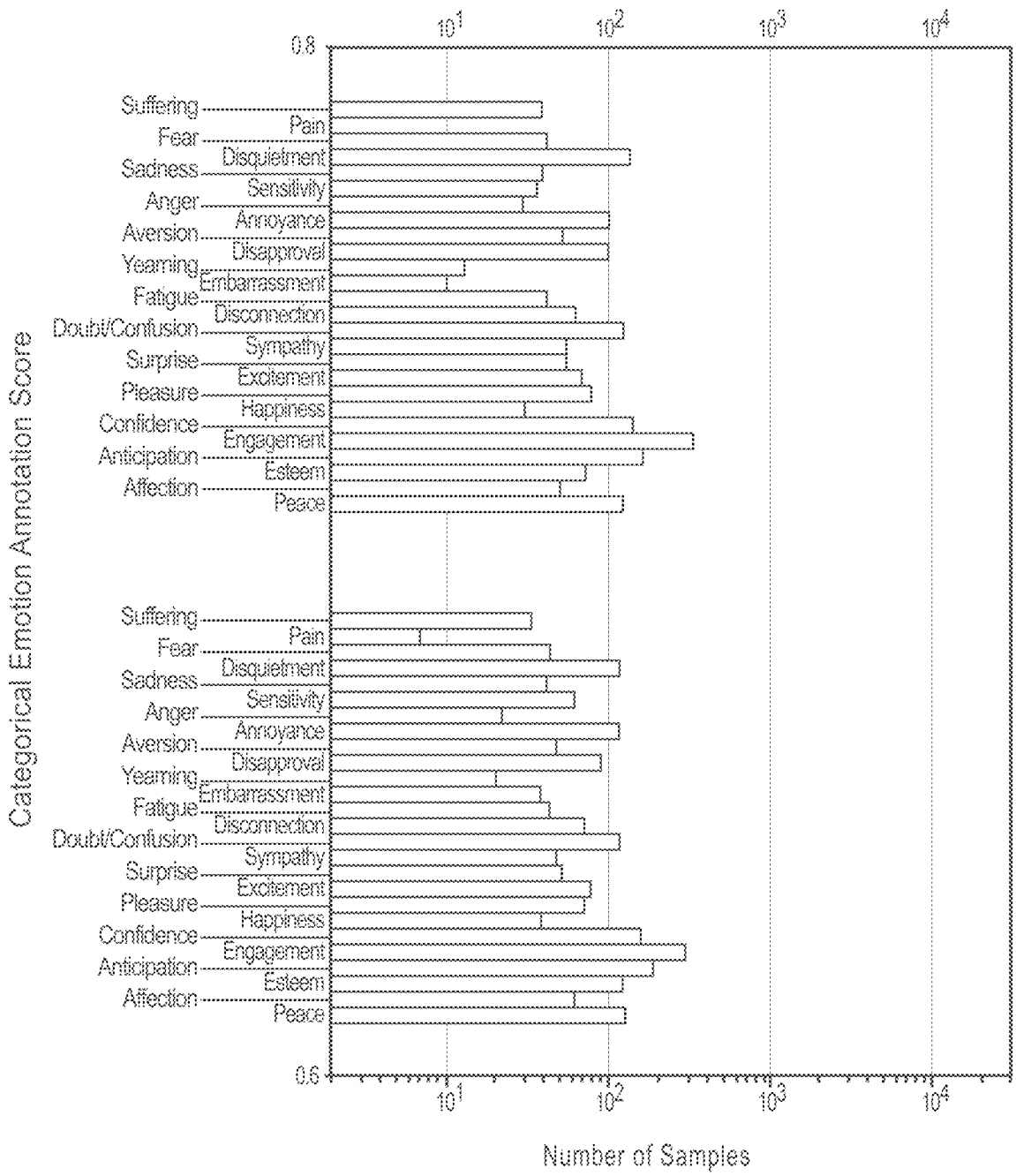
FIG. 7B depicts another bar chart illustrating distributions for each of the twenty-six (26) categorical emotions, according to one or more embodiments of the present disclosure.
Figure 7C:
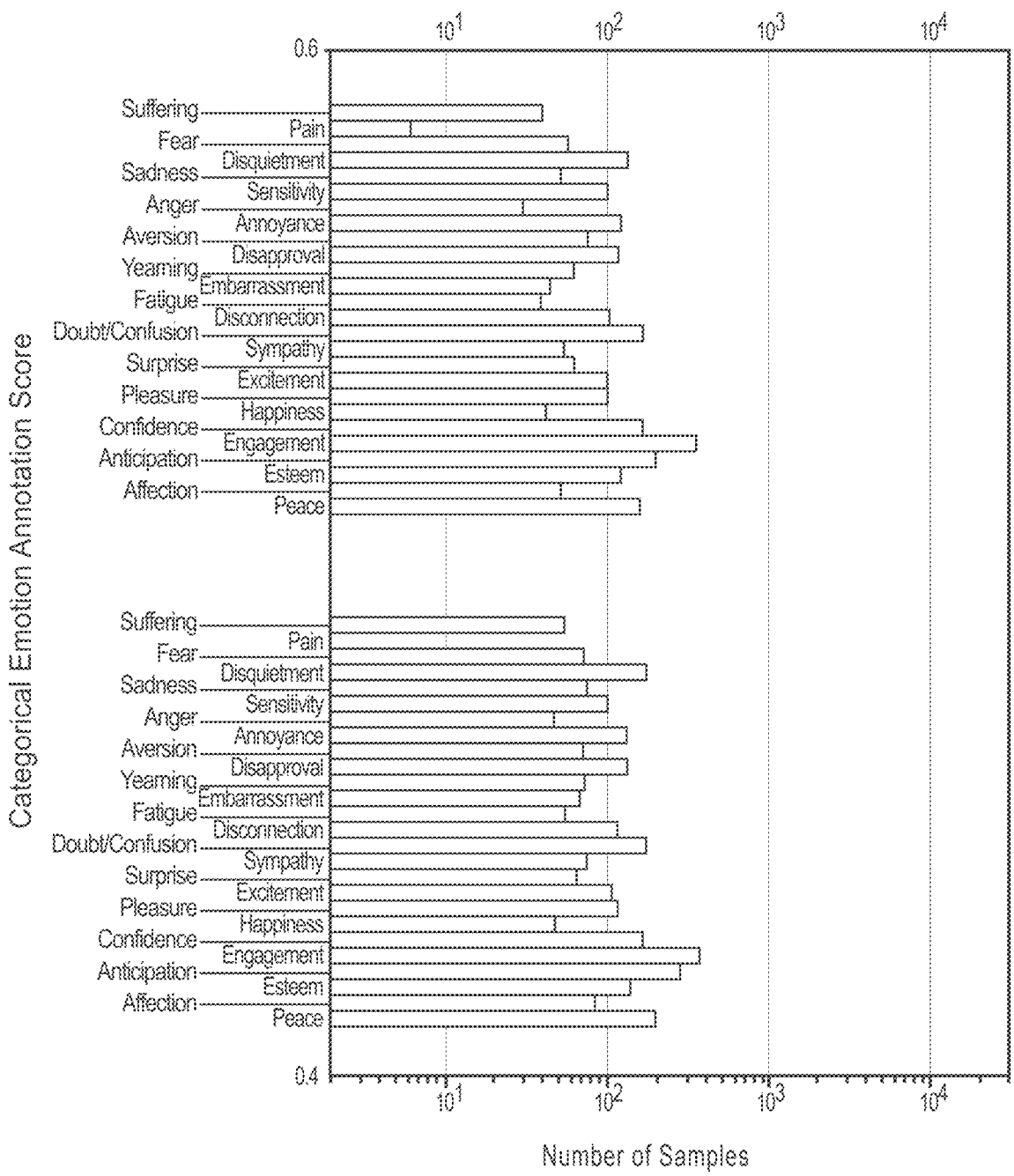
FIG. 7C depicts another bar chart illustrating distributions for each of the twenty-six (26) categorical emotions, according to one or more embodiments of the present disclosure.
Figure 7D:
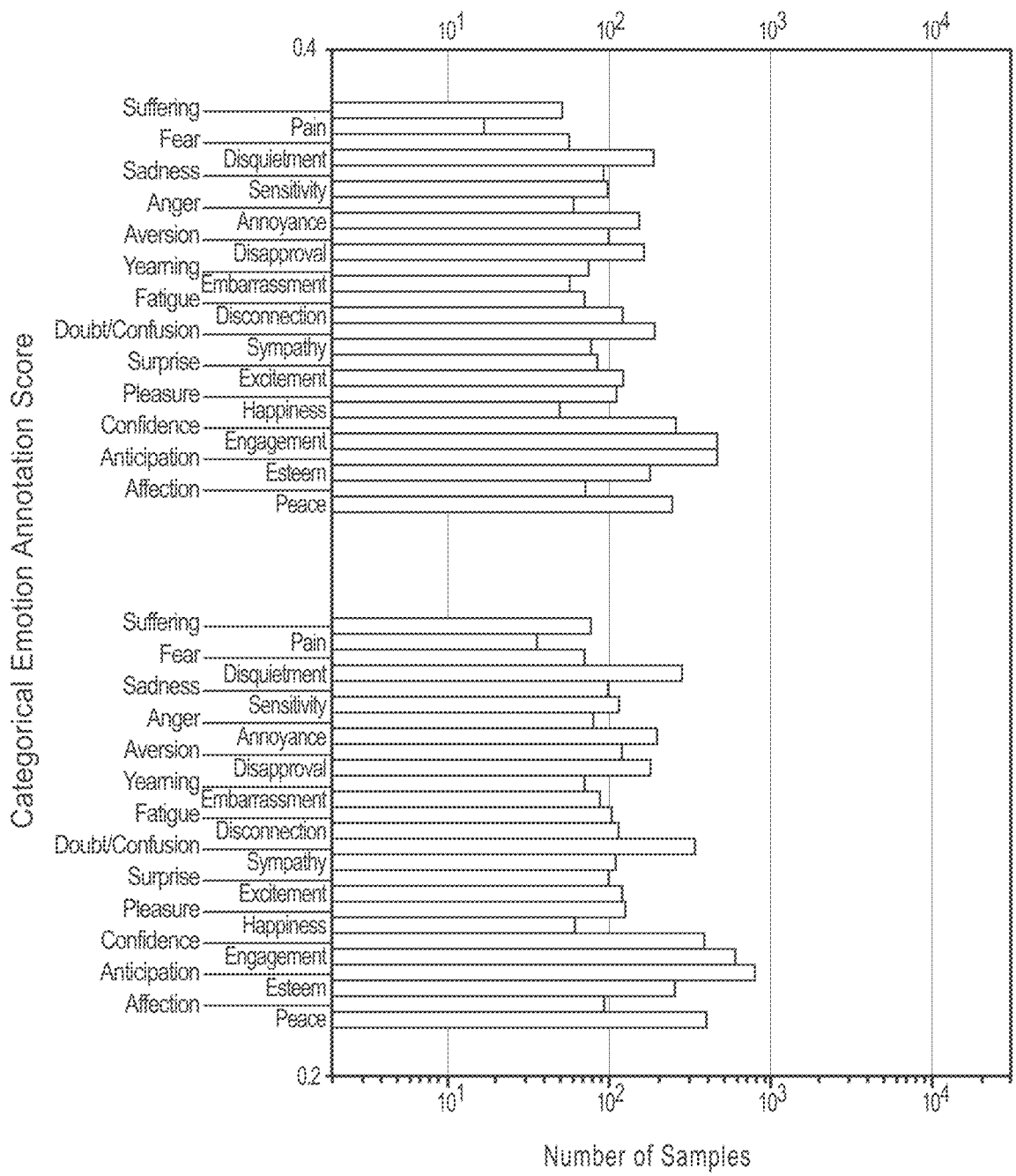
FIG. 7D depicts another bar chart illustrating distributions for each of the twenty-six (26) categorical emotions, according to one or more embodiments of the present disclosure.
Figure 7E:
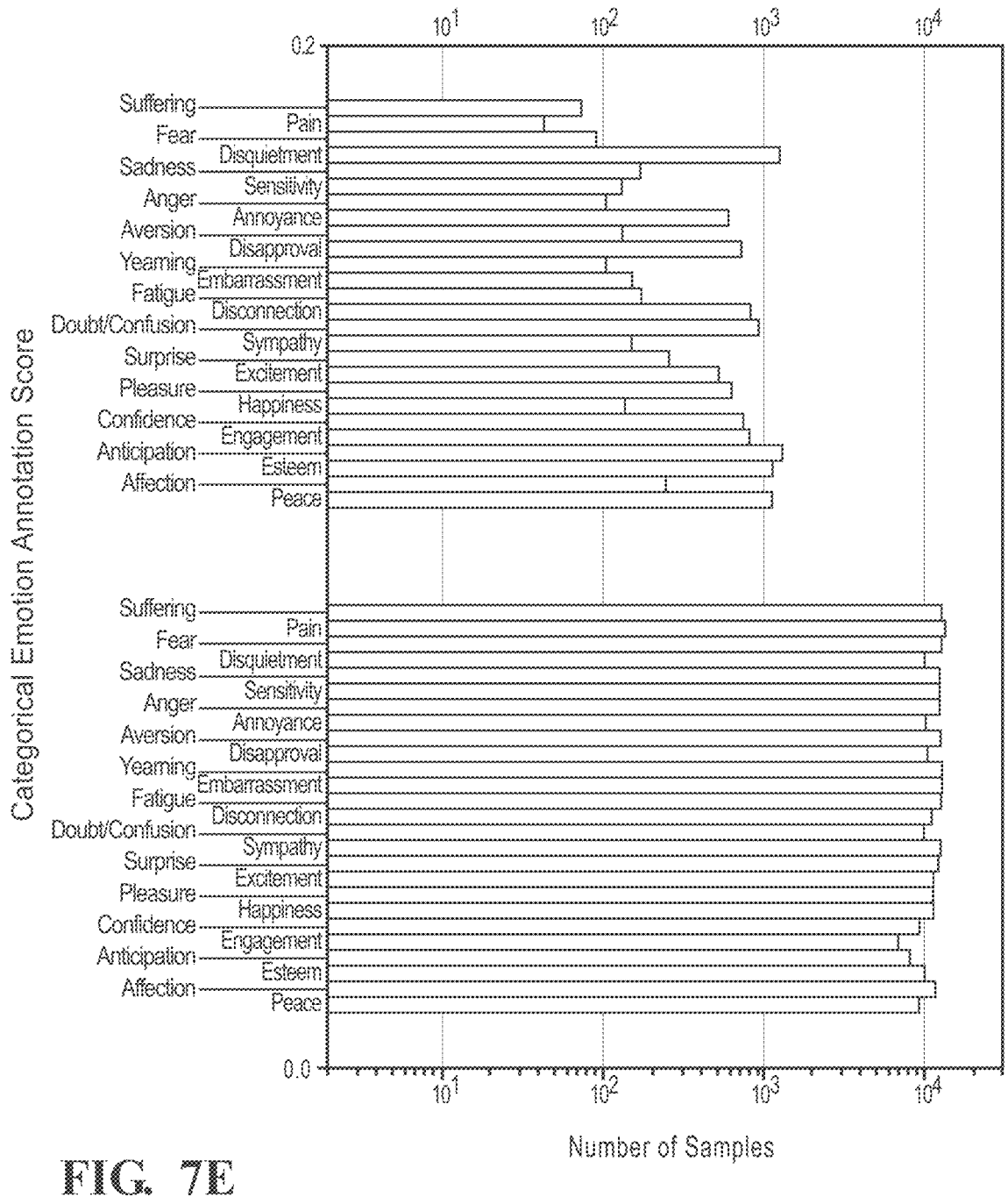
FIG. 7E depicts another bar chart illustrating distributions for each of the twenty-six (26) categorical emotions, according to one or more embodiments of the present disclosure.

Annotations for 13,239 instances have been collected. The dataset continues to grow as more instances and annotations are added. FIGS. 6A-6BB show some high-confidence instances in the BoLD dataset. More specifically, FIGS. 6A-6Z show an instance for each of the 26 categorical emotions (e.g., peace, affection, esteem, anticipation, engagement, confidence, happiness, pleasure, excitement, surprise, sympathy, doubt/confusion, disconnection, fatigue, embarrassment, yearning, disapproval, aversion, annoyance, anger, sensitivity, sadness, disquietment, fear, pain, and suffering) and FIGS. 6AA and 6BB show 2 instances used for quality control. In each of FIGS. 6A-6BB, the left side is a frame from the video, along with another copy that has the character entity IDs marked in a bounding box. The right side shows the corresponding aggregated annotation, annotation confidence c, demographics of the character, and aggregated categorical and dimensional emotion. FIGS. 7A-7E show the distributions of the 26 different categorical emotions. FIG. 8 shows the distributions of the three dimensional emotion ratings: valence, arousal, and dominance. FIGS. 9A, 9B, and 9C show the distributions of the characters in the dataset based on gender, age and ethnicity, respectively. For each categorical emotion, the distribution is highly unbalanced. For dimensional emotion, the distributions of three dimensions are Gaussian-like, while valence is left-skewed and dominance is right-skewed. Character demographics is also unbalanced: most characters in the movie-based dataset are male, white, and adult. All instances are partitioned into three sets: the training set (~70%, 9,222 instances), the validation set (~10%, 1,153 instances), and the testing set (20%, 2,864 instances). The split protocol ensured that clips from the same raw movie video belong to the same set so that subsequent evaluations can be conducted faithfully.

Figure 10:
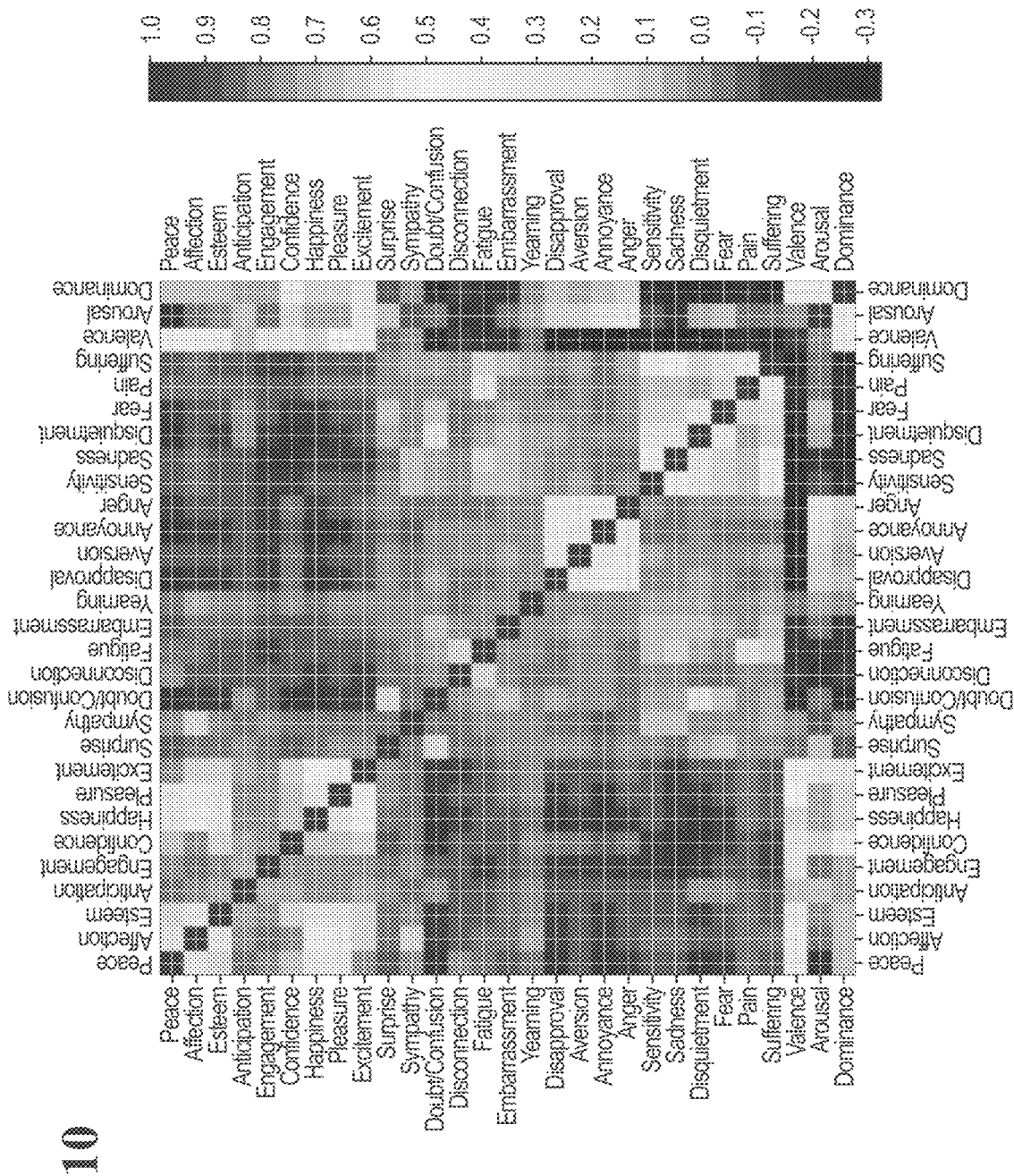
FIG. 10 depicts a graphic illustrating correlations calculated between pairs of categorical emotions and/or dimensional emotions, according to one or more embodiments of the present disclosure.

Correlations between pairs of categorical emotions and pairs of dimensional emotions were observed. FIG. 10 shows correlations between each pair of emotion categories.

Table 1 illustrates the agreement among participants on categorical emotions and characters' demographic information. κ is computed on all collected annotations for each category. For each category, it was treated as a two-category classification and constructed a subject-category table to compute Fleiss' Kappa. By filtering out those with low reliability scores, filtered κ is also computed. Note that some instances may have less than five annotations after removing annotations from low-reliability participants. A means for computing $p_j$ was edited, defined as the proportion of all assignments which were to the j-th category.

TABLE 1

| Category | κ | filtered κ | Category | κ | filtered κ | Category | κ | filtered κ |
|---|---|---|---|---|---|---|---|---|
| Peace | 0.132 | 0.148 | Affection | 0.262 | 0.296 | Esteem | 0.077 | 0.094 |
| Anticipation | 0.071 | 0.078 | Engagement | 0.110 | 0.126 | Confidence | 0.166 | 0.183 |
| Happiness | 0.385 | 0.414 | Pleasure | 0.171 | 0.200 | Excitement | 0.178 | 0.208 |
| Surprise | 0.137 | 0.155 | Sympathy | 0.114 | 0.127 | Doubt/Confusion | 0.127 | 0.141 |
| Disconnection | 0.125 | 0.140 | Fatigue | 0.113 | 0.131 | Embarrassment | 0.066 | 0.085 |
| Yearning | 0.030 | 0.036 | Disapproval | 0.140 | 0.153 | Aversion | 0.075 | 0.087 |
| Annoyance | 0.176 | 0.197 | Anger | 0.287 | 0.307 | Sensitivity | 0.082 | 0.097 |
| Sadness | 0.233 | 0.267 | Disquietment | 0.110 | 0.125 | Fear | 0.193 | 0.214 |
| Pain | 0.273 | 0.312 | Suffering | 0.161 | 0.186 | Average | 0.154 | 0.173 |
| Gender | 0.863 | 0.884 | Age | 0.462 | 0.500 | Ethnicity | 0.410 | 0.466 |

Categorical emotion pairs such as pleasure and happiness (0.57), happiness and excitement (0.40), sadness and suffering (0.39), annoyance and disapproval (0.37), sensitivity and sadness (0.37), and affection and happiness (0.35) show high correlations, matching the intuition. Correlations between dimensional emotions (valence and arousal) are weak (0.007). Because these two dimensions were designed to indicate independent characteristics of emotions, weak correlations among them confirm their validity. However, correlations between valence and dominance (0.359), and between arousal and dominance (0.356) are high. This finding is evidence that dominance is not a strictly independent dimension in the VAD model.

Correlations between dimensional and categorical emotions were also observed. Valence shows strong positive correlations with happiness (0.61) and pleasure (0.51), and strong negative correlations with disapproval (-0.32), sadness (-0.32), annoyance (-0.31), and disquietment (-0.32). Arousal shows positive correlations with excitement (0.25) and anger (0.31), and negative correlations with peace (-0.20), and disconnection (-0.23). Dominance shows strong correlation with confidence (0.40), and strong negative correlation with doubt/confusion (-0.23), sadness (-0.28), fear (-0.23), sensitivity (-0.22), disquietment (-0.24), and suffering (-0.25). All of these correlations match with the intuition about these emotions.

2.2.2 Annotation Quality and Observations

Fleiss' Kappa score (κ) was computed for each categorical emotion and categorical demographic information to understand the extent and reliability of agreement among participants. The Fleiss' Kappa score is described in "Handbook of Inter-rater Reliability: The Definitive Guide to Measuring the Extent of Agreement Among Raters" by Gwet, K L, of Advanced Analytics, LLC, the entire contents of which is hereby incorporated by reference herein. Perfect agreement leads to a score of one, while no agreement leads to a score less than or equal to zero. Table 1 shows Fleiss' Kappa among participants on each categorical emotion and categorical demographic information. Stated differently, Originally, it should be:

$$p_j = \frac{1}{N} \sum_{i=1}^{N} \frac{n_{ij}}{n}, \qquad (3)$$

where N is the number of instances, $n_{ij}$ is the number of ratings annotators have assigned to the j-th category on the i-th instance, and n is the number of annotators per instance. In the filtered κ computation, n varies for different instances and the number of annotators for instance i are denoted as $n_i$. Then Eq. (3) revised as:

$$p_j = \frac{1}{N} \sum_{i=1}^{N} \frac{n_{ij}}{n_i}. \qquad (4)$$

Filtered κ is improved for each category, even for those objective categories like gender, which also suggests the validity of the offline quality control mechanism. Note that the reliability score is computed over dimensional emotions, and thus the offline quality control approach is complementary. As shown in Table 1, affection, anger, sadness, fear, and pain have fair levels of agreement (0.2<κ<0.4). Happiness has moderate level of agreement (0.4<κ<0.6), which is comparable to objective tasks such as age and ethnicity. This result indicates that humans are mostly consistent in their sense of happiness. Other emotion categories fall into the level of slight agreement (0<κ<0.2). The κ score of demographic annotation is as expected in the art. Because the annotation is calculated from the same participant population, κ also represents how difficult or subjective the task is. Evidently gender is the most consistent (hence the easiest) task among all categories. The data confirms that emotion recognition is both challenging and subjective even for human beings with sufficient level of EQ. Participants in the study passed an EQ test designed to measure one's ability to sense others' feelings as well as response to others' feelings.

For dimensional emotions, both across-annotation variances and within-instance annotation variances were computed. The variances across all annotations are 5.87, 6.66, and 6.40 for valence, arousal, and dominance, respectively. Within-instance variances (over different annotators) is computed for each instance and the means of these variances are 3.79, 5.24, and 4.96, respectively. Notice that for the dimensions, the variances are reduced by 35%, 21%, and 23%, respectively, which illustrates human performance at reducing variance given concrete examples. Interestingly, participants are better at recognizing positive and negative emotions (e.g., valence) than in other dimensions.

2.2.3 Human Performance

Figure 11:
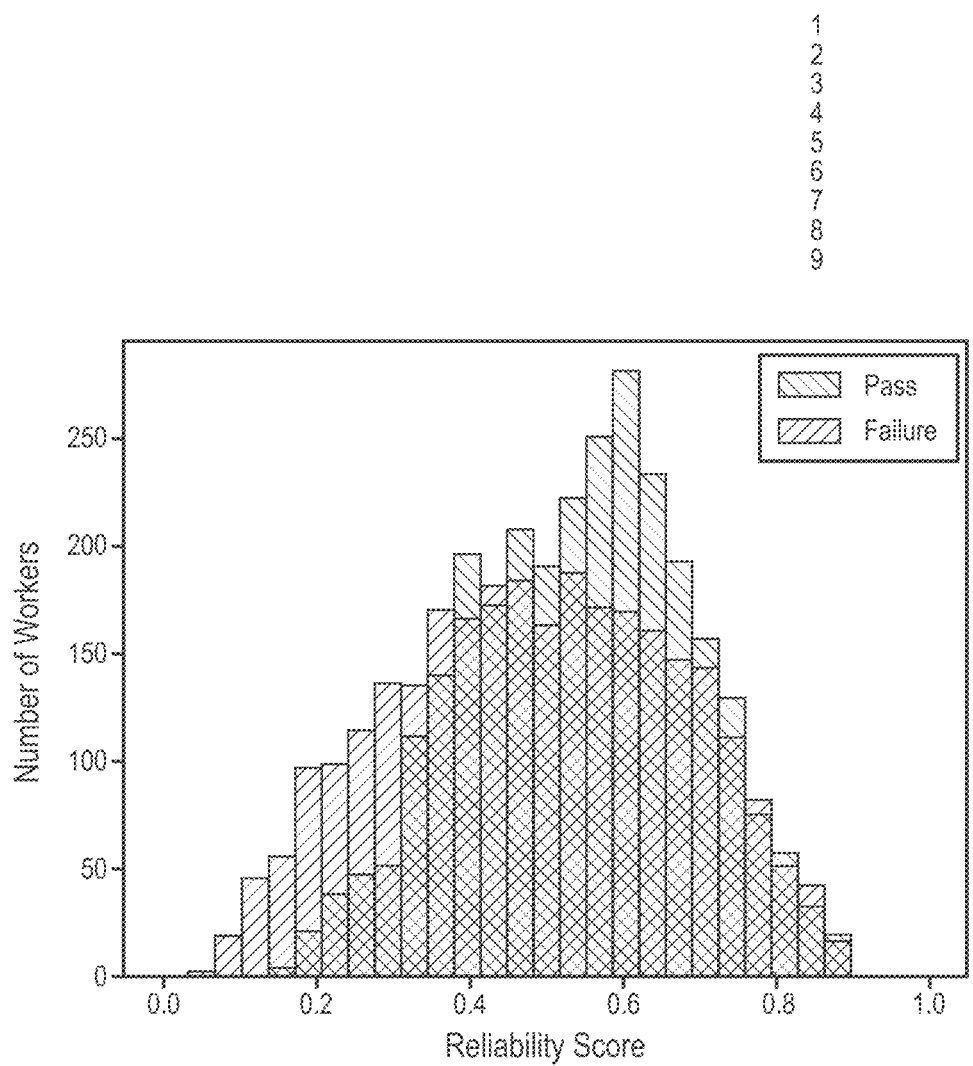
FIG. 11 depicts a bar chart illustrating reliability score distribution among low-performance participants and non low-performance participants, according to one or more embodiments of the present disclosure.

The difference between low-performance participants and low reliability-score participants were explored. FIG. 11 depicts a bar chart illustrating reliability score distribution among low-performance participants (failure) and non low-performance participants (pass). As shown in FIG. 11, low-performance participants show lower reliability score by average. While a significantly large number of low-performance participants have rather high reliability scores, most non-low-performance participants have reliability scores larger than 0.33. These distributions suggest that participants who pass annotation sanity checks and relaxed gold standard tests are more likely to be reliable. However, participants who fail at those tests may still be reliable. Therefore, conventional quality control mechanism like the gold standard is insufficient when it comes to affect data.

Figure 12D:
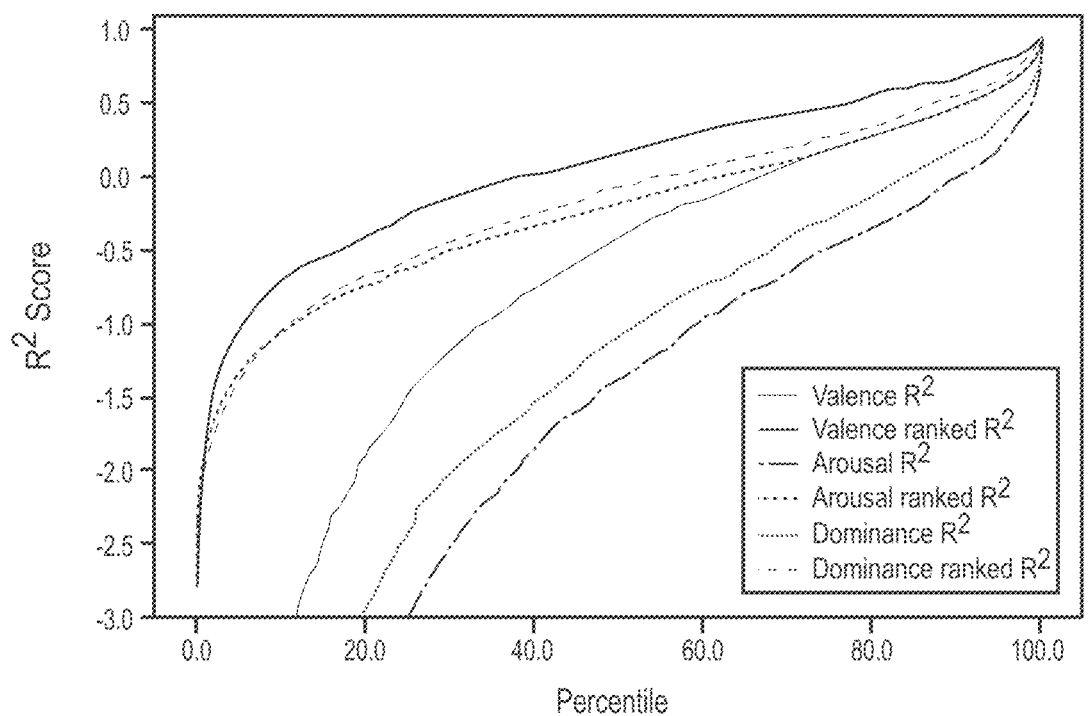
FIG. 12D depicts an illustrative $R^2$ score versus participant population percentile plot for dimensional emotions including valence, arousal and dominance, according to one or more embodiments of the present disclosure.
Figure 12E:
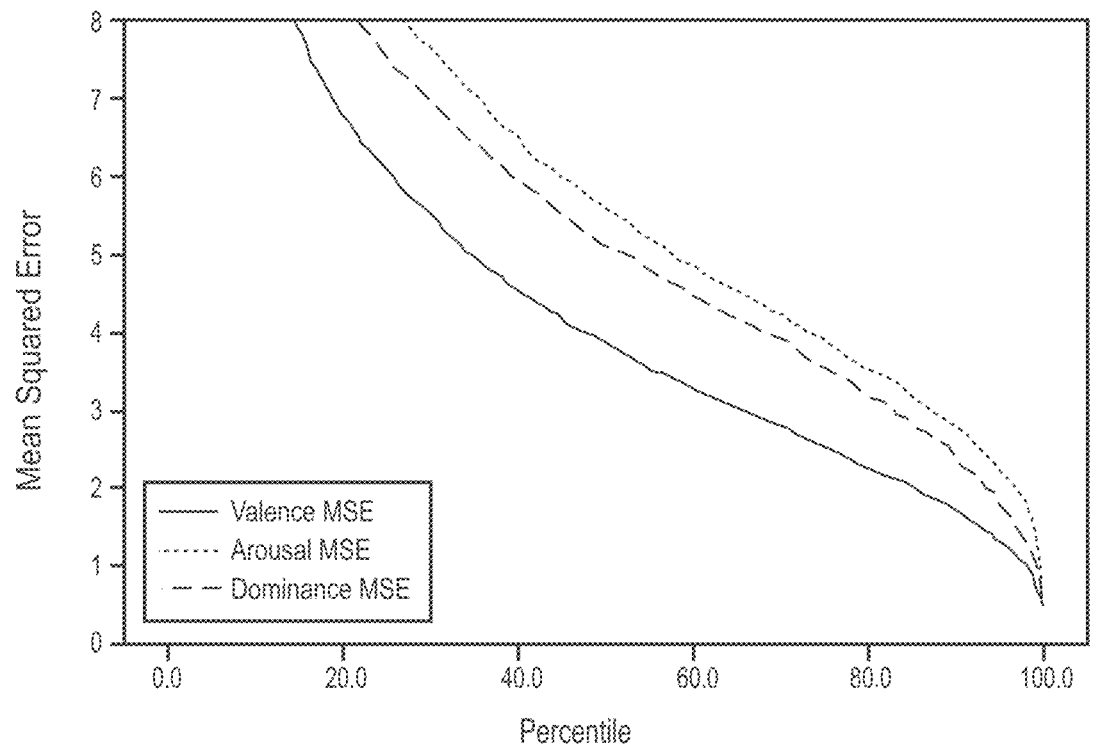
FIG. 12E depicts an illustrative MSE versus participant population percentile plot for dimensional emotions including valence, arousal and dominance, according to one or more embodiments of the present disclosure.

In addition, an investigation was conducted into how well humans can achieve on emotion recognition tasks. There are 5,650 AMT participants contributing to the dataset annotation. They represent over 100 countries (including 3,421 from the USA and 1,119 from India), with 48.4% male and 51.6% female, and an average age of 32. In terms of ethnicity, 57.3% self-reported as White, 21.2% Asian, 7.8% African American, 7.1% Hispanic or Latino, 1.6% American Indian or Alaskan Native, 0.4% Native Hawaiian or Other Pacific Islander, and 4.5% Other. For each participant, annotations from other participants were used and final dataset annotation was aggregated to evaluate the performance. This participant's annotation was treated as prediction from an oracle model and calculate F1 score for categorical emotion, and coefficient of determination ($R^2$) and mean squared error (MSE) for dimensional emotion to evaluate the participant's performance. Similar to the standard annotation aggregation procedure, instances with a confidence score less than 0.95 was ignored when dealing with dimensional emotions. FIGS. 12A-12E depict plots illustrating human regression performance on dimensional emotions. In each plot, the X-axis depicts participant population percentile and the Y-axis depicts F1 scores (e.g., FIGS. 12A, 12B and 12C), R2 (e.g., FIG. 12D) and MSE (e.g., FIG. 12E), respectively. The tables corresponding to FIGS. 12D and 12E summarize top 30%, 20%, 10% and 5% participant regression scores. More simply, FIGS. 12A-12E show the cumulative distribution of participants' F1 scores of categorical emotions, the $R^2$ score, and the MSE score of dimensional emotion, respectively. Vanilla $R^2$ score was calculated and percentile-based $R^2$ score was ranked. For the latter, rank percentile was used for both prediction and the ground truth. The areas under the curves (excluding FIG. 12E) can be interpreted as how difficult it is for humans to recognize the emotion. For example, humans are effective at recognizing happiness while ineffective at recognizing yearning. Similarly, humans are better at recognizing the level of valence than that of arousal or dominance. These results reflect the challenge of achieving high classification and regression performance for emotion recognition even for human beings.

2.2.4 Demographic Factors

Culture, gender, and age could be important factors of emotion understanding. As mentioned herein (e.g., 2.1.4 Annotation Quality Control Section), nine quality control videos exist in the crowdsourcing process that have been annotated for emotion more than 300 times. These quality control videos were used to test whether the annotations are independent of annotators' culture, gender, and age.

For categorical annotations (including both categorical emotions and categorical character demographics), a $\chi^2$ test was conducted on each video. For each control instance, the p-value of the $\chi^2$ test over annotations (26 categorical emotions and 3 character demographic factors) was calculated from different groups resulting from annotators' three demographic factors. This process results in 29×3=87 p-value scores for each control instance. For each test among 87 pairs, the total number of videos with significant p-value (p<0.01 or p<0.001) were counted. There is significant dependence over characters' ethnicity and annotators' ethnicity (9 out of 9, p<0.001). It is possible that humans are good at recognizing the ethnicity of others in the same ethnic group. Additionally, there is intermediate dependence between annotators' ethnicity and categorical emotions (17 out of 26×9=234, p<0.001). A strong dependence over other tested pairs (less than 3 out of 9, p<0.001) was not found. This lack of dependence seems to suggest that a person's understanding of emotions depends more on their own ethnicity than on their age or gender.

For VAD annotation, one-way ANOVA tests were conducted on each instance. For each control instance, a p-value of one-way ANOVA test was calculated over VAD (3) annotations from different groups resulting from annotators' demographic factors (3). This results in 3×3=9 p-value scores for each control instance. Kruskal-Wallis H-test was conducted and similar results were found. The t p-value of one-way ANOVA tests is reported. The results show that gender and age have little effect (less than 8 out of 9×(3+3)=54, p<0.001) on emotion understanding, while ethnicity has a strong effect (13 out of 9×3=27, p<0.001) on emotion understanding. Specifically, participants with different ethnicities have different understandings regarding valence for almost all control clips (7 out of 9, p<0.001). FIGS. 6AA and 6BB show two control clips. For FIG. 6AA, valence average of person 0 among Asians is 5.56, yet 4.12 among African Americans and 4.41 among Whites. However, arousal average among Asians is 7.20, yet 8.27 among African Americans and 8.21 among Whites. For FIG. 6BB, valence average of person 1 among Asians is 6.30, yet 5.09 among African Americans and 4.97 among Whites. However, arousal average among Asians is 7.20, yet 8.27 among African Americans and 8.21 among Whites. Among all of the control instances, the average valence among Asians is consistently higher than among Whites and African Americans. This repeated finding seems to suggest that Asians tend to assume more positively when interpreting others' emotions.

2.2.5 Discussion

The data collection efforts offer important lessons. The efforts confirmed that reliability analysis is useful for collecting subjective annotations such as emotion labels when no gold standard ground truth is available. As shown in Table 1, consensus (filtered κ value) over high-reliable participants is higher than that of all participants (κ value). This finding holds for both subjective questions (categorical emotion) and objective questions (character demographics), even though the reliability score is calculated with the different VAD annotations—as evidence that the score does not overfit. As an offline quality control component, the method developed and used to generate reliability scores developed herein is suitable for analyzing such affective data. For example, one can also apply the proposed data collection pipeline to collect data for the task of image aesthetics modeling. In addition to their effectiveness in quality control, reliability scores are very useful for resource allocation. With a limited annotation budget, it is more reasonable to reward highly-reliable participants rather than less reliable ones.

3.0 BODILY EXPRESSION RECOGNITION

In this section, two pipelines for automated recognition of bodily expression and present quantitative results are investigated for some baseline methods. Unlike AMT participants, who were provided with all the information regardless of whether they use all in their annotation process, the first computerized pipeline (e.g., that learns from skeleton) relied solely on body movements, but not on facial expressions, audio, or context. The second pipeline (e.g., that learns from pixels) took a sequence of cropped images of the human body as input, without explicitly modeling facial expressions.

3.1 Learning from Skeleton
3.1.1 Laban Movement Analysis

Laban notation has been used for documenting body movement of dancing such as ballet. Laban movement analysis (LMA) uses the components to record human body movements: body, effort, shape, and space. Body category represents structural and physical characteristics of the human body movements. It describes which body parts are moving, which parts are connected, which parts are influenced by others, and general statements about body organization. Effort category describes inherent intention of a movement. Shape describes static body shapes, the way the body interacts with something, the way the body changes toward some point in space, and the way the torso changes in shape to support movements in the rest of the body. LMA or its equivalent notation systems have been used in psychology for emotion analysis and human computer interaction for emotion generation and classification. According to aspects of the present disclosure, features listed in Table 2 below are used. More specifically, Table 2 illustrates Laban Movement Analysis (LMA) features. In view of Table 2, $f_i$ references categories, m references a number of measurements, dist. references distance, and accel. references acceleration.

TABLE 2

| $f_i$ | Description | m |
|---|---|---|
| $f_1$ | Feet-hip dist. | 4 |
| $f_3$ | Hands dist. | 4 |
| $f_8$ | Centroid-pelvis dist. | 4 |
| $f_{29}$ | Shoulders velocity | 4 |
| $f_{13}$ | Hands velocity | 4 |
| $f_{35}$ | Knee velocity | 4 |
| $f_{38}$ | Angular velocity | $4C_{23}^2$ |
| $f_{30}$ | Shoulders accel. | 4 |
| $f_{16}$ | Hands accel. | 4 |
| $f_{36}$ | Knee accel. | 4 |
| $f_{39}$ | Angular accel. | $4C_{23}^2$ |
| $f_{31}$ | Shoulders jerk | 4 |
| $f_{40}$ | Hands jerk | 4 |
| $f_{37}$ | Knee jerk | 4 |
| $f_{19}$ | Volume | 4 |
| $f_{21}$ | Volume (lower body) | 4 |
| $f_{23}$ | Volume (right side) | 4 |
| $f_2$ | Hands-shoulder dist. | 4 |
| $f_4$ | Hands-head dist. | 4 |
| $f_9$ | Gait size (foot dist.) | 4 |
| $f_{32}$ | Elbow velocity | 4 |
| $f_{12}$ | Hip velocity | 4 |
| $f_{14}$ | Feet velocity | 4 |
| $f_{33}$ | Elbow accel. | 4 |
| $f_{15}$ | Hip accel. | 4 |
| $f_{17}$ | Feet accel. | 4 |
| $f_{34}$ | Elbow jerk | 4 |
| $f_{18}$ | Hip jerk | 4 |
| $f_{41}$ | Feet jerk | 4 |
| $f_{20}$ | Volume (upper body) | 4 |
| $f_{22}$ | Volume (left side) | 4 |
| $f_{24}$ | Torso height | 4 |

Conventionally, LMA is conducted for 3D motion capture data that have 3D coordinates of body landmarks. According to aspects of the present disclosure, 2D pose on images is estimated. One example method for estimating 2D poses on images is described in "Realtime Multi-person 2D Pose Estimation Using Part Affinity Fields" by Cao et al., of Proceedings of the IEEE Conference on Computer Vision and Pattern Recognition, the entire contents of which is hereby incorporated by reference herein. In particular, $p_i^t \in R^2$ is denoted as the coordinate of the i-th joint at the t-th frame. As the nature of the data, the 2D pose estimation usually has missing values of joint locations and varies in scale. In the implementation, an instance is ignored if the dependencies to compute the feature are missing. To address the scaling issue, each pose is normalized by the average length of all visible limbs, such as shoulder-elbow and elbow-wrist. Let $v=\{(i, j) | \text{joint } i \text{ and joint } j \text{ are visible}\}$ be the visible set of the instance. The normalized pose $\hat{p}_i^t$ is computed by:

$$s = \frac{1}{T|v|} \sum_{(i,j) \in v} \sum_t^T \|p_i^t - p_j^t\|, \quad \hat{p}_i^t = \frac{p_i^t}{s}. \tag{5}$$

The first part of features in LMA, body component, captures the pose configuration. For $f_1$, $f_2$, $f_3$, $f_8$, and $f_9$, the distance between the specified joints is computed frame by frame. For symmetric joints like feet-hip distance, the mean of left-feat-hip and right-feat-hip distance is used in each frame. The same protocol was applied to other features that contain symmetric joints like hands velocity. For $f_4$, the centroid was averaged over all visible joints and pelvis is the midpoint between left hip and right hip. This feature is designed to represent barycenter deviation of the body.

The second part of features in LMA, effort component, captures body motion characteristics. Based on the normalized pose, joints velocity $\hat{v}_i^t$, acceleration $\hat{a}_i^t$, and jerk $\hat{j}_i^t$ were computed as:

$$v_i^t = \frac{\hat{p}_i^{t+\tau} - \hat{p}_i^t}{\tau}, \quad a_i^t = \frac{v_i^{t+\tau} - v_i^t}{\tau}, \quad j_i^t = \frac{a_i^{t+\tau} - a_i^t}{\tau}, \quad \hat{v}_i^t = \|v_i^t\|, \quad \hat{a}_i^t = \|a_i^t\|, \quad \hat{j}_i^t = \|j_i^t\|. \tag{6}$$

Figure 13A:
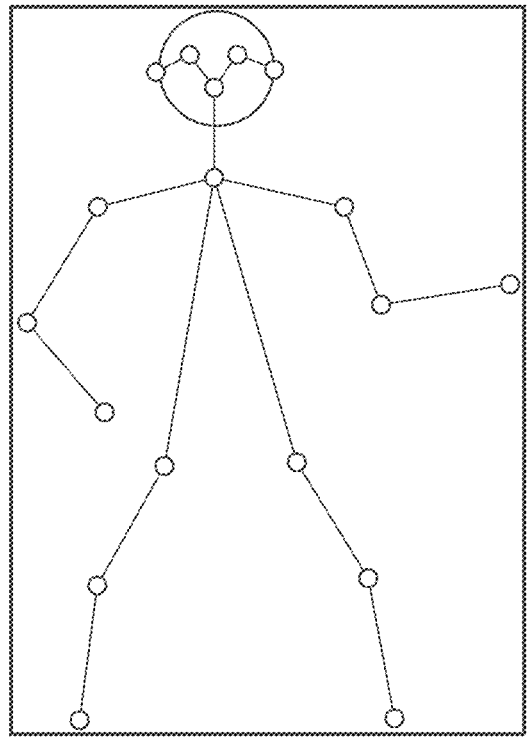
FIG. 13A depicts illustrative joints and limbs of a natural human skeleton, according to one or more embodiments of the present disclosure.
Figure 13B:
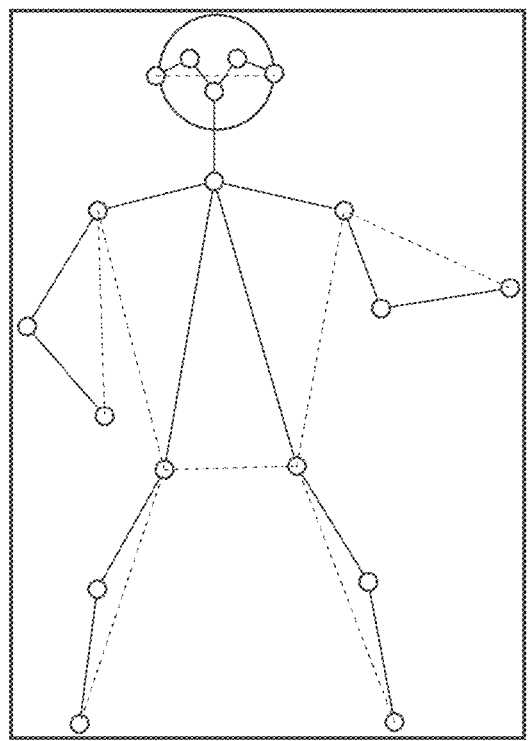
FIG. 13B depicts illustrative joints and limbs usable in feature extraction, according to one or more embodiments of the present disclosure.
Figure 14A:
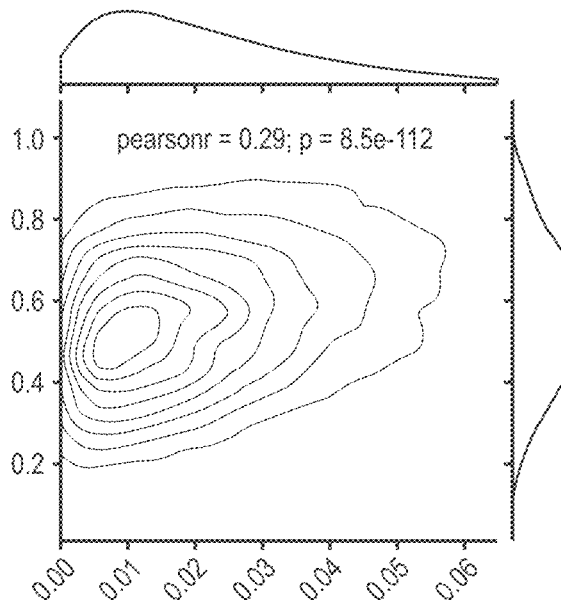
FIG. 14A depicts an illustrative kernel density estimation plot that indicates the hands velocity feature, $f_{13}^{mean}$, as having a high correlation with arousal, according to one or more embodiments of the present disclosure.
Figure 14B:
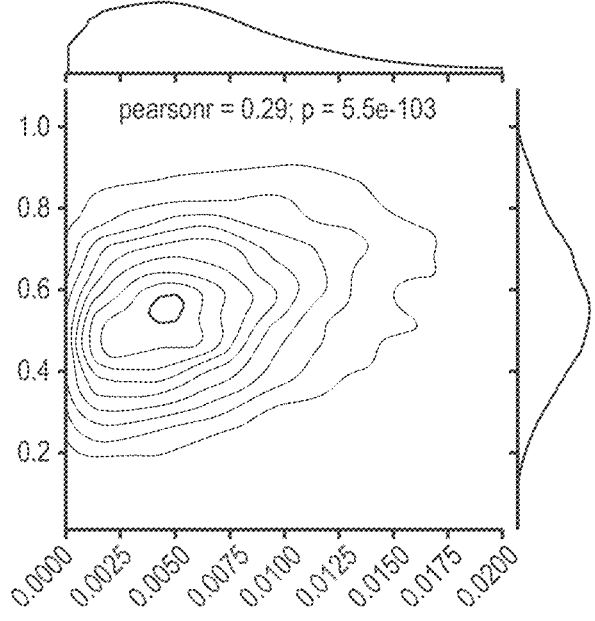
FIG. 14B depicts an illustrative kernel density estimation plot that indicates the hands acceleration feature, $f_{16}^{max}$, as having a high correlation with arousal, according to one or more embodiments of the present disclosure.
Figure 14C:
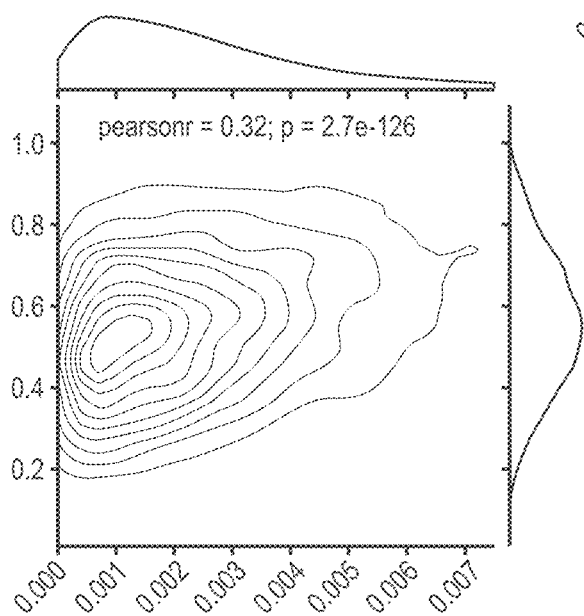
FIG. 14C depicts an illustrative kernel density estimation plot that indicates the hands acceleration feature, $f_{16}^{mean}$, as having a high correlation with arousal, according to one or more embodiments of the present disclosure.
Figure 14D:
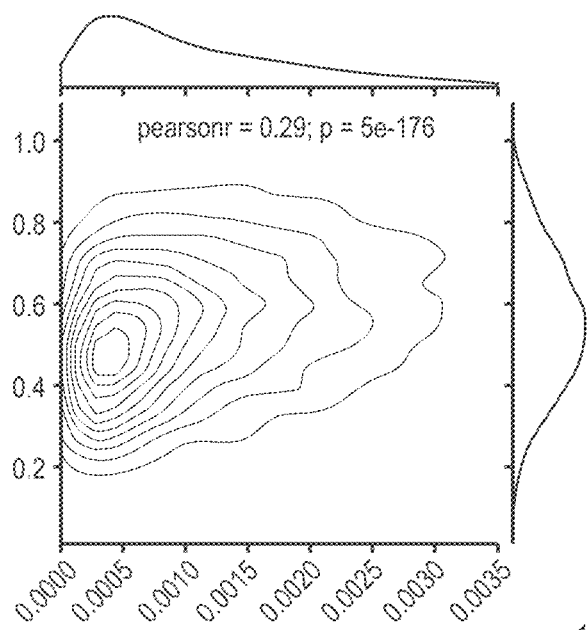
FIG. 14D depicts an illustrative kernel density estimation plot that indicates the shoulders acceleration feature, $f_{30}^{mean}$, having a high correlation with arousal, according to one or more embodiments of the present disclosure.
Figure 14E:
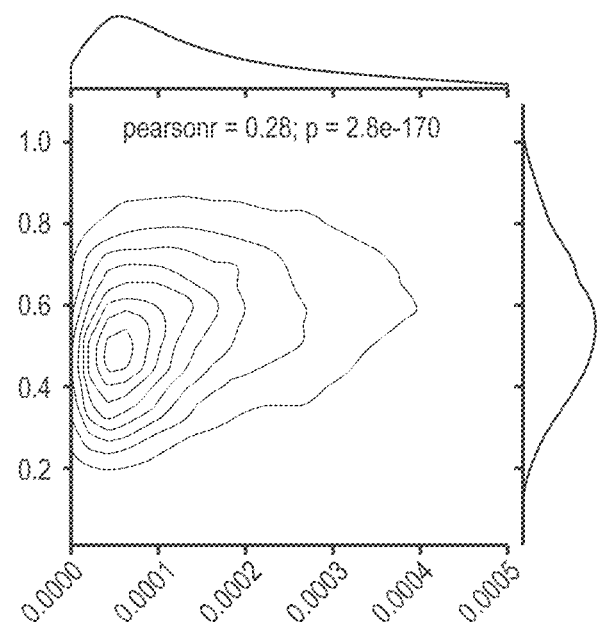
FIG. 14E depicts an illustrative kernel density estimation plot that indicates the shoulders jerk feature, $f_{31}^{mean}$, as having a high correlation with arousal, according to one or more embodiments of the present disclosure.
Figure 14F:
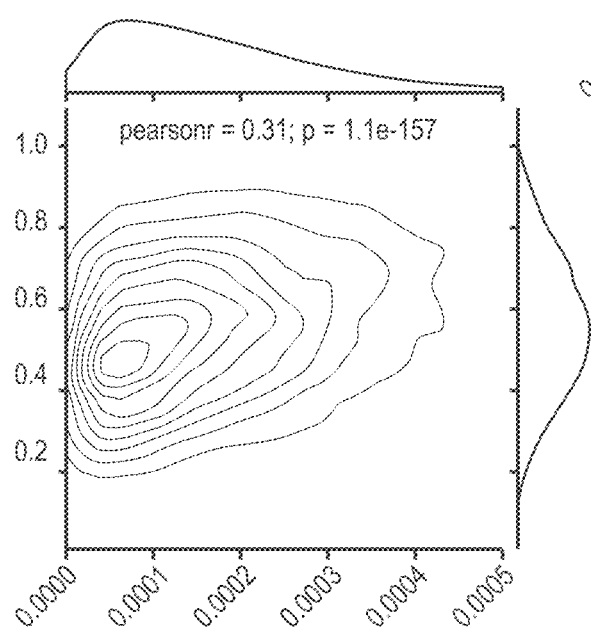
FIG. 14F depicts an illustrative kernel density estimation plot that indicates the elbow acceleration feature, $f_{33}^{mean}$, having a high correlation with arousal, according to one or more embodiments of the present disclosure.
Figure 14G:
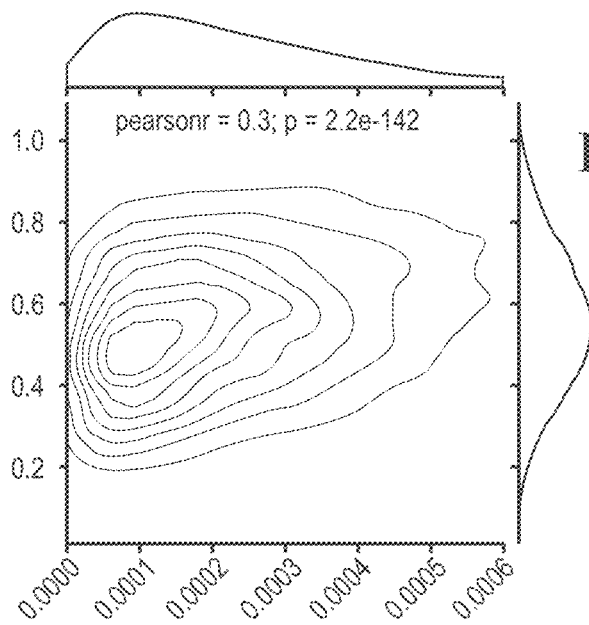
FIG. 14G depicts an illustrative kernel density estimation plot that indicates the elbow jerk feature, $f_{34}^{mean}$, as having a high correlation with arousal, according to one or more embodiments of the present disclosure.
Figure 14H:
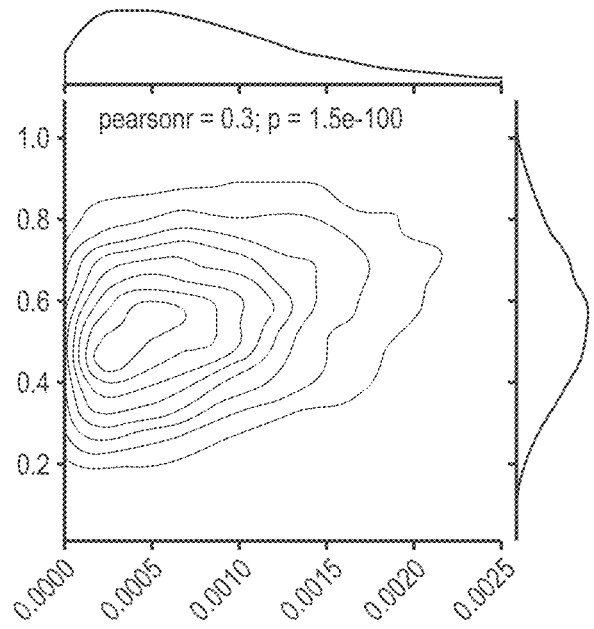
FIG. 14H depicts an illustrative kernel density estimation plot that indicates the hands jerk feature, $f_{40}^{max}$, as having a high correlation with arousal, according to one or more embodiments of the present disclosure.
Figure 14I:
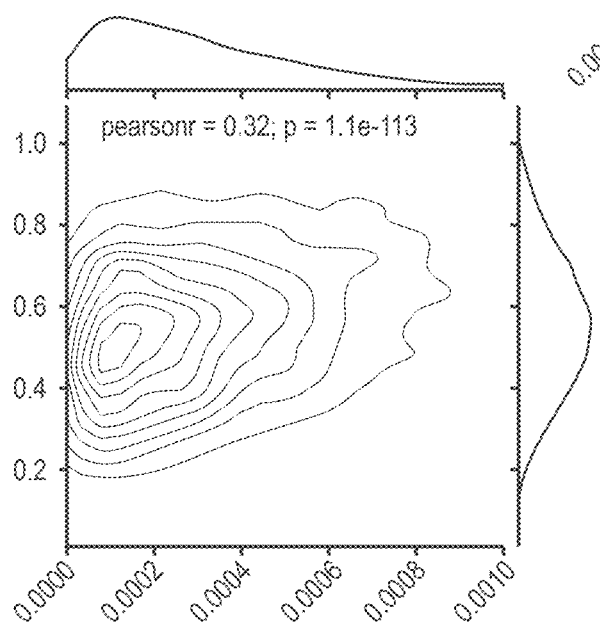
FIG. 14I depicts an illustrative kernel density estimation plot that indicates the hands jerk feature, $f_{40}^{mean}$, as having a high correlation with arousal, according to one or more embodiments of the present disclosure.
Figure 15A:
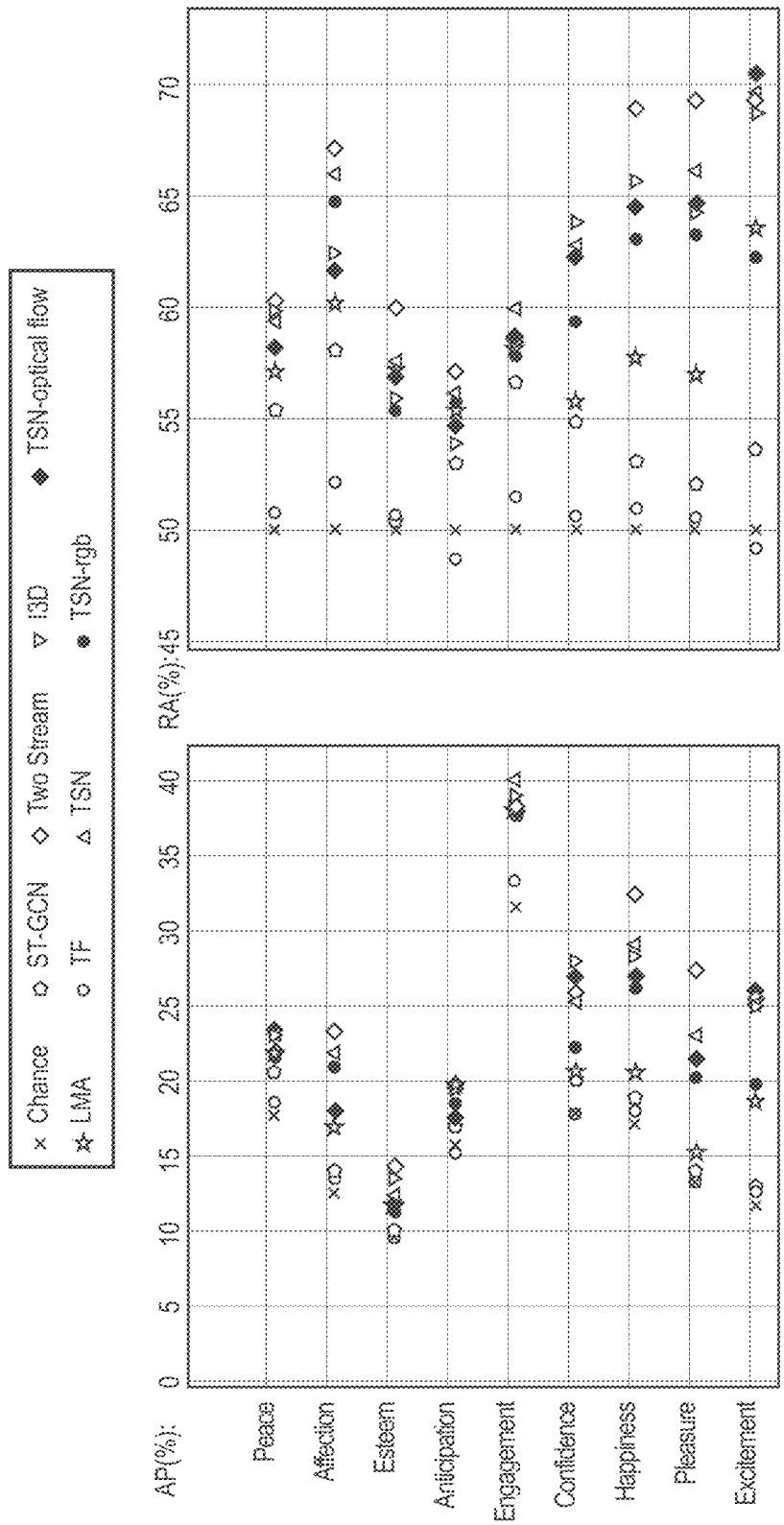
FIG. 15A depicts a graphic illustrating classification performance and regression performance of the various methods on each categorical emotion and dimensional emotion.
Figure 15B:
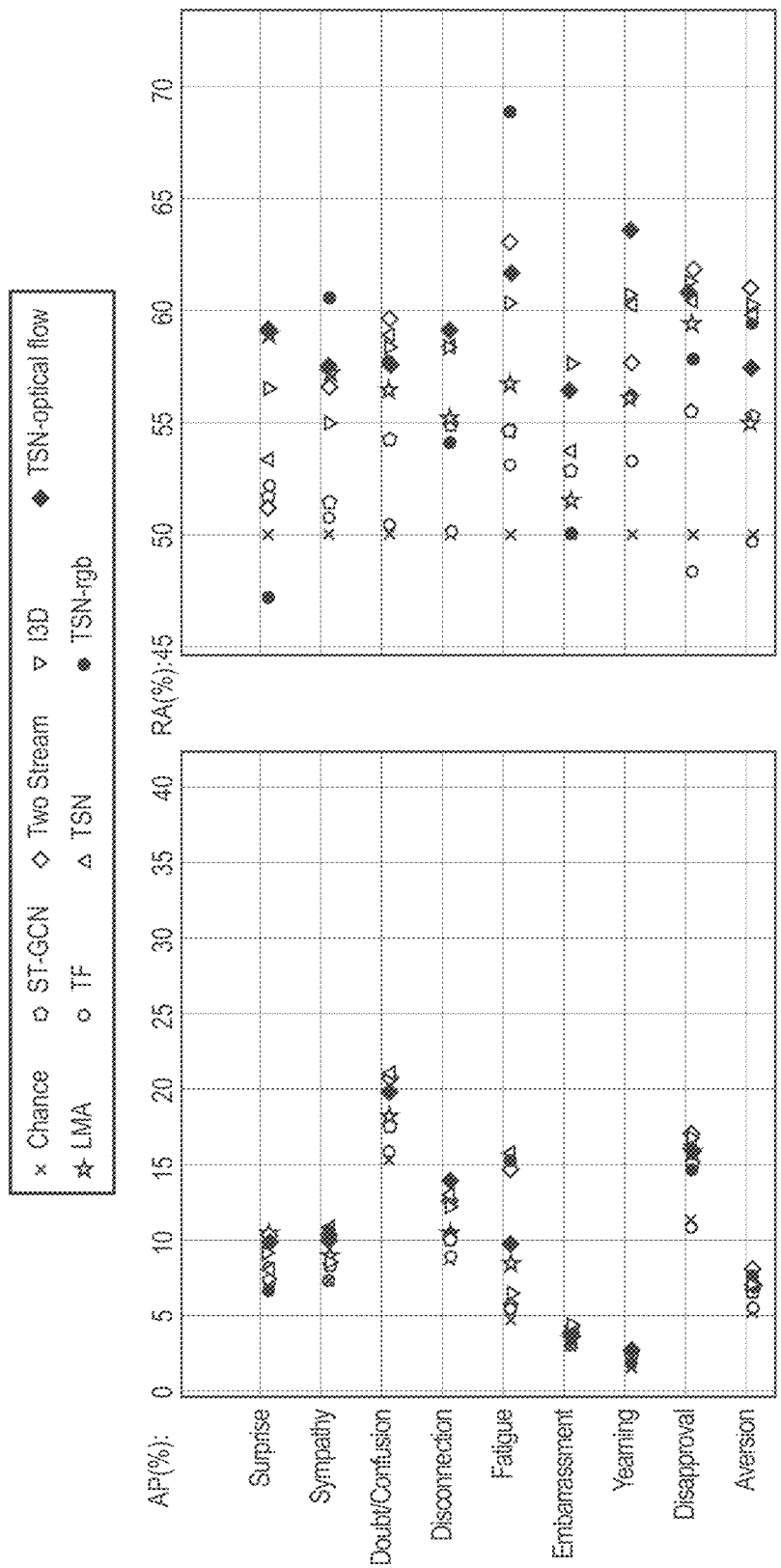
FIG. 15B depicts another graphic illustrating classification performance and regression performance of the various methods on each categorical emotion and dimensional emotion.
Figure 15C:
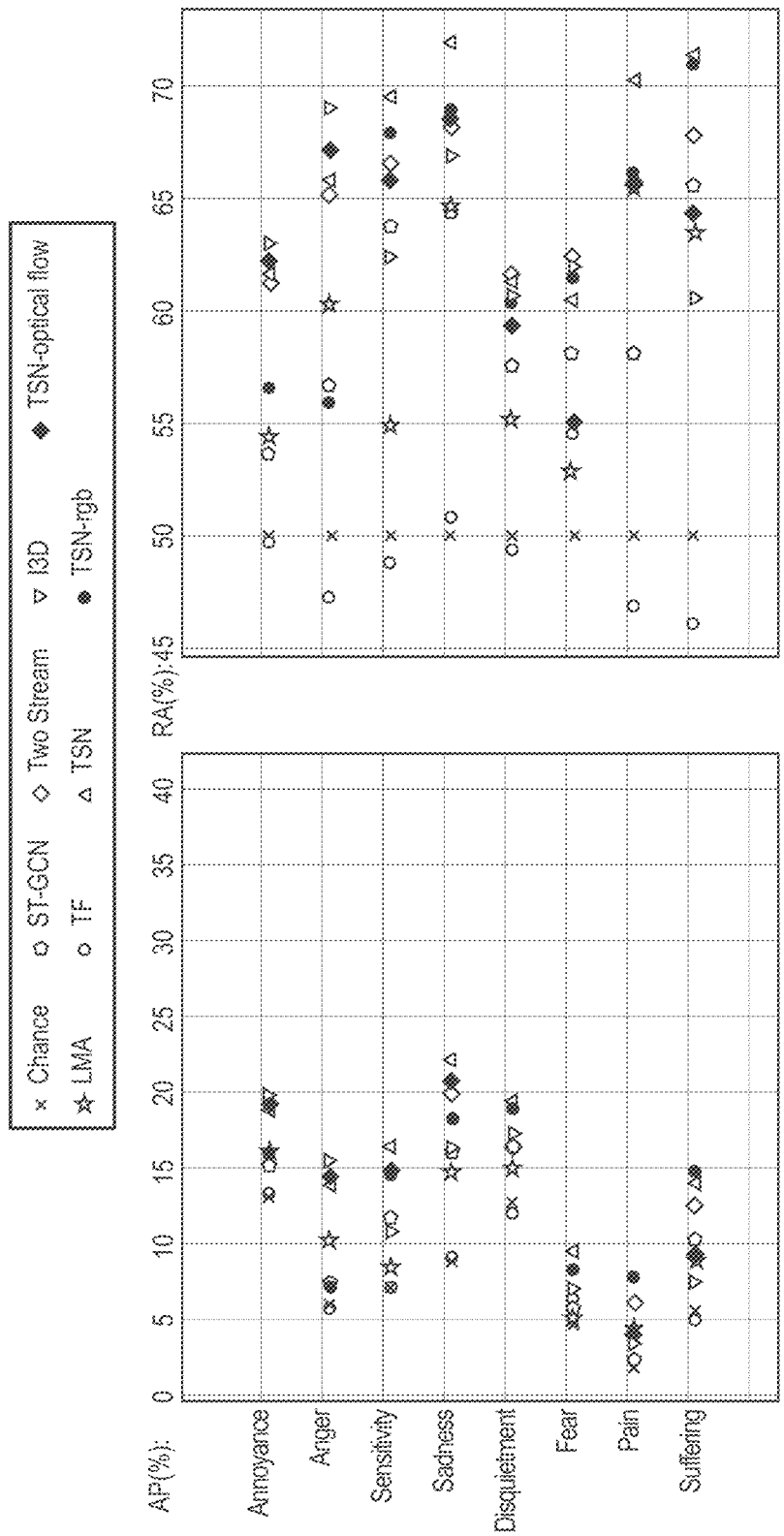
FIG. 15C depicts another graphic illustrating classification performance and regression performance of the various methods on each categorical emotion and dimensional emotion.
Figure 15D:
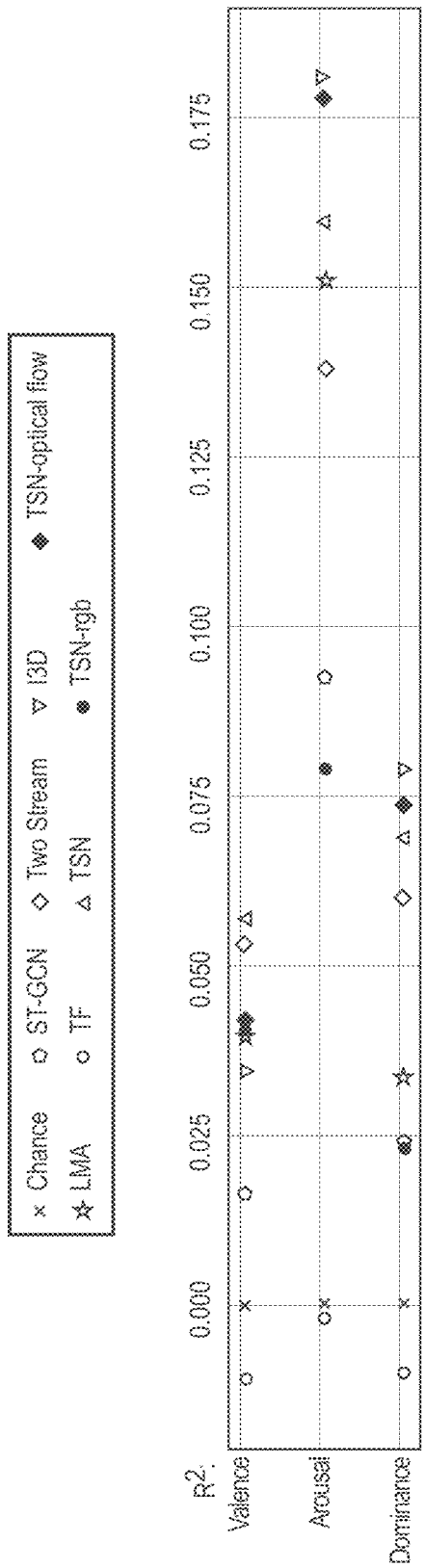
FIG. 15D depicts another graphic illustrating classification performance and regression performance of the various methods on each categorical emotion and dimensional emotion.

FIG. 13A depicts illustrative joints and limbs (e.g., black lines considered limbs) of a natural human skeleton and FIG. 13B depicts illustrative joints and limbs (e.g., black and red lines considered limbs) usable in feature extraction, according to one or more embodiments of the present disclosure. Angles (e.g., θ), angular velocity (e.g., ω), and angular acceleration (e.g., α) between each pair of limbs were calculated for each pose:

$$\theta^t(i,j,m,n) = \arccos\left(\frac{(\hat{p}_i^t - \hat{p}_j^t) \cdot (\hat{p}_m^t - \hat{p}_n^t)}{\|\hat{p}_i^t - \hat{p}_j^t\| \|\hat{p}_m^t - \hat{p}_n^t\|}\right), \quad (7)$$

$$\omega_k^t(i,j,m,n) = \frac{\theta^{t+\tau}(i,j,m,n) - \theta^t(i,j,m,n)}{\tau},$$

$$\alpha_k^t(i,j,m,n) = \frac{\omega^{t+\tau}(i,j,m,n) - \omega^t(i,j,m,n)}{\tau}.$$

Velocity, acceleration, jerk, angular velocity, and angular acceleration of joints is computed τ=15. Empirically, features become less effective when τ is too small (1~2) or too large (>30).

The third part of features in LMA, shape component, captures body shape. For $f_{19}$, $f_{20}$, $f_{21}$, $f_{22}$, and $f_{23}$, the area of bounding box that contains corresponding joints is used to approximate volume.

Finally, all features are summarized by their basic statistics (e.g., maximum, minimum, mean, and standard deviation, denoted as $f_i^{max}$, $f_i^{min}$, $f_i^{mean}$ and $f_i^{std}$, respectively) over time.

With all LMA features combined, each skeleton sequence can be represented by a 2,216-D feature vector. Classification and regression models are built for bodily expression recognition tasks. Because some measurements in the feature set can be linearly correlated and features can be missing, the random forest is chosen for the classification and regression task. Specifically, missing feature values are imputed with a large number (e.g., 1,000). Model parameters are searched with cross validation on the combined set of training and validation. Finally, the selected best parameter is used to retrain a model on the combined set.

3.1.2 Spatial Temporal Graph Convolutional Network

Besides handcrafted LMA features, an end-to-end feature learning method was used for experimentation. In some aspects, human body landmarks can be constructed as a graph with their natural connectivity. Considering the time dimension, a skeleton sequence could be represented with a spatiotemporal graph. Graph convolution may be used as building blocks in Spatial Temporal Graph Convolutional Networks (ST-GCN). ST-GCN has been proposed for skeleton action recognition. According to aspects of the present disclosure, each skeleton sequence is first normalized between 0 and 1 with the largest bounding box of skeleton sequence. Missing joints are filled with zeros. According to various aspects, an architecture may be used and the task may be trained with binary cross-entropy loss and mean-squared-error loss. One example architecture is disclosed in "Spatial Temporal Graph Convolutional Networks for Skeleton-Based Action Recognition" by Yan et al., of Proceedings of the AAAI Conference on Artificial Intelligence, the entire contents of which is hereby incorporated by reference herein. According to the present disclosure, the learning objective f can be written as:

$$\mathcal{L}_{cat} = \sum_{i=1}^{26} y_i^{cat} \log x_i + (1 - y_i^{cat}) \log(1 - x_i^{cat}), \quad (8)$$

-continued $$\mathcal{L}_{cont} = \sum_{i=1}^{3} (y_i^{cont} - x_i^{cont})^2,$$

$$\mathcal{L} = \mathcal{L}_{cat} + \mathcal{L}_{cont},$$

where $x_i^{cat}$ and $y_i^{cat}$ are predicted probability and ground truth, respectively, for the i-th categorical emotion, and $x_i^{cont}$ and $y_i^{cont}$ are model prediction and ground truth, respectively, for the i-th dimensional emotion.

3.2 Learning from Pixels

Essentially, bodily expression may be expressed through body activities. Activity recognition is a conventional task in computer vision. The goal is to classify human activities, like sports and housework, from videos. However, according to aspects of the present disclosure, various human activity recognition methods may be used to extract features. Example activity recognition methods include those disclosed in "Efficient Feature Extraction, Encoding and Classification for Action Recognition" by Kantorov et al., of Proceedings of the IEEE Conference on Computer Vision an Pattern Recognition, "Two Stream Convolutional Networks for Action Recognition in Videos", by Simonyan et al., of Advances in Neural Information Processing Systems, "Temporal Segment Networks: Towards Good Practices for Deep Action Recognition", by Wang et al., of European Conference on Computer Vision, and "Quo Vadis, Action Recognition? A New Model and the Kinetics Dataset", by Carreira et al., of Proceedings of the IEEE Conference on Computer Vision and Pattern Recognition, the entire contents of each are each hereby incorporated by reference herein. According to other aspects, activity recognition may be achieved by two-stream network-based deep-learning methods. One example two-stream network-based deep-learning method includes that disclosed in "Two Stream Convolutional Networks for Action Recognition in Videos", by Simonyan et al., the entire contents of which is incorporated by reference herein. According to yet further aspects, trajectory-based handcrafted features may be efficient and robust. Example trajectory-based handcrafted feature methods include those disclosed in "Action Recognition by Dense Trajectories", by Wang et al., of Proceedings of the IEEE Conference on Computer Vision and Pattern Recognition, and "Action Recognition with Improved Trajectories" by Wang et al., of Proceedings of the IEEE International Conference on Computer Vision, the entire contents of each are each hereby incorporated by reference herein.

3.2.1 Trajectory Based Handcrafted Features

A main idea of trajectory-based feature extraction is selecting extended image features along point trajectories. Motion-based descriptors, such as histogram of flow (HOF) and motion boundary histograms (MBH), may be used in activity recognition for their good performance. According to various aspects, trajectory-based activity recognition may include the following steps: 1) computing the dense trajectories based on optical flow; 2) extracting descriptors along those dense trajectories; 3) encoding dense descriptors by Fisher vector; and 4) training a classifier with the encoded histogram-based features. One example of encoding dense descriptors by Fisher vector is described in "Fisher Kernels on Visual Vocabularies for Image Categorization" by Perronnin et al., of Proceedings of the IEEE Conference on Computer Vision and Pattern Recognition, the entire contents of which is hereby incorporated by reference herein.

According to various aspects of the present disclosure, each instance may be cropped from raw clips with a fixed bounding box that bounds the character over time. According to various aspects described herein, trajectory-based activity features may be extracted. In one example, the methods described in "Efficient Feature Extraction, Encoding and Classification for Action Recognition" by Kantorov et al., the entire contents of which is incorporated by reference herein, may be used to extract trajectory-based activity features (e.g., "fastvideofeat" by vadimkantorov). According to aspects described herein, twenty-six (26) support-vector machine (SVM) classifiers may be trained for the binary categorical emotion classification and three (3) SVM regressors for the dimensional emotion regression. The penalty parameter is selected based on the validation set and report results on the test set.

3.2.2 Deep Activity Features

According to aspects of the present disclosure, two-stream network-based deep-learning methods may learn to extract features in an end-to-end fashion. A model of this type may contain two convolutional neural networks (CNN). According to various aspects, one may take static images as input and the other may take stacked optical flow as input. The final prediction is an averaged ensemble of the two networks. According to aspects described herein, the learning objective of $f$ as defined in Eq. 8 may be used.

According to various embodiments described herein, two-stream networks may be implemented via an open source deep learning platform (e.g., in PyTorch). In some aspects, a 101-layer ResNet (e.g., residual network) may be used as the network architecture. One example of a 101-layer ResNet network architecture is disclosed in "Deep Residual Learning for Image Recognition", by He et al., of Proceedings of the IEEE Conference on Computer Vision and Pattern Recognition, the entire contents of which is hereby incorporated by reference herein. In some aspects, optical flow may be computed via a TVL1 optical flow algorithm. One example TVL1 optical flow algorithm includes that disclosed in "A Duality Based Approach for Realtime TV-L 1 Optical Flow", by Zach et al., of Proceedings of the Joint Pattern Recognition Symposium, the entire contents of which is hereby incorporated by reference herein. According to various aspects, both image and optical flow may be cropped with the instance body centered. Since emotion understanding could be potentially related to color, angle, and position, no data augmentation strategies were applied. According to some aspects, a training procedure may be implemented. One example training procedure includes that disclosed in "Two Stream Convolutional Networks for Action Recognition in Videos", by Simonyan et al., the entire contents of which is incorporated by reference herein, where the learning rate is set to 0.01. In some aspects, a ResNet-101 model may be pre-trained on an annotated image dataset (e.g., ImageNet) to initialize the network weights. As one example, the training takes around 8 minutes for one epoch with an NVIDIA Tesla K40 card. The training time may be short because only one frame may be sampled input for each video in the RGB stream, and 10 frames may be concatenated along the channel dimension in the optical flow stream. According to various aspects, the BoLD validation set may be used to choose the model of the lowest loss. Such a model, as described herein, may be named TS-ResNet101.

In some aspects, besides the original two-stream network, two other variants of action recognition may be evaluated. For temporal segment networks (TSN), each video may be divided into K segments. In such an aspect, one frame may be randomly sampled for each segment during the training stage. Video classification results may be averaged over all sampled frames. According to aspects of the present disclosure, the learning rate may be set to 0.001 and the batch size may be set to 128. For two-stream inflated 3D ConvNet (I3D), 3D convolution replaces 2D convolution in the original two-stream network. One example of I3D is disclosed in "Quo Vadis, Action Recognition? A New Model and the Kinetics Dataset", by Carreira et al., the entire contents of which is hereby incorporated by reference herein. With 3D convolution, the architecture can learn spatiotemporal features in an end-to-end fashion. This architecture may leverages advances in image classification by duplicating weights of pre-trained image classification model over the temporal dimension and using them as initialization. According to aspects of the present disclosure, the learning rate may be set to 0.01 and the batch size may be set to 12. Both experiments may be conducted on a server with two NVIDIA Tesla K40 cards. According to such aspects, further training details may include those as disclosed in "Temporal Segment Networks: Towards Good Practices for Deep Action Recognition", by Wang et al., and "Quo Vadis, Action Recognition? A New Model and the Kinetics Dataset", by Carreira et al., the entire contents of each are each incorporated by reference herein.

3.3 Results 3.3.1 Evaluation Metrics

All methods on the BoLD testing set are evaluated. According to aspects described herein, for categorical emotion, average precision (AP, area under precision recall curve) and area under receiver operating characteristic curve (ROC AUC) are used to evaluate the classification performance. Further, according to aspects described herein, for dimensional emotion, $R^2$ is used to evaluate regression performance. According to some aspects, a random baseline of AP is the proportion of the positive samples (P.P.). ROC AUC could be interpreted as the possibility of choosing the correct positive sample among one positive sample and one negative sample; a random baseline for that is 0.5. According to various aspects, to compare performance of different models, mean $R^2$ score ($mR^2$) over the three (3) dimensional emotion, as well as mean average precision (mAP), and mean ROC AUC (mRA) over the twenty-six (26) categories of emotion may be calculated. For the ease of comparison, an emotion recognition score (ERS) is defined as follows and use it to compare performance of different methods:

$$ERS=\frac{1}{2}(mR^2+\frac{1}{2}(mAP+mRA)). \qquad (9)$$

3.3.2 LMA Feature Significance Test

According to aspects of the present disclosure, for each categorical emotion and dimension of VAD, linear regression tests on each dimension of features listed in Table 2 may be conducted. All tests may be conducted using the BoLD testing set. According to aspects described herein, strong correlations (e.g., $R^2 < 0.02$) over LMA features and dimensional emotions other than arousal were not discovered, (e.g., categorical emotion and valence and dominance). Arousal, however, seems to be significantly correlated with LMA features. FIGS. 14A-14I illustrate the kernel density estimation plots of LMA features with top $R^2$ on arousal (e.g., LMA features that have a high correlation with arousal). Hands-related features are good indicators for arousal. With hand acceleration, alone, $R^2$ can be achieved as 0.101 (see FIG. 14B, $f_{16}^{max}$ FIG. 14C, $f_{16}^{mean}$ respectively). Other significant features for predicting arousal are hands velocity (FIG. 14A, $f_{13}^{mean}$), shoulders acceleration (FIG. 14D, $f_{13}^{mean}$), shoulder jerk (FIG. 14E, $f_{31}^{mean}$, elbow acceleration (FIG. 14F, $f_{33}^{mean}$), elbow jerk (FIG. 14G, $f_{34}^{mean}$), and hands jerk (see FIGS. 14H, $f_{40}^{max}$ and 14I, $f_{40}^{mean}$, respectively).

3.3.3 Model Performance

Table 3 illustrates the results on the emotion classification and regression tasks. More specifically, Table 3 depicts dimensional emotion regression and categorical emotion classification performance on the BoLD testing set. In view of Table 3, $mR^2$ denotes the mean of $R^2$ over dimensional emotions, mAP (%) denotes average precision/area under the precision recall curve (PR AUC) over categorical emotions, mRA (%) denotes mean of area under the receiver operating characteristic curve (ROC AUC) over categorical emotions, and ERS denotes the emotion recognition score of Eq. 9. Further in view of Table 3, baseline methods include Spatial Temporal Graph Convolutional Networks (ST-GCN), Trajectory-Based Activity Features (TF), Two-Stream Network-Based Deep-Learning Method with 101-layer ResNet (TS-ResNet 101), Two-Stream Inflated 3D Convolution Network (I3D), and Two-Stream Temporal Segment Network (TSN), as described herein. TSN achieves the best performance, with a mean $R^2$ of 0.095, a mean average precision of 17.02%, a mean ROC AUC of 62.70%, and an ERS of 0.247.

TABLE 3

| Model | Regression | Classification | | |
|---|---|---|---|---|
| | $mR^2$ | mAP | mRA | ERS |
| A Random Method based on Priors: | | | | |
| Chance | 0 | 10.55 | 50 | 0.151 |
| Learning from Skeleton: | | | | |
| ST-GCN | 0.044 | 12.63 | 55.96 | 0.194 |
| LMA | 0.075 | 13.59 | 57.71 | 0.216 |
| Learning from Pixels: | | | | |
| TF | −0.008 | 10.93 | 50.25 | 0.149 |
| TS-ResNet101 | 0.084 | 17.04 | 62.29 | 0.240 |
| I3D | 0.098 | 15.37 | 61.24 | 0.241 |
| TSN | 0.095 | 17.02 | 62.70 | 0.247 |
| TSN-Spatial | 0.048 | 15.34 | 60.03 | 0.212 |
| TSN-Flow | 0.098 | 15.78 | 61.28 | 0.241 |

FIGS. 15A-15D illustrate detailed metric comparisons over all methods of each categorical and dimensional emotion. More specifically, FIGS. 15A-15D depict classification performance (e.g., AP: average precision in top left portion of FIGS. 15A-15D, and RA: ROC AUC in top right portion of FIGS. 15A-15D) and regression performance (e.g., $R^2$ in bottom portion of FIGS. 15A-15D) of the various methods (e.g., Chance, ST-GCN, LMA, TF, TS-ResNet101, I3D, TSN, TSN-Spatial, TSN-Flow) on each categorical emotion and dimensional emotion (e.g., key in top portion of FIGS. 15A-15D).

Referring again to Table 3, for the pipeline that learns from the skeleton, both LMA and ST-GCN achieved above-chance results. The handcrafted LMA features, according to the various embodiments as described herein, perform better than end-to-end ST-GCN under all evaluation metrics. For the pipeline that learns from pixels, trajectory-based activity features (e.g., TF) did not achieve above-chance results for both regression and only slightly above for classification task. However, two-stream network-based methods (e.g., TS-ResNet101, I3D, TSN) achieved significant above-chance results for both regression and classification tasks. As shown in FIGS. 15A-15D and Table 1, most top-performance categories, such as affection, happiness, pleasure, excitement, sadness, anger, and pain, receive high agreement (κ) among annotators. Similar to the results from skeleton-based methods (e.g., ST-GCN, LMA), two-stream network-based methods (e.g., TS-ResNet101, I3D, TSN) show better regression performance over arousal than for valence and dominance. However, as shown in FIG. 12D, participants with top 10% performance has $R^2$ score of 0.48, −0.01, and 0.16 for valence, arousal, and dominance, respectively. Accordingly, it appears that humans are best at recognizing valence and worst at recognizing arousal, and the distinction between human performance and model performance may suggest that there could be other useful features that each individual model has not explored.

3.4 Ablation Study

To further understand the effectiveness of the two-stream-based model (e.g., TS-ResNet101, I3D, TSN) on the task, two sets of experiments are conducted to diagnose: 1) if the task could leverage learned filters from a pre-trained activity-recognition model, and 2) how much a person's face contributed to the performance in the model. Since TSN has shown the best performance among all two-stream-based models, all experiments are conducted with TSN in this subsection.

For the first set of experiments, different pre-trained models, e.g., an image-classification model pre-trained on an annotated image dataset (e.g., ImageNet) are used and an action recognition model pre-trained on an action dataset (e.g., Kinetics) is used to initialize TSN. Table 4 depicts the ablation study on the effect of pre-trained models and shows the results for each case. The results demonstrate that initializing with the pre-trained ImageNet model leads to slightly better emotion-recognition performance.

TABLE 4

| Pretrained | Regression | Classification | | |
|---|---|---|---|---|
| Model | $mR^2$ | mAP | mRA | ERS |
| ImageNet | 0.095 | 17.02 | 62.70 | 0.247 |
| Kinetics | 0.093 | 16.77 | 62.53 | 0.245 |

For the second set of experiments, TSN is trained with two other different input types, (e.g., face only and faceless body). The experiment in the last section crops the whole human body as the input. For face only, the face is cropped for both spatial branch (RGB image) and temporal branch (optical flow) during both the training and testing stages. Note that for the face-only setting, orientation of faces in the dataset may be inconsistent, e.g., facing forward, facing backward, or facing to the side. For the faceless body, the whole body is still cropped, but the region of face is masked by imputing pixel value with a constant 128. Table 5 depicts the ablation study on the effect of face and shows the results for each setting. It can be seen from the results that the performance of using either the face or the faceless body as input is comparable to that of using the whole body as input. This result suggests both face and the rest of the body contribute significantly to the final prediction. Although the "whole body" setting of TSN performs better than any of the single model do, it does so by leveraging both facial expression and bodily expression.

TABLE 5

| Input Type | Regression $mR^2$ | Classification mAP | mRA | ERS |
|---|---|---|---|---|
| whole body | 0.095 | 17.02 | 62.70 | 0.247 |
| face only | 0.092 | 16.21 | 62.18 | 0.242 |
| faceless body | 0.088 | 16.61 | 62.30 | 0.241 |

3.5 ARBEE: Automated Recognition of Bodily Expression of Emotion

According to various aspects of the present disclosure, the Automated Recognition of Bodily Expression of Emotion (ARBEE) system may be constructed by ensembling the best models of the different modalities (e.g., best/highest ranked models, best/highest ranked pre-trained models). As suggested in the previous subsection, different modalities may provide complementary clues for emotion recognition. According to various aspects, the prediction is averaged from different models (e.g., TSN-body: TSN trained with whole body, TSN-face: TSN trained with face, and LMA: random forest model with LMA features) and the performance on the BoLD testing set is evaluated. Table 6 shows the results of ensembled results. According to Table 6, combining all modalities, e.g., body, face and skeleton (LMA), achieves the best performance. According to embodiments of the present disclosure, ARBEE is the average ensemble of the three models (e.g., TSN-body, TSN-face, and LMA).

TABLE 6

| Model | Regression $mR^2$ | Classification mAP | mRA | ERS |
|---|---|---|---|---|
| TSN-body | 0.095 | 17.02 | 62.70 | 0.247 |
| TSN-body + LMA | 0.101 | 16.70 | 62.75 | 0.249 |
| TSN-body + TSN-face | 0.101 | 17.31 | 63.46 | 0.252 |
| TSN-body + TSN-face + LMA | 0.103 | 17.14 | 63.52 | 0.253 |

A further investigation into how well ARBEE retrieves instances in the BoLD testing set given a specific categorical emotion as query is conducted. Concretely, precision is calculated at 10, 100, and R-Precision as summarized in Table 7. More specifically, Table 7 depicts retrieval results of the deep model where P@K (%) denotes precision at K and R-P (%) denotes R-Precision. According to various aspects, R-Precision may be computed as precision at R, where R is number of positive samples. Similar to the classification results, happiness and pleasure can be retrieved with a rather high level of precision.

TABLE 7

| Category | P@10 | P@100 | R-P |
|---|---|---|---|
| Peace | 40 | 33 | 28 |
| Affection | 50 | 32 | 26 |
| Esteem | 30 | 14 | 12 |
| Anticipation | 30 | 24 | 20 |
| Engagement | 50 | 46 | 42 |
| Confidence | 40 | 33 | 31 |
| Happiness | 30 | 36 | 31 |
| Pleasure | 40 | 25 | 23 |
| Excitement | 50 | 41 | 31 |
| Surprise | 20 | 6 | 8 |
| Sympathy | 10 | 14 | 12 |
| Doubt/Confusion | 20 | 33 | 25 |
| Disconnection | 20 | 20 | 18 |
| Fatigue | 40 | 20 | 17 |
| Embarrassment | 0 | 5 | 5 |
| Yearning | 0 | 2 | 4 |
| Disapproval | 30 | 28 | 22 |
| Aversion | 10 | 10 | 11 |
| Annoyance | 30 | 28 | 23 |
| Anger | 40 | 24 | 20 |
| Sensitivity | 30 | 19 | 19 |
| Sadness | 50 | 34 | 25 |
| Disquietment | 10 | 26 | 25 |
| Fear | 10 | 8 | 8 |
| Pain | 20 | 9 | 12 |
| Suffering | 10 | 17 | 18 |
| Average | 27 | 23 | 20 |

4.0 CONCLUSIONS

According to various aspects described herein, a scalable and reliable video-data collection pipeline may be used to collect a large-scale bodily expression dataset, e.g., the BoLD dataset. Such data collection has been validated via statistical analysis. The effort, as disclosed herein, is the first quantitative investigation of human performance on emotional expression recognition with thousands of people, tens of thousands of clips, and thousands of characters. According to aspects described herein, significant predictive features regarding the computability of bodily emotion, e.g., hand acceleration for emotional expressions along the dimension of arousal, have been revealed. Moreover, the ensembled model, as described herein, demonstrates decent generalizability for bodily expression recognition in the wild.

According to various aspects described herein, the model's regression performance of arousal is clearly better than that of valence, yet the analysis shows humans are better at recognizing valence. Further, the analysis has identified demographic factors in emotion perception between different ethnic groups. According to further aspects of the present disclosure, characters' demographics in the inference of bodily expression may be considered in the model. According to yet further aspects, several other modalities within the BoLD dataset, including audio and visual context, may be considered in the model.

It should now be understood that the systems and methods described herein are flexibly applicable to any real-world situation (e.g., system models based on crowdsourced-derived underlying in-the-wild data, useful for day-to-day scenarios), usable indoors and/or outdoors (e.g., system based on body movements, joints, connectivity of joints and/or the like and not constrained with respect to background or environment), with or without a full body view (e.g., system is based on what is seen, not what is not seen), regardless of whether a subject's face is visible (e.g., not dependent on FACS), and without a need for depth (e.g., uses 2D versus 3D) and/or motion capture systems (e.g., Kinect, MoCap, and/or the like)

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. An emotion analysis and recognition system, comprising:
 a query system configured to interact with a user; and
 an automated recognition of bodily expression of emotion (ARBEE) system communicatively coupled to the query system, the ARBEE system having a processor and a memory storing program instructions, the program instructions executable by the processor to:
  receive a plurality of body movement models, each body movement model generated based on a crowdsourced body language dataset;
  calculate at least one evaluation metric for each body movement model, the at least one evaluation metric to evaluate a classification performance for each of a plurality of categorical emotions and/or to evaluate regression performance for each of a plurality of dimensional emotions, the categorical and dimensional emotions being determined based on a combination of movements for body parts of subjects, facial expressions of the subjects, associated audio, associated context, and a pixel analysis of cropped images of a human body;
  select a highest ranked body movement model based on the at least one evaluation metric calculated for each body movement model;
  combine the highest ranked body movement model with at least one other body movement model of the plurality of body movement models;
  calculate at least one evaluation metric for each combination of body movement models;
  determine a highest ranked combination of body movement models;
  based on the determined highest ranked combination of body movement models, predict a bodily expression of emotion;
  receive, from the query system, a video;
  apply the received video as input to the highest ranked combination of body movement models; and
  transmit an emotion result to the query system, the emotion result providing information usable by the query system for determining an emotion of a target,
 wherein the query system interacts with the user based on the emotion result received from the ARBEE system.

2. The system of claim 1, wherein the at least one evaluation metric for each body movement model includes one or more of:
 an average precision (AP) defined by an area under a precision recall curve;
 a receiver operating characteristic area under the curve (ROC AUC) defined by an area under a receiver operating characteristic curve;
 a coefficient of determination $R^2$;
 a mean AP (mAP);
 a mean ROC AUC (mRA); and
 a mean $R^2$ (mR$^2$).

3. The system of claim 2, wherein the at least one evaluation metric for each combination of body movement models includes an emotion recognition score (ERS) defined as:

$$ERS=\frac{1}{2}(mR^2+\frac{1}{2}(mAP+mRA)).$$

4. The system of claim 1, wherein the plurality of body movement models include models that learn from skeleton, or a combination of the models that learn from skeleton and models that learn from pixels, the models that learn from skeleton including at least one of: a Spatial Temporal Graph Convolutional Network (ST-GCN) model or a Laban Movement Analysis (LMA) model, and wherein the models that learn from pixels include at least one of: a Trajectory-Based Activity Features (TF) model, a Two-Stream Network-Based Deep-Learning Method with 101-layer ResNet (TS-ResNet 101) model, a Two-Stream Inflated 3D Convolution Network (I3D) model, or a Two-Stream Temporal Segment Network (TSN) model.

5. The system of claim 1, further comprising:
 a body language dataset (BoLD) database; and
 a crowdsourcing platform configured to:
  present video clips to a plurality of crowdsourced participants via a website;
  receive, for each video clip, annotations including the plurality of categorical emotions, the plurality of dimensional emotions, or a combination of the plurality of categorical emotions and the plurality of dimensional emotions perceived by each crowdsourced participant;
  perform quality control activities, comprising:
   apply at least one of a screening, an annotation sanity check, or a relaxed gold standard to each participant, and
   calculate a reliability score for each participant;
  aggregate, for each video clip, a plurality of categorical emotion annotations to define a consensus categorical emotion, a plurality of dimensional emotion annotations to define a consensus dimensional emotion, or the plurality of categorical emotion annotations to define the consensus categorical emotion and the plurality of dimensional emotion annotations to define the consensus dimensional emotion; and
  transmit each video clip and its associated consensus categorical emotion, its associated consensus dimensional emotion, or its associated consensus categorical emotion and its associated consensus dimensional emotion for storage in the BOLD database.

6. The system of claim 1, wherein the ARBEE system is further configured to:
 receive one or more than one modality model, each modality model generated based on data associated with a modality other than body movement; and
 combine the highest ranked combination of body movement models with at least one modality model to predict the bodily expression of emotion.

7. The system of claim 1, wherein the query system comprises a video camera and a display screen.

8. The system of claim 7, wherein the query system is an interactive robot system that interacts with the user.

9. An emotion analysis and recognition system, comprising:
 a query system configured to interact with a user; and
 an automated recognition of bodily expression of emotion (ARBEE) system communicatively coupled to the query system, the ARBEE system having a processor and a memory storing program instructions, the program instructions executable by the processor to:
  receive a plurality of body movement models, each body movement model generated based on a body language dataset;
  calculate at least one evaluation metric for each body movement model, the at least one evaluation metric to evaluate a classification performance for each of a plurality of categorical emotions and/or to evaluate regression performance for each of a plurality of dimensional emotions, the categorical and dimensional emotions being determined based on a combination of movements for body parts of subjects, facial expressions of the subjects, associated audio, associated context, and a pixel analysis of cropped images of a human body;

select a highest ranked body movement model based on the at least one evaluation metric calculated for each body movement model;

initialize the highest ranked body movement model with one or more pre-trained model;

calculate at least one evaluation metric for each initialized body movement model;

combine the highest ranked initialized body movement model with at least one other body movement model of the plurality of body movement models, the at least one other body movement model including one or more other initialized body movement models;

calculate at least one evaluation metric for each combination of body movement models;

determine a highest ranked combination of body movement models;

based on the determined highest ranked combination of body movement models, predict a bodily expression of emotion;

receive, from the query system, a video;

apply the received video as input to the highest ranked combination of body movement models; and transmit an emotion result to the query system, the emotion result providing information usable by the query system for determining an emotion of a target, wherein the query system interacts with the user based on the emotion result received from the ARBEE system.

10. The system of claim 9, wherein:
the highest ranked body movement model includes a Two-Stream Temporal Segment Network (TSN) model, wherein the one or more pre-trained model includes a model pre-trained on an annotated image dataset, a model pre-trained on an action dataset, a model pre-trained on a face only dataset, and a model pre-trained on faceless body dataset, the highest ranked combination of body movement models includes a TSN model initialized with the model pre-trained on the annotated image dataset, a TSN model initialized with the model pre-trained on the face only dataset, and a Laban Movement Analysis (LMA) model, and the LMA model is based on features including one or more of: feet-hip distance, hands-shoulder distance, hands distance, hands-head distance, centroid-pelvis distance, foot distance, shoulders velocity, acceleration and jerk, elbow velocity, acceleration, and jerk, hands velocity, acceleration, and jerk, hip velocity, acceleration, and jerk, knee velocity, acceleration, and jerk, feet velocity, acceleration, and jerk, angular velocity, angular acceleration, volume total, upper body, lower body, left side, and right side, and torso height.

11. The system of claim 9, wherein the ARBEE system is further configured to:
receive one or more than one modality model, each modality model generated based on data associated with a modality other than body movement selected from includes face, touch, eye contact, vocal cue, or a combination thereof; and combine the highest ranked combination of body movement models with at least one modality model to predict the bodily expression of emotion.

12. An emotion analysis and recognition method, the method comprising:
receiving, by an automated recognition of bodily expression of emotion (ARBEE) system having a special purpose computer with program instructions executable by a processor, a plurality of body movement models, each body movement model generated based on a crowdsourced body language dataset;

calculating, by the ARBEE system, at least one evaluation metric for each body movement model, the at least one evaluation metric to evaluate a classification performance for each of a plurality of categorical emotions and/or to evaluate regression performance for each of a plurality of dimensional emotions, the categorical and dimensional emotions being determined based on a combination of movements for body parts of subjects, facial expressions of the subjects, associated audio, associated context, and a pixel analysis of cropped images of a human body;

selecting, by the ARBEE system, a highest ranked body movement model based on the at least one evaluation metric calculated for each body movement model;

combining, by the ARBEE system, the highest ranked body movement model with at least one other body movement model of the plurality of body movement models;

calculating, by the ARBEE system, at least one evaluation metric for each combination of body movement models;

determining, by the ARBEE system, a highest ranked combination of body movement models;

based on the determined highest ranked combination of body movement models, predicting, by the ARBEE system, a bodily expression of emotion;

receiving, by the ARBEE system from a query system, a video;

applying, by the ARBEE system, the received video as input to the highest ranked combination of body movement models;

transmitting, by the ARBEE system, an emotion result to the query system, the emotion result providing information usable by the query system for determining an emotion of a target; and interacting, by the query system, with a user based on the emotion result received from the ARBEE system.

13. The method of claim 12, wherein the at least one evaluation metric for each body movement model includes one or more of:
an average precision (AP) defined by an area under a precision recall curve;
a receiver operating characteristic area under the curve (ROC AUC) defined by an area under a receiver operating characteristic curve;
a coefficient of determination $R^2$;
a mean AP (mAP);
a mean ROC AUC (mRA); and
a mean $R^2$ (m$R^2$).

14. The method of claim 13, wherein the at least one evaluation metric for each combination of body movement models includes an emotion recognition score (ERS) defined as:

$$ERS = \tfrac{1}{2}(mR^2 + \tfrac{1}{2}(mAP + mRA)).$$

15. The method of claim 12, wherein the plurality of body movement models include models that learn from skeleton, models that learn from pixels, or a combination of the models that learn from skeleton and the models that learn from pixels.

16. The method of claim 15, wherein the models that learn from skeleton include at least one of: a Spatial Temporal Graph Convolutional Network (ST-GCN) model or a Laban Movement Analysis (LMA) model, and wherein the models that learn from pixels include at least one of: a Trajectory-Based Activity Features (TF) model, a Two-Stream Network-Based Deep-Learning Method with 101-layer ResNet (TS-ResNet 101) model, a Two-Stream Inflated 3D Convolution Network (I3D) model, or a Two-Stream Temporal Segment Network (TSN) model.

17. The method of claim 12, further comprising:
presenting, by a crowdsourcing platform, video clips to a plurality of crowdsourced participants via a website;
receiving for each video clip, by the crowdsourcing platform, annotations including the plurality of categorical emotions, the plurality of dimensional emotions, or a combination of the plurality of categorical emotions and the plurality of dimensional emotions perceived by each crowdsourced participant;
performing, by the crowdsourcing platform, quality control activities;
aggregating for each video clip, by the crowdsourcing platform, a plurality of categorical emotion annotations to define a consensus categorical emotion, a plurality of dimensional emotion annotations to define a consensus dimensional emotion, or the plurality of categorical emotion annotations to define the consensus categorical emotion and the plurality of dimensional emotion annotations to define the consensus dimensional emotion; and
transmitting, by the crowdsourcing platform, each video clip and its associated consensus categorical emotion, its associated consensus dimensional emotion, or its associated consensus categorical emotion and its consensus dimensional emotion to a body language dataset (BoLD) database for storage.

18. The method of claim 17, wherein performing the quality control activities includes:
applying at least one of a screening, an annotation sanity check, or a relaxed gold standard to each participant; and
calculating a reliability score for each participant.

19. The method of claim 12, further comprising:
receiving, by the ARBEE system, one or more than one modality model, each modality model generated based on data associated with a modality other than body movement; and
combining, by the ARBEE system, the highest ranked combination of body movement models with at least one modality model to predict the bodily expression of emotion.

20. The method of claim 19, wherein the modality other than body movement includes face, touch, eye contact, vocal cue, or a combination thereof.

* * * * *